United States Patent
Reddy et al.

(10) Patent No.: US 9,822,113 B2
(45) Date of Patent: Nov. 21, 2017

(54) TRICYCLIC COMPOUNDS AND PROCESS FOR PREPARATION THEREOF

(71) Applicant: Council of Scientific & Industrial Research, New Delhi (IN)

(72) Inventors: Dumbala Srinivasa Reddy, Maharashtra (IN); Rahul Dilip Shingare, Maharashtra (IN); Velayudham Ramadoss, Maharashtra (IN)

(73) Assignee: Council of Scientific & Industrial Research, New Delhi (IN)

( * ) Notice: Subject to any disclaimer, the term of this patent is extended or adjusted under 35 U.S.C. 154(b) by 0 days.

(21) Appl. No.: 14/904,680

(22) PCT Filed: Jul. 14, 2014

(86) PCT No.: PCT/IN2014/000465
§ 371 (c)(1),
(2) Date: Jan. 12, 2016

(87) PCT Pub. No.: WO2015/004687
PCT Pub. Date: Jan. 15, 2015

(65) Prior Publication Data
US 2016/0152616 A1  Jun. 2, 2016

(30) Foreign Application Priority Data

Jul. 12, 2013 (IN) .......................... 2101/DEL/2013

(51) Int. Cl.
C07D 471/06 (2006.01)
A61K 31/498 (2006.01)

(52) U.S. Cl.
CPC .................................. *C07D 471/06* (2013.01)

(58) Field of Classification Search
None
See application file for complete search history.

(56) References Cited

U.S. PATENT DOCUMENTS

| | | | |
|---|---|---|---|
| 5,114,949 A | 5/1992 | Gueremy et al. | |
| 5,273,975 A | 12/1993 | Moon et al. | |
| 6,355,802 B1 * | 3/2002 | Wuts ................... | C07D 471/06 546/64 |

OTHER PUBLICATIONS

Wuts et al., Pure and Applied Chemistry (2002), 74(8), pp. 1359-1368.*

Database CAPLUS in STN, Acc. No. 2002:749267, Wuts et al., Pure and Applied Chemistry (2002), 74(8), pp. 1359-1368 (abstract).*

Database CAPLUS in STN, Acc. No. 2000:553580, Wuts et al., WO 2000046226 A1 (part of U.S. Pat. No. 6,355,802 B1 patent family) (Aug. 10, 2000) (abstract).*

El'Tsov and Khokhlov, "Derivatives of Imidazo [4,5-ij]quinolinium, I," Zhurnal Organicheskoi Khimii (1970), 6(12):2618-2625.

Hu et al., "Hunanamycin A, an Antibiotic from a Marine-Derived Bacillus hunanensis," *Organic Letters* (2013), 15(2):390-393, American Chemical Society.

Poludnenko and Simonov,,"5,6-Dihydro-4h-imidazole[4,5,1-I,j]quinolone Derivatives," *Chemistry of Heterocyclic Compounds* (1970), 6(10):13717-1320, Consultants Bureau, Plenum Publishing Corporation.

Swamy, K. C. Kumara et al.: "*Mitsunobu and Related Reactions: Advances and Applications*"; Chem. Rev. 2009, 109, 2551-2651.

Thakuria, Harjyoti et al.: "*One-pot efficient green synthesis of 1,4-dihydro-quinoxaline-2,3-dione derivatives*"; J. Chem. Sci., vol. 118, No. 5, Sep. 2006, pp. 425-428.

\* cited by examiner

*Primary Examiner* — Brian J Davis
(74) *Attorney, Agent, or Firm* — DLA Piper LLP (US)

(57) ABSTRACT

The present invention relates to novel tricyclic compounds of formula (I) and (II) More particularly, the present invention relates to novel tricyclic compounds of formula (I) and (II) and process of preparation of these compounds from 4,5-di-methyl-o-phenylinediamine. Further, the present invention relates to a process for preparation of tricyclic compound hunanamycin A.

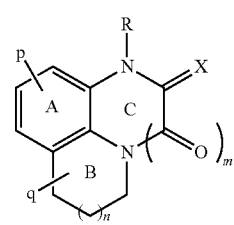

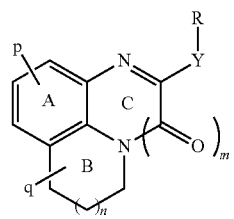

9 Claims, No Drawings

TRICYCLIC COMPOUNDS AND PROCESS FOR PREPARATION THEREOF

CROSS-REFERENCE TO RELATED APPLICATIONS

This application is a 35 USC §371 National Stage application of International Application No. PCT/IN2014/000465 filed Jul. 14, 2014, now pending; which claims the benefit under 35 USC §119(a) to India Application No. 2101/DEL/2013 filed Jul. 12, 2013. The disclosure of each of the prior applications is considered part of and is incorporated by reference in the disclosure of this application.

FIELD OF THE INVENTION

The present invention relates to novel tricyclic compounds of formula (I) and formula (II) and a process of preparation thereof. The present invention also relates to a process for the preparation of tricyclic compound hunanamycin A.

BACKGROUND AND PRIOR ART

Infectious diseases caused by the various bacteria remain one of most dangerous threats to human beings despite the availability of several antibiotics and vaccines. The misuse or overuse of antibacterial agents led to the emergence of multidrug resistant bacterial pathogens. In addition, bacteria often resilient enough to survive in even the extreme environments through evolution of different mechanisms. Hence, there is an urgent need for novel antibacterials to address resistance with novel mechanisms. Hunanamycin A is the first natural product with a pyrido[1,2,3-de]quinoxaline-2,3-dione core related to a degradation product of riboflavin (vitamin-B2).

Article titled "One-pot efficient green synthesis of 1,4-dihydro-quinoxaline-2,3-dione derivatives "by *J. Chem. Sci.*, 2006, 118 (5), pp. 425-428 reports newer and cleaner processes for organic transformations and Synthesis of these potential pharmacophore 1,4-dihydro-quinoxaline-2,3-dione. They report simple solid phase grinding of substituted o-phenylinediamine and oxalic acid at room temperature in good yield.

Article titled "Mitsunobu and Related Reactions: Advances and Applications" by K. Swamy et al. published in *Chem. Rev.*, 2009, 109 (6), pp 2551-2651 reports the reaction involves C—O, C—S, C—N, or C—C bond formation by the condensation of an acidic component with a primary or a secondary alcohol in the presence of triphenylphosphine (or another suitable phosphine) and diethyl azodicarboxylate (DEAD) or diisopropyl azodicarboxylate (DIAD).

Article titled, "Hunanamycin A, an Antibiotic from a Marine-Derived *Bacillus* hunanensis' by MacMillan et al. published in *Org. Lett.*, 2013, 15 (2), pp 390-393 isolation of hunanamycin A from a marine-derived bacteria *Bacillus hunanensis* by. Also reports Hunanamycin A exhibits a minimum inhibitory concentration (MIC) of 12.4 µM against the bacterial pathogen *Salmonella enterica*. The gross structure and stereo chemical assignments of hunanamycin A were predicted using extensive spectroscopic data analysis and by comparing the data with riboflavin, a structurally relevant compound. As the structure of hunanamycin A was related to riboflavin degradation products, MacMillan group screened it for antimicrobial activity against bacterial strains that lacked riboflavin transport mechanisms. The compound hunanamycin A showed minimum inhibitory concentration (MIC) of 12.4 µM against *Salmonella enterica* suggesting it is an inhibitor of riboflavin synthase (ribB).

Riboflavin synthase is an enzyme that catalyzes the final step in the biosynthesis of riboflavin. In disease models of *Salmonella* infection, knockout of the riboflavin synthase was shown to be lethal to the pathogen. The target ribB has been shown to be an attractive antibiotic target as human beings lack this target. As the target compound hunanamycin A showed to be selective towards the inhibition of *Salmonella enterica* (based on screening with limited no. of organisms), the scaffold may be used for the development of antibacterial agents for killing *Salmonella* bacteria.

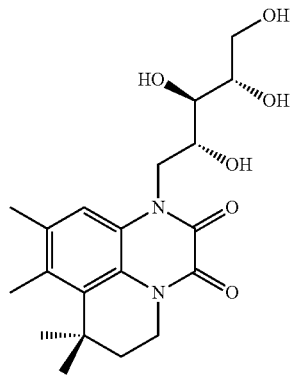

Hunanamycin A 7,7,8,9-tetramethyl-1-((2S,3S,4R)-2,3,4,5-tetrahydroxypentyl)-6,7-dihydro-1H,5H-pyrido[1,2,3-de]quinoxaline-2,3-dione Further to MacMillan et al's isolation, there is no prior art on total synthesis or approach towards hunanamycin A reported in the literature.

Therefore there is a need in the art to provide synthetic route for hunanamycin A and related compounds. Also, the process disclosed herein will produce sufficient quantities of hunanamycin A and related compounds for more involved biological evaluation of the compounds.

Objects of Invention

The main object of the present invention is to provide novel tricyclic compounds of formula (I) and formula (II).

One more object of the invention is to provide a process of preparation of novel tricyclic compounds formula (I) and formula (II).

Yet another object of present invention is to provide a process for the preparation of tricyclic compounds hunanamycin A with better yield.

SUMMARY OF THE INVENTION

Accordingly, the present invention provides novel tricyclic compounds of formula (I) and formula (II)

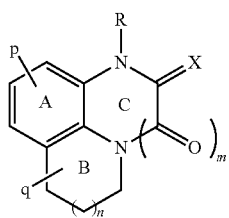

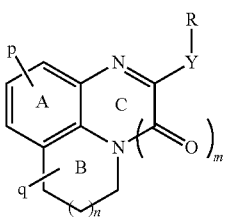

Wherein X=O or S;

Wherein Y=O, NH, N-alkyl;

Wherein R is selected from hydrogen, sugar, sugar mimic, alkyl, aralkyl, heteroaralkyl, haloalkyl, hydroxyalkyl, thioalkyl, C1-C5 alkoxyalkyl, aminoalkyl, —NR'R", —CH2NR'R"—CONR'R", —COOR'";

Wherein R', R" are independently hydrogen or alkyl, aryl which may have additional substitution;

R' and R" together form a ring with up to six carbon atoms which optionally may be substituted and/or may contain hetero atoms;

R'" is hydrogen or alkyl, aryl which may have additional substitution;

n=0, 1, 2, 3 m=0, 1

Ring A may be substituted (p) with up to three substitutions which are same or different groups and they are selected from hydrogen, halogen, alkyl, haloalkyl, hydroxyalkyl, thioalkyl, C1-C5 alkoxyalkyl, nitro, aminoalkyl, —NR'R", —CH2NR'R"—CONR'R", —COOR'";

Wherein R', R" are independently hydrogen or alkyl, aryl which may have additional substitution;

R' and R" together form a ring with up to six carbon atoms which optionally may be substituted and/or may contain hetero atoms;

R'" is hydrogen or alkyl, aryl which may have additional substitution;

Substitutions on ring A together form an additional ring which optionally may be substituted and/or may contain hetero atoms;

Ring B may be further substituted (q) with same or different groups and they are selected from hydrogen, halogen, alkyl, haloalkyl, hydroxyalkyl, thioalkyl, C1-C5 alkoxyalkyl, nitro, aminoalkyl, —NR'R", —CH2NR'R"—CONR'R", —COOR'";

Wherein R', R" are independently hydrogen or alkyl, aryl which may have additional substitution;

R' and R" together form a ring with up to six carbon atoms which optionally may be substituted and/or may contain hetero atoms;

R'" is hydrogen or alkyl, aryl which may have additional substitution;

Substitutions on ring B together form an additional ring which optionally may be substituted and/or may contain hetero atoms; and pharmaceutically acceptable salts thereof.

The tricyclic compounds of formula (I) and formula (II), wherein the compound is 7,7,8,9-tetramethyl-2-((2,3,4,5-tetrahydroxypentyl)oxy)-6,7-dihydro-3H,5H-pyrido[1,2,3-de]quinoxalin-3-one.

Further, the invention provides a process for the preparation of novel tricyclic compounds of formula (I) and (II) from 4,5-dimethyl-1,2-phenylenediamine comprising the steps of N-prenylation, friedel-craft alkylation, C—N bond formation followed by ribose construction.

Another embodiment of the invention is to provide tricyclic compounds of formula (I) and formula (II) for use as an antibacterial agent.

Yet another embodiment of the invention is to provide tricyclic compounds of formula (I) and formula (II) according to claim 1, wherein the antibacterial activity is against *Salmonella enterica*.

Another aspect of the invention is to provide the process for the preparation 7,7,8,9-tetramethyl-2-((2,3,4,5-tetrahydroxypentyl)oxy)-6,7-dihydro-3H,5H-pyrido[1,2,3-de]quinoxalin-3-one comprising the following steps:

a) refluxing the mixture of 4,5-dimethyl-o-phenylenediamine dissolved in 4N HCL and oxalic acid for overnight to obtain 6,7-dimethyl-1,4-dihydroquinoxaline-2,3-dione, b) adding cesium carbonate ($Cs_2CO_3$), 3,3-dimethylallyl bromide to a solution of compound of step (a) in dry DMF followed by stirring to obtain mono alkylated and dialkylated 6,7-dimethyl-1-(3-methylbut-2-en-1-yl)-1,4-dihydro-quinoxaline-2,3-dione, c) heating the reaction mixture of compound of step (b) and $AlCl_3$ in chlorobenzene up to 120° C. for 12 hrs to obtain 7,7,8,9-tetramethyl-6,7-dihydro-1H,5H-pyrido[1,2,3-de]quinoxaline-2,3-dione, d) adding triphenylphosphine, protected sugar, diisopropyl azodicarboxylate to a solution compound of step (c) in dry THF followed by stirring to obtain 7,7,8,9-tetramethyl-2-((2,2,2',2'-tetramethyl-[4,4'-bi(1,3-dioxolan)]-5-yl)methoxy)-6,7-dihydro-3H,5H-pyrido[1,2,3-de]quinoxalin-3-one, e) stirring the solution of compound of step (d) in 1 ml of Acetic acid:Water (1:1) for 3 hrs at 60° C. to obtain of 7,7,8,9-tetramethyl-2-((2,3,4,5-tetrahydroxypentyl)oxy)-6,7-dihydro-3H,5H-pyrido[1,2,3-de]quinoxalin-3-one.

Another embodiment of the invention is to provide the process the wherein stirring in step (b) is carried out for 2 to 4 hours Yet another embodiment of the invention is to provide the process, wherein stirring in step (b) is carried out for for 3 hours at room temperature.

Also another embodiment of the invention is to provide the process wherein stirring in step (d) is carried out for 10 to 12 hours Yet another embodiment of the invention is to provide the process wherein stirring in step (d) is carried out for 12 hours at room temperature.

Another aspect of the invention is to provide a process for preparation of tricyclic compound hunanamycin A from 4,5-dimethyl-o-phenylinediamine comprising the following steps:

i.) refluxing the mixture of 4,5-dimethyl-o-phenylinediamine dissolved in 4N HCL and oxalic acid to obtain 6,7-dimethyl-1,4-dihydroquinoxaline-2,3-dione, ii.) adding cesium carbonate ($Cs_2CO_3$), 3,3-dimethylallyl bromide to a solution of step (a) in dry DMF followed by stirring at room temperature to obtain mono alkylated and dialkylated 6,7-dimethyl-1-(3-methylbut-2-en-1-yl)-1,4-dihydroquinoxaline-2,3-dione, iii.) heating the reaction mixture of step (ii) and AlCl₃ in chlorobenzene up to 120° C. for 12 hrs to obtain 7,7,8,9-tetramethyl-6,7-dihydro-1H,5H-pyrido[1,2,3-de]quinoxaline-2,3-dione, iv.) adding the solution of sodium hydride in 1 ml of DMF to a solution of compound of step (iii) in dry DMF at room temperature, adding (S,Z)-4-(3-bromoprop-1-en-1-yl)-2,2-dimethyl-1,3-dioxolane dissolved in dry DMF at 10° C. followed by stirring for 2 hours at room temperature to obtain (S,Z)-1-(3-(2,2-dimethyl-1,3-dioxolan-4-yl)allyl)-7,7,8,9-tetramethyl-6,7-dihydro-1H, 5H-pyrido[1,2,3-de]quinoxaline-2,3-dione, v.) stirring a solution of compound of step (iv) in Acetone: tBuOH:Water (7:2:1) followed by addition of solution of N-Methylmorpholine N-oxide (NMO) and Osmium tetraoxide in t-BuOH to obtain 1-((2S,3S)-3-((R)-2,2-dimethyl-1,3-dioxolan-4-yl)-2,3-dihydroxypropyl)-7, 7,8,9-tetramethyl-6,7-dihydro-1H,5H-pyrido[1,2,3-de] quinoxaline-2,3-dione, vi.) Stirring the solution of compound of step (v) in acetic acid: water for 30 min at 50° C. to obtain tricyclic compound Hunanamycin A.

Another embodiment is to provide the process wherein stirring in step (ii) is carried out for 2 to 4 hours preferably for 3 hours at room temperature.

Another embodiment is to provide the process wherein stirring in step (v) is carried out for 10 to 12 hours preferably for 12 hours at room temperature.

Yet another embodiment is to provide a method for inhibiting the growth of *Salmonella enterica* using the compound of formula 1-(((2R,3S,4R)-3,4-dihydroxy-5-methoxytetrahydrofuran-2-yl)methyl)-6,6-dimethyl-5,6-dihydro-4H-imidazo[4,5,1-ij]quinolin-2(1H)-one (compound 25) wherein the minimum inhibitory concentration is 2 µg/mL.

Another embodiment is to provide a method for inhibiting the growth of *Salmonella enterica* using the compound of formula 7,7,8,9-tetramethyl-1-(2,3,4,5-tetrahydroxypentyl)-6,7-dihydro-1H,5H-pyrido[1,2,3-de]quinoxaline-2,3-dione (compound 5), 6,6-dimethyl-1-((2S,3S,4R)-2,3,4,5-tetrahydroxypentyl)-5,6-dihydro-4H-imidazo[4,5,1-ij]quinolin-2 (1H)-one (compound 21) wherein the minimum inhibitory concentration is 4 µg/mL Also the embodiment of the invention provides a method for inhibiting the growth of *Salmonella enterica* using the compound of formula 7,7,8,9-tetramethyl-2-(((2S,3R,4R)-2, 3,4,5-tetrahydroxy-pentyl)oxy)-6,7-dihydro-3H,5H-pyrido [1,2,3-de]quinoxalin-3-one (compound 1), Hunanamycin A, 7,7,8,9-tetramethyl-1-((2R,3S,4R)-2,3,4,5-tetrahydroxy-pentyl)-6,7-dihydro-1H,5H-pyrido[1,2,3-de]quinoxaline-2, 3-dione, dihydroxypropyl)-7,7-dimethyl-6,7-dihydro-1H, 5H-pyrido[1,2,3-de]quinoxaline-2,3-dione, 1-((1-(2-hydroxyethyl)-1H-1,2,3-triazol-4-yl)methyl)-6,6-dimethyl-5,6-dihydro-4H-imidazo[4,5,1-ij]quinolin-2(1H)-one wherein the minimum inhibitory concentration is 8 µg/mL.

Another aspect of the invention is to provide a pharmaceutical composition comprising the compounds of Formula 1 or II or a stereoisomer or ester or pharmaceutically acceptable carrier, diluents, or excipients.

In another aspect, the present invention provides a process for the preparation of hunanamycin A from 4,5-dimethyl-1, 2-phenylenediamine.

DETAILED DESCRIPTION OF THE INVENTION

The invention will now be described in detail in connection with certain preferred and optional embodiments, so that various aspects thereof may be more fully understood and appreciated.

The present invention provides novel tricyclic compounds of formula (I) and formula (II)

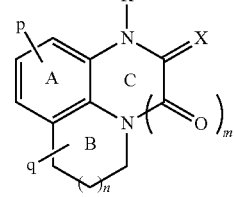

I

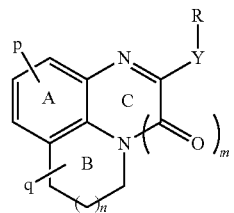

II

Wherein X=O or S;
Wherein Y=O, NH, N-alkyl;
Wherein R is selected from hydrogen, sugar, sugar mimic, alkyl, aralkyl, heteroaralkyl, haloalkyl, hydroxyalkyl, thioalkyl, C1-C5 alkoxyalkyl, aminoalkyl, —NR'R", —CH2NR'R"—CONR'R", —COOR'";

Wherein R', R" are independently hydrogen or alkyl, aryl which may have additional substitution;

R' and R" together form a ring with up to six carbon atoms which optionally may be substituted and/or may contain hetero atoms;

R'" is hydrogen or alkyl, aryl which may have additional substitution;

n=0, 1, 2, 3
m=0, 1

Ring A may be substituted with (p) up to three substitutions which are same or different groups and they are selected from hydrogen, halogen, alkyl, haloalkyl, hydroxyalkyl, thioalkyl, C1-C5 alkoxyalkyl, nitro, aminoalkyl, —NR'R", —CH2NR'R"—CONR'R", —COOR'";

Wherein R', R" are independently hydrogen or alkyl, aryl which may have additional substitution;

R' and R" together form a ring with up to six carbon atoms which optionally may be substituted and/or may contain hetero atoms;

R'" is hydrogen or alkyl, aryl which may have additional substitution; Substitutions on ring A together form an additional ring which optionally may be substituted and/or may contain hetero atoms;

Ring B may be further substituted (q) with same or different groups and they are selected from hydrogen, halogen, alkyl, haloalkyl, hydroxyalkyl, thioalkyl, C1-C5 alkoxyalkyl, nitro, aminoalkyl, —NR'R", —CH2NR'R"—CONR'R", —COOR'";

Wherein R', R" are independently hydrogen or alkyl, aryl which may have additional substitution;

R' and R" together form a ring with up to six carbon atoms which optionally may be substituted and/or may contain hetero atoms;

R'" is hydrogen or alkyl, aryl which may have additional substitution; Substitutions on ring B together form an additional ring which optionally may be substituted and/or may contain hetero atoms;

and pharmaceutically acceptable salts thereof.

In preferred embodiment, the present invention provide novel tricyclic compounds of formula (I) and formula (II) are selected from
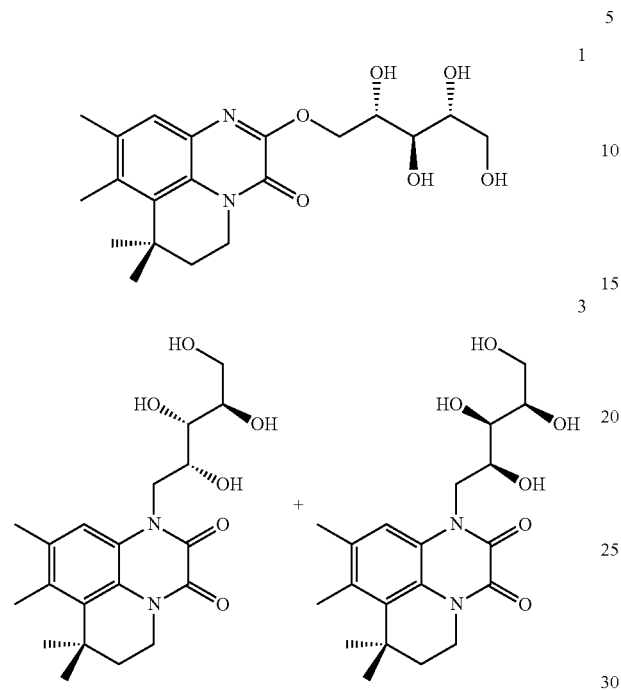
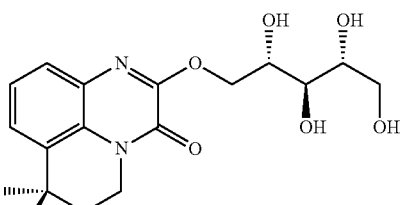
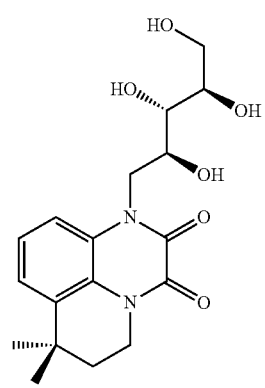
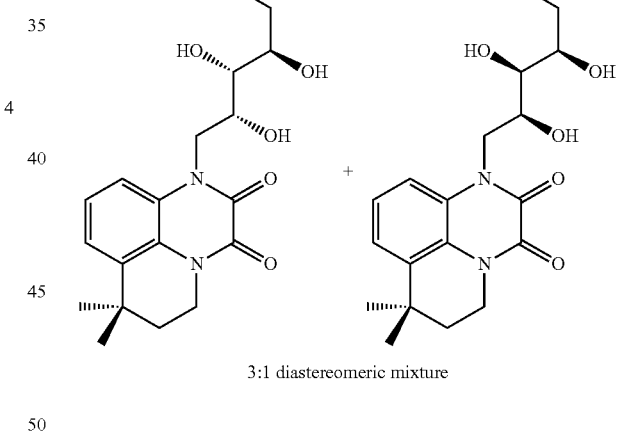
3:1 diastereomeric mixture
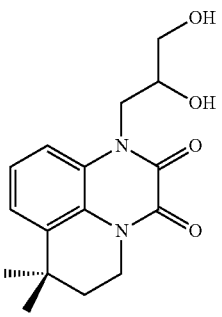

-continued
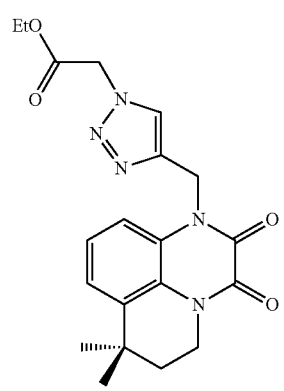
10
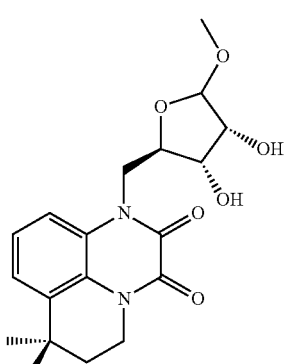
11
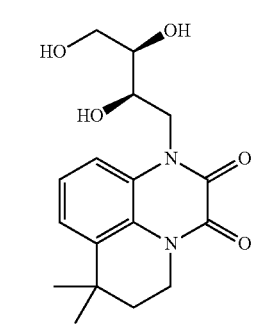
12
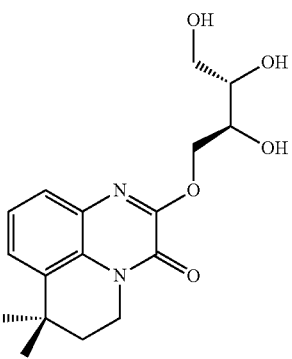
13
-continued
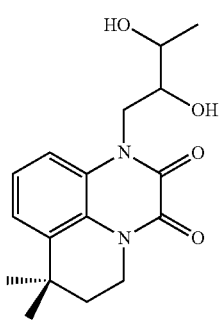
14
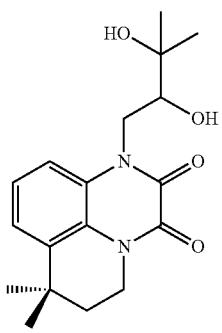
15
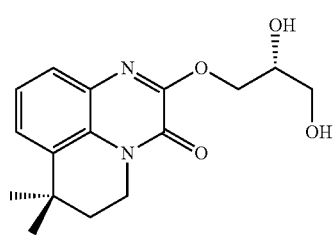
16
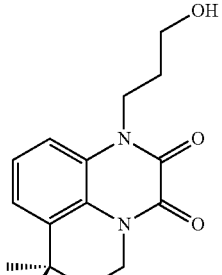
17
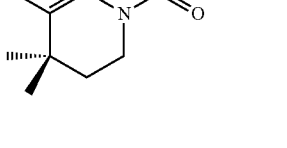
18

19
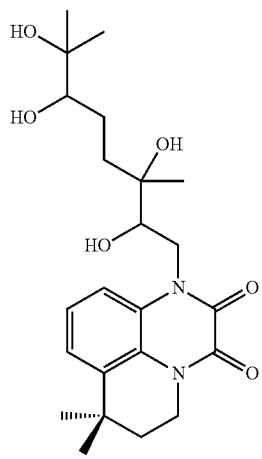
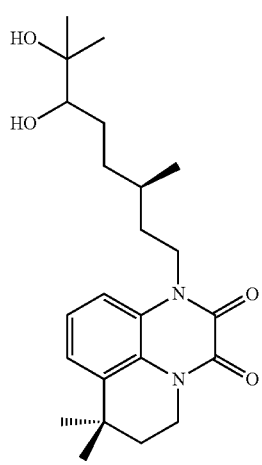
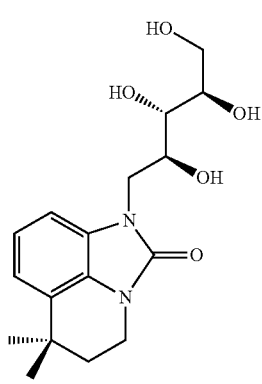
22
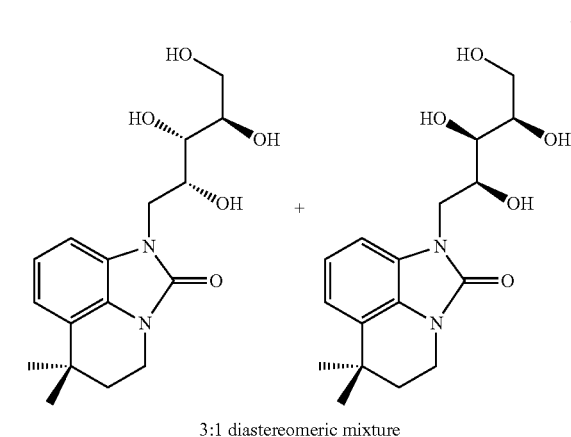
3:1 diastereomeric mixture
23
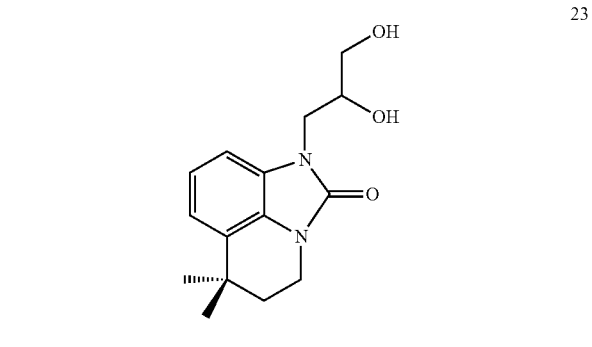
24b
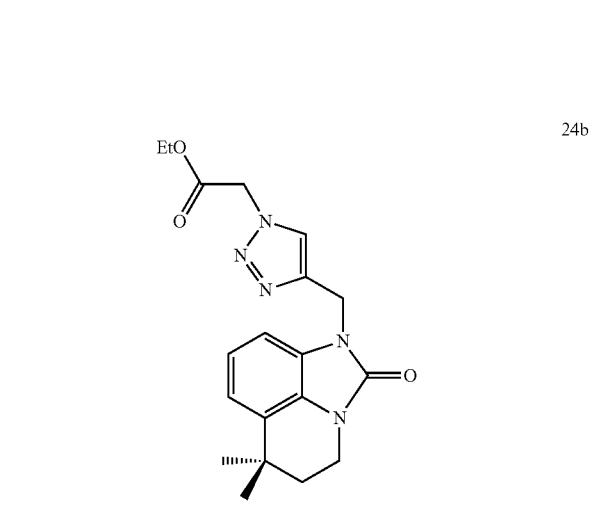
24
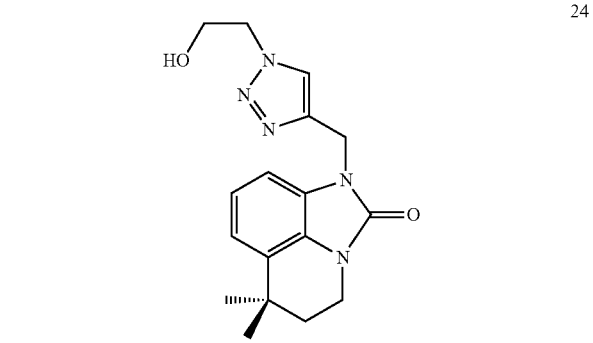

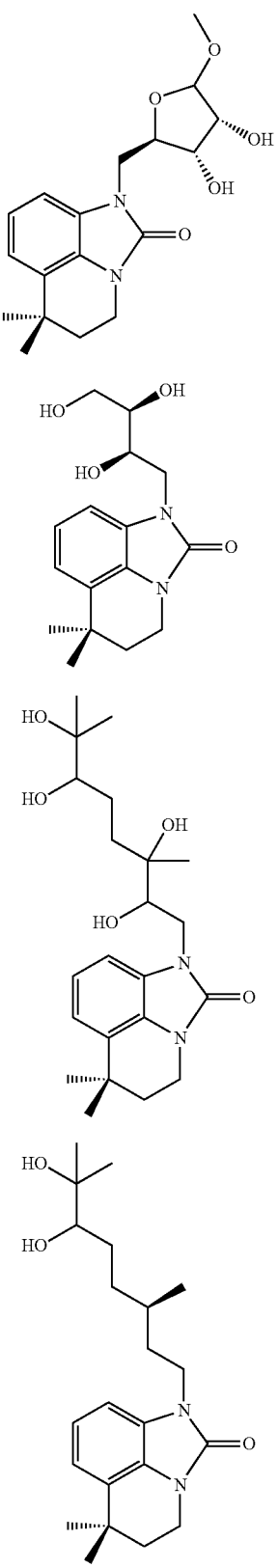

In another embodiment, the present invention provides a process for preparation novel tricyclic compounds formula (I) and formula (II) from 4,5-dimethyl-o-phenylinediamine.

In preferred embodiment, the present invention provides a process for preparation of novel tricyclic compounds of formula (I) and formula (II) from 4,5-dimethyl-1,2-phenylenediamine comprising, building the tricyclic aglycon and attachment of a sugar moiety to the aglycon, which makes the sequence amenable to prepare several analogues using various sugars or sugar mimics. The synthesis began with the monoalkylation using prenyl bromide and $Cs_2CO_3$ base. The intramolecular Friedel Crafts alkylation carried out using $AlCl_3$ in chlorobenzene solvent to obtain tricylic aglycon followed by deprotection. The C—O bond formation with known ribose sugar derivative using triphenylphosphine and diisopropyl azodicarboxylate (DIAD) gives compounds of formula (I) and formula (II).

In another preferred embodiment, the present invention provides a process for the preparation of 7,7,8,9-tetramethyl-2-((2,3,4,5-tetrahydroxypentyl)oxy)-6,7-dihydro-3H, 5H-pyrido[1,2,3-de]quinoxalin-3-one of formula (1) from 4,5-dimethyl-o-phenylinediamine comprising the following steps:

a) refluxing the mixture of 4,5-dimethyl-o-phenylinediamine dissolved in 4N HCL and oxalic acid to obtain 6,7-dimethyl-1,4-dihydroquinoxaline-2,3-dione, b) adding cesium carbonate ($Cs_2CO_3$), 3,3-dimethylallyl bromide to a solution of step (a) in dry DMF followed by stirring at room temperature to obtain mono alkylated and dialkylated 6,7-dimethyl-1-(3-methylbut-2-en-1-yl)-1,4-dihydroquinoxaline-2,3-dione, c) heating the reaction mixture of step (b) and $AlCl_3$ in chlorobenzene up to 120° C. for 12 hrs to obtain 7,7,8,9-tetramethyl-6,7-dihydro-1H,5H-pyrido[1,2,3-de]quinoxaline-2,3-dione, d) adding Triphenylphosphine, ((4S,4'R,5S)-2,2,2',2'-tetramethyl-[4,4'-bi(1,3-dioxolan)]-5-yl)methanol, Diisopropyl azodicarboxylate to a solution of compound of step (c) in dry THF followed by stirring at room temperature to obtain 7,7,8,9-tetramethyl-2-((2,2,2',2'-tetramethyl-[4,4'-bi(1,3-dioxolan)]-5-yl)methoxy)-6,7-dihydro-3H,5H-pyrido[1,2,3-de]quinoxalin-3-one, e) stirring the solution of compound of step (d) in 1 ml of Acetic acid:Water (1:1) at 60° C. to obtain of 7,7,8,9-tetramethyl-2-((2,3,4,5-tetrahydroxypentyl)oxy)-6,7-dihydro-3H,5H-pyrido[1,2,3-de]quinoxalin-3-one.

The process for the preparation of 7,7,8,9-tetramethyl-2-((2,3,4,5-tetrahydroxypentyl)oxy)-6,7-dihydro-3H,5H-pyrido[1,2,3-de]quinoxalin-3-one of formula (1) as described above, stirring in step (b) is carried out for 2 to 4 hours preferably for 3 hours at room temperature.

The process for the preparation of 7,7,8,9-tetramethyl-2-((2,3,4,5-tetrahydroxypentyl)oxy)-6,7-dihydro-3H,5H-pyrido[1,2,3-de]quinoxalin-3-one of formula (1) as described above, wherein stirring in step (d) is carried out for 10 to 12 hours preferably for 12 hours at room temperature.

In another preferred embodiment, the present invention provides a process for preparation hunanamycin A from 4,5-dimethyl-o-phenylinediamine comprising the following steps:

i) refluxing the mixture of 4,5-dimethyl-o-phenylinediamine dissolved in 4N HCL and oxalic acid to obtain 6,7-dimethyl-1,4-dihydroquinoxaline-2,3-dione, ii) adding cesium carbonate ($Cs_2CO_3$), 3,3-dimethylallyl bromide to a solution of step (a) in dry DMF followed by stirring at room temperature to obtain mono alkylated and dialkylated 6,7-dimethyl-1-(3-methylbut-2-en-1-yl)-1,4-dihydro-quinoxaline-2,3-dione, iii) heating the reaction mixture of step (ii) and AlCl₃ in chlorobenzene up to 120° C. for 12 hrs to obtain 7,7,8,9-tetramethyl-6,7-dihydro-1H,5H-pyrido[1,2,3-de]quinoxaline-2,3-dione.

iv) adding the solution of sodium hydride in 1 ml of DMF to a solution of (4) of step (iii) in dry DMF followed by addition of (E)-5-bromopenta-1,3-diene dissolved in dry DMF at 10° C., stirring at room temperature to obtain (E)-7,7,8,9-tetramethyl-1-(penta-2,4-dien-1-yl)-6,7-dihydro-1H,5H-pyrido[1,2,3-de]quinoxaline-2,3-dione, v) stirring a solution of compound of step (iv) in Acetone:tBuOH:Water (7:2:1) followed by addition of 5 ml solution of N-Methylmorpholine N-oxide and osmium tetraoxide in t-BuOH with constant stirring at room temperature to obtain 7,7,8,9-tetramethyl-1-(2,3,4,5-tetrahydroxypentyl)-6,7-dihydro-1H,5H-pyrido[1,2,3-de]quinoxaline-2,3-dione, vi) stirring the solution of compound of step (v) in acetic acid: water for 30 min at 50° C. to obtain racemic Hunanamycin A.

The process for preparation of racemic Hunanamycin A as described above, wherein stirring in step (b) is carried out for 2 to 4 hours preferably for 3 hours at room temperature.

The process for preparation of hunanamycin A as described above, wherein stirring in step (e) is carried out for 10 to 12 hours preferably for 12 hours at room temperature.

In a preferred embodiment, the novel a novel tricyclic compounds of formula (I) and formula (II) are evaluated for anti-microbial activity. The minimum inhibitory concentrations (MICs) is determined using the Promega Bac Titer-Glo microbial cell viability assay. The assays is carried out using *Salmonella enterica* strain AMC (ATCC #6539), Inocula of *S. enterica* prepared from 12-h broth cultures grown in Mueller Hinton broth and the suspensions were then adjusted to a turbidity of 0.5 McFarland. Assays conducted in a 96-well plate using growth media with an inoculum of ~5×10⁴ CFU/mL using the suggested protocols. Bacterial cells were treated with hunanamycin analogs for 24 hours at ranges from 0.4 to 40 μg/mL and ciprofloxacin as a control ranging from 0.03 to 10 μg/mL. The $OD_{600}$ measured using an Envision multi-modal plate reader (Perkin-Elmer, Inc.).

The minimum inhibitory concentrations (MICs) of compounds as listed in table 1.

TABLE 1

| Compound No. | MIC (μg/mL) |
| --- | --- |
| 1 | 8 μg/mL |
| 2 | 8 μg/mL |
| 3 | 8 μg/mL |
| 4 | >16 μg/mL |
| 5 | 4 μg/mL |
| 6 | >16 μg/mL |
| 7 | >16 μg/mL |
| 8 | >16 μg/mL |
| 9 | 8 μg/mL |
| 10 | >16 μg/mL |
| 11 | >16 μg/mL |
| 12 | >16 μg/mL |
| 13 | 16 μg/mL |
| 14 | >16 μg/mL |
| 15 | >16 μg/mL |
| 16 | >16 μg/mL |
| 17 | ND |
| 18 | ND |
| 19 | ND |
| 20 | ND |
| 21 | 4 μg/mL |
| 22 | ND |

TABLE 1-continued

| Compound No. | MIC (μg/mL) |
| --- | --- |
| 23 | >16 μg/mL |
| 24 | >16 μg/mL |
| 24b | 8 μg/mL |
| 25 | 2 μg/mL |
| 26 | >16 μg/mL |
| 27 | ND |
| 28 | ND |

Note:
ND = Not Determined

In another embodiment, a pharmaceutical composition is provided comprising a compound of formula (I) or formula (II), or a stereoisomer, or ester or pharmaceutically acceptable salt thereof, and a pharmaceutically acceptable carrier, diluent or excipient. The pharmaceutical compositions of the invention can be prepared by combining a compound of the invention with an appropriate pharmaceutically acceptable carrier, diluent or excipient, and may be formulated into preparations in solid, semi-solid, liquid or gaseous forms, such as tablets, capsules, powders, granules, ointments, solutions, injections, gels and microspheres, In yet another embodiment, the present invention relates to administering 'an effective amount' of the 'composition of invention' to the subject suffering from said disease. Accordingly, compound of formula I or formula (II) and pharmaceutical compositions containing them may be administered using any amount, any form of pharmaceutical composition via any route of administration effective for treating the disease. Typical routes of administering such pharmaceutical compositions include, without limitation, oral, topical, transdermal, inhalation, parenteral, sublingual, buccal, rectal, vaginal, and intranasal.

Pharmaceutical compositions of the invention are formulated so as to allow the active ingredients contained therein to be bioavailable upon administration of the composition to a patient. Compositions that will be administered to a subject or patient may take the form of one or more dosage units. The dosage forms can also be prepared as sustained, controlled, modified and immediate dosage forms.

The following examples, which include preferred embodiments, will serve to illustrate the practice of this invention, it being understood that the particulars shown are by way of example and for purpose of illustrative discussion of preferred embodiments of the invention.

Following examples are given by way of illustration therefore should not be construed to limit the scope of the invention.

Examples 1

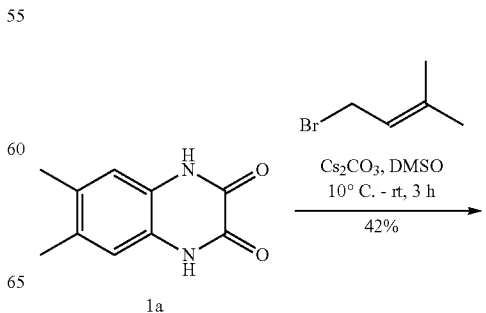

1a

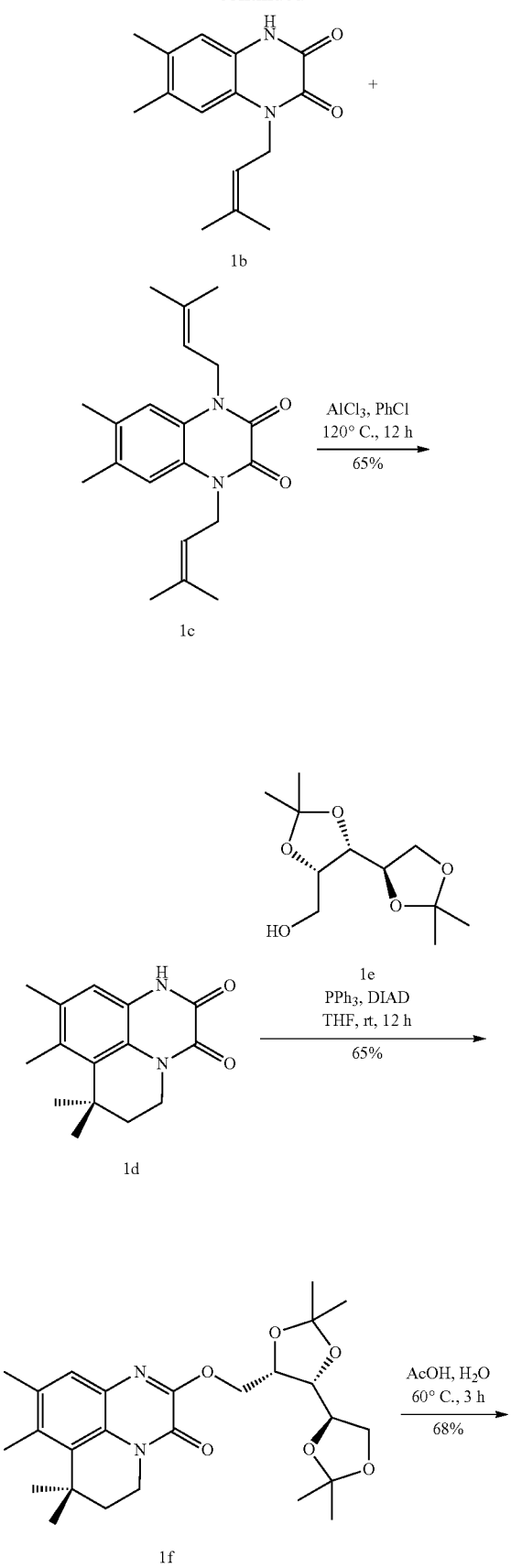

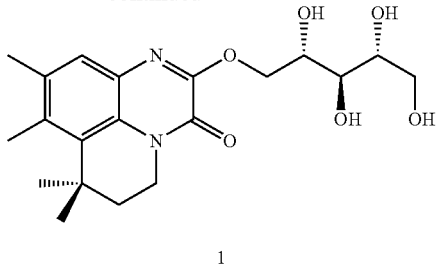

Example 1(a): Synthesis of 6,7-dimethyl-1-(3-methylbut-2-en-1-yl)-1,4-dihydro-quinoxaline-2,3-dione (1b)

To a solution of 6,7-dimethyl-1,4-dihydroquinoxaline-2,3-dione reaction 1a (600 mg, 3.15 mmol) in dry DMSO (60 mL) was added caesium carbonate (1.53 g, 4.73 mmol), followed by 3,3-dimethylallyl bromide (0.363 mL, 3.15 mmol) diluted in 5 mL of DMSO and kept stirring for 3 hrs at room temperature reaction. The reaction mixture was added to cold water and extracted with ethyl acetate (3×100 mL). The combined organic layer was washed with brine and dried over $Na_2SO_4$, concentrated under reduced pressure, and subjected to flash chromatography over silica gel (60% EtOAc: petroleum ether) to afford mono-alkylated compound 1b (342 mg, 42%) as brown solid.

Data for 1b: M.P. 271° C.; $^1$H NMR (200 MHz, $CDCl_3$) δ 1.73 (s, 3H), 1.90 (s, 3H), 2.28 (s, 3H) 2.31 (s, 3H), 4.84 (d, J=6.8 Hz, 2H), 5.2 (t, J=6.8 Hz, 1H), 6.95 (s, 1H), 7.12 (s 1H), 11.48 (s, 1H); $^{13}$C NMR (50 MHz, $CDCl_3$) δ 18.5, 19.1, 20.1, 25.8, 41.7, 115.9, 117.5, 117.8, 122.5, 124.5, 133.3, 135.3, 137.4, 155.1, 155.6; IR (Neat) v/cm$^{-1}$: 1452, 1600, 1626, 1694, 2854, 2952, 3353; HRMS (ESI): m/z calculated for $C_{15}H_{18}O_2N_2$ [M+Na]$^+$ 281.1260. found 281.1258.

Dialkylated product (1c) (55 mg, 6%) as brown solid.

Data for 1c: M.P. 255° C.; $^1$H NMR (400 MHz, $CDCl_3$) δ 1.71 (s, 6H), 1.88 (s, 6H), 2.30 (s, 6H), 4.79 (t, J=6.2 Hz, 4H), 5.15 (d, J=6.2 Hz, 2H), 6.96 (s, 2H); $^{13}$C NMR (100 MHz, $CDCl_3$) δ 18.4, 19.3, 25.7, 41.45, 116.3, 117.9, 124.5, 132.5, 137.2, 154.1; IR ($CHCl_3$) v/cm$^{-1}$: 1223, 1377, 1461, 1678, 2855, 2926, 3178, 3393; HRMS (ESI): m/z calculated for $C_{20}H_{26}O_2N_2$ [M+Na]$^+$ 326.1994. found 326.1987.

Example 1(b): Synthesis of 7,7,8,9-tetramethyl-6,7-dihydro-1H,5H-pyrido[1,2,3-de]quinoxaline-2,3-dione (1d)

A dried sealed tube charged with 6,7-dimethyl-1-(3-methylbut-2-en-1-yl)-1,4-dihydroquinoxaline-2,3-dione 1b (200 mg, 0.775 mmol) and $AlCl_3$ (613 mg, 4.65 mmol) in chlorobenzene (10 mL) was heated up to 120° C. for 12 hrs. The reaction was quenched by the addition of $H_2O$ (20 mL), then neutralized with saturated aqueous $NaHCO_3$. The reaction mixture was filtered through a pad of Celite® and washed with ethyl acetate. The resulting filtrate was partitioned with ethyl acetate (3×100 mL) and water. The combined organic layers were dried over $Na_2SO_4$, concentrated in vacuo and purified by flash column chromatography over silica gel (30% EtOAc: $CH_2Cl_2$) to afford compound 1d (130 mg, 65%) as brown solid.

Data for 1d: M.P. 205° C.; $^1$H NMR (400 MHz, $CDCl_3$) δ 1.52 (s, 6H), 1.91 (m, 2H), 2.28 (s, 3H), 2.40 (s, 3H), 4.17

(m, 2H), 7.11 (s, 1H), 11.97 (s, 1H); $^{13}$C NMR (100 MHz, CDCl$_3$) δ 19.0, 20.7, 28.6 (2C), 32.9, 38.1, 39.7, 116.4, 121.7, 122.5, 132.2, 132.4, 134.9, 154.6, 155.5; IR (CHCl$_3$) v/cm$^{-1}$: 1377, 1462, 1680, 1662, 2251, 2855, 2929; HRMS (ESI): m/z calculated for C$_{15}$H$_{18}$O$_2$N$_2$ [M+Na]$^+$ 281.1260. found 281.1258.

Example 1(c): Synthesis of 7,7,8,9-tetramethyl-2-(((4S,4'R,5S)-2,2,2',2'-tetramethyl-[4,4'-bi(1,3-dioxolan)]-5-yl)methoxy)-6,7-dihydro-3H,5H-pyrido[1,2,3-de]quinoxalin-3-one (1f)

To a solution of 7,7,8,9-tetramethyl-6,7-dihydro-1H,5H-pyrido[1,2,3-de]quinoxaline-2,3-dione 1d (130 mg, 0.50 mmol) in dry THF (3 mL) was added triphenylphosphine (303 mg, 1.15 mmol), ((4S,4'R,5S)-2,2,2',2'-tetramethyl-[4,4'-bi(1,3-dioxolan)]-5-yl)methanol 1e (140 mg, 0.60 mmol) and DIAD (0.225 mL, 1.15 mmol) sequentially and stirred for 12 hrs at room temperature. The reaction mixture was diluted with water (5 mL) and extracted with ethyl acetate (3×10 mL), and the organic layer was washed successively with water and brine, dried over Na$_2$SO$_4$, and concentrated in vacuo. The residue was purified by flash silica gel column chromatography (40% EtOAc: CH$_2$Cl$_2$) to afford O-alkylated product 1f (155 mg, 65%) as brown coloured oil.

Data for 1f: [α]$_D^{25}$=−6.1° (c 5.2, CHCl3); $^1$H NMR (400 MHz, CD$_3$Cl$_3$) δ 1.25 (s, 3H), 1.35 (s, 3H), 1.35 (s, 3H), 1.43 (s, 3H), 1.53 (s, 6H), 1.93 (t, J=5.9 Hz, 2H), 2.31 (s, 3H), 2.48 (s, 3H), 3.90 (dd, J=8.2, 5.5 Hz, 1H), 4.13 (m, 4H), 4.21 (m, 1H), 4.54-4.59 (m, 1H), 4.68-4.69 (m, 1H), 4.74-4.79 (m, 1H), 7.30 (s, 1H); $^{13}$C NMR (100 MHz, CD$_3$Cl$_3$) δ 19.3, 20.7, 25.2 (2C), 26.6, 27.7, 28.5, 33.4, 38.5, 40.4, 47.9, 66.1, 68.4, 74.4, 76.3, 78.8, 110.0, 110.5, 126.6, 127.1, 130.0, 132.3, 135.4, 136.0, 151.0, 153.0; IR (CHCl$_3$) v/cm$^{-1}$: 1067, 1371, 1618, 1630, 2934, 2985; HRMS (ESI): m/z calculated for C$_{26}$H$_{36}$O$_6$N$_2$ [M+Na]$^+$ 495.2466. found 495.2463.

Example 1: Synthesis of 7,7,8,9-tetramethyl-2-(((2S,3R,4R)-2,3,4,5-tetrahydroxy-pentyl)oxy)-6,7-dihydro-3H,5H-pyrido[1,2,3-de]quinoxalin-3-one (1)

A solution of 7,7,8,9-tetramethyl-2-(((4S,4'R,5S)-2,2,2',2'-tetramethyl-[4,4'-bi(1,3-dioxolan)]-5-yl)methoxy)-6,7-dihydro-3H,5H-pyrido[1,2,3-de]quinoxalin-3-one 1f (50 mg, 0.10 mmol) in acetic acid:water (1:1; 1 mL) was stirred for 3 hrs at 60° C. The reaction mixture was concentrated under reduced pressure, and purified by flash column chromatography (10% MeOH: CH$_2$Cl$_2$) to give compound 6 (28 mg, 68%) as colourless sticky solid.

Data for 1: [α]$_D^{25}$=+5.7° (c 1.4, MeOH); $^1$H NMR (500 MHz, CD$_3$OD) δ 1.53 (s, 6H), 1.93 (t, J=5.8 Hz, 2H), 2.31 (s, 3H), 2.48 (s, 3H), 3.67-3.71 (m, 1H), 3.75-3.78 (m, 1H), 3.79-3.84 (m, 2H), 4.15-4.18 (m, 3H), 4.45 (dd, J=11.2, 7.0 Hz, 1H), 4.65 (dd, J=11.2, 2.7 Hz, 1H), 7.30 (s, 1H); $^{13}$C NMR (125 MHz, CD$_3$OD) δ 19.7, 21.1, 28.9, 33.8 (2C), 39.0, 40.8, 64.5, 70.1, 71.9, 73.8, 74.1, 126.9, 127.5, 130.6, 132.8, 136.0, 151.9, 153.6; IR (CHCl$_3$) v/cm$^{-1}$: 1035, 1066, 1299, 1614, 1646, 2924, 3366; HRMS (ESI): m/z calculated for C$_{20}$H$_{28}$O$_6$N$_2$ [M+Na]$^+$ 415.1840. found 415.1836.

Example 2

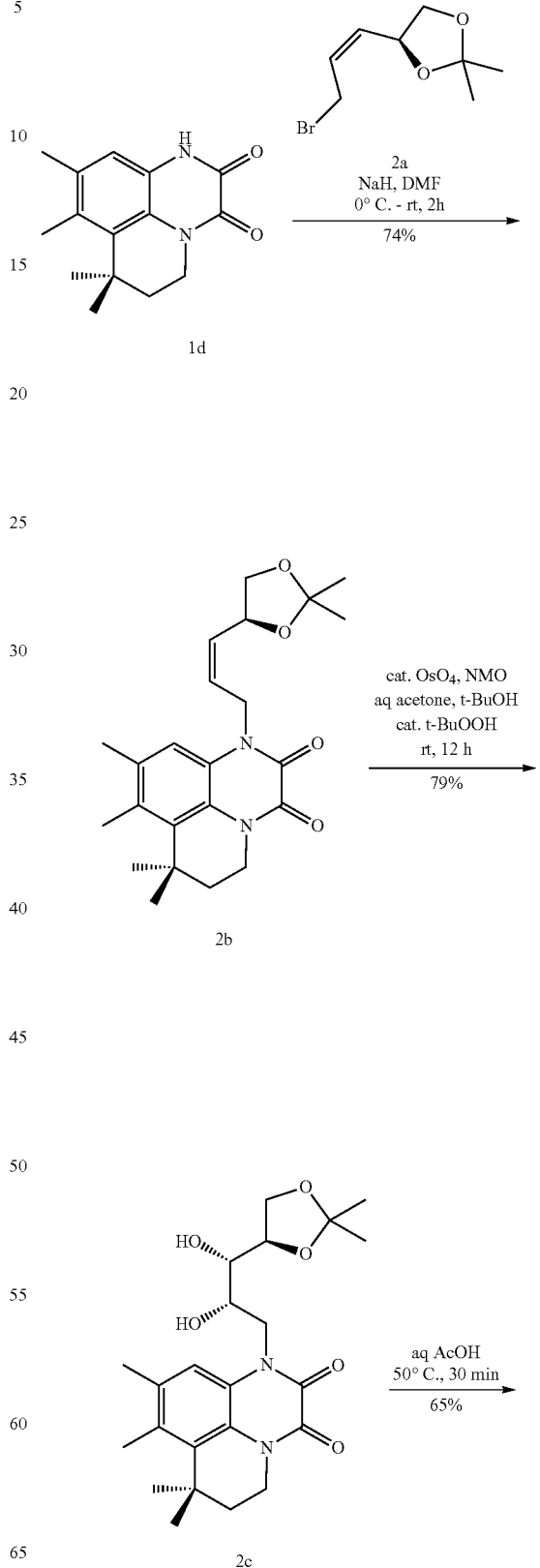

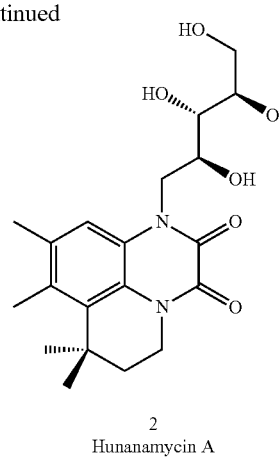

2
Hunanamycin A

Example 2(a): Synthesis of (S,Z)-1-(3-(2,2-dimethyl-1,3-dioxolan-4-yl)allyl)-7,7,8,9-tetramethyl-6,7-dihydro-1H,5H-pyrido[1,2,3-de]quinoxaline-2,3-dione (2b)

A solution of 7,7,8,9-tetramethyl-6,7-dihydro-1H,5H-pyrido[1,2,3-de]quinoxaline-2,3-dione 1d (70 mg, 0.27 mmol) in dry DMF (1 mL) was added drop wise to pre-cooled (0° C.) suspension of sodium hydride (60% dispersion in mineral oil, 27 mg, 0.67 mmol) in 2 mL of DMF. The reaction mixture was allowed to warm to room temperature and stirred for 20 mins. (S,Z)-4-(3-bromoprop-1-en-1-yl)-2,2-dimethyl-1,3-dioxolane 2a (119 mg, 0.54 mmol), dissolved in dry DMF, was then added drop wise at 0° C. and stirred for 2 hrs at room temperature. The reaction mixture was added to cold water (10 mL) and extracted with ethyl acetate (3×10 mL) and the combined organic layers were washed with water, brine, then dried over $Na_2SO_4$, filtered and concentrated in vacuo, and purified by column chromatography (30% EtOAc: $CH_2Cl_2$) to afford compound 2b (80 mg, 74%) as colourless oil.

Data for 2b: $[\alpha]_D^{25}$=+11° (c 1.1, $CHCl_3$); $^1H$ NMR (400 MHz, $CDCl_3$) δ 1.46 (s, 3H), 1.47 (s, 3H), 1.53 (s, 6H), 1.90 (t, J=5.2 Hz, 2H), 2.32 (s, 3H), 2.42 (s, 3H), 3.66 (t, J=7.5 Hz, 1H), 4.13-4.16 (m, 2H), 4.26 (dd, J=8.1, 6.1 Hz, 1H), 4.73 (dd, J=15.7, 6.7 Hz, 1H), 5.12 (q, J=7.2 Hz, 1H), 5.25-5.30 (m, 1H), 5.59-5.64 (m, 1H), 5.68-5.74 (m, 1H), 7.03 (s, 1H); $^{13}C$ NMR (100 MHz, $CDCl_3$) δ 19.0, 21.4, 25.8, 26.7, 28.6, 28.7, 33.2, 37.9, 39.6, 40.8, 69.4, 71.9, 109.6, 114.7, 121.9, 124.2, 127.5, 131.6, 132.1, 132.9, 134.3, 153.4, 153.5; IR ($CHCl_3$) ν/cm$^{-1}$: 1215, 1677, 1745, 2400, 2925, 3020; HRMS (ESI): m/z calculated for $C_{23}H_{30}O_4N_2$ [M+Na]$^+$ 421.2098. found 421.2091.

Example 2(b): Synthesis of 1-((2S,3S)-3-((R)-2,2-dimethyl-1,3-dioxolan-4-yl)-2,3-dihydroxypropyl)-7,7,8,9-tetramethyl-6,7-dihydro-1H,5H-pyrido[1,2,3-de]quinoxaline-2,3-dione (2c)

A solution of (S,Z)-1-(3-(2,2-dimethyl-1,3-dioxolan-4-yl)allyl)-7,7,8,9-tetramethyl-6,7-dihydro-1H,5H-pyrido[1,2,3-de]quinoxaline-2,3-dione 2b (80 mg, 0.20 mmol) in acetone:water:t-BuOH (5 mL, 7:2:1) was treated with NMO (94 mg, 1.30 mmol), osmium tetraoxide (2.5% sol. in t-BuOH) (0.4 mL, 0.040 mmol) and cat. t-BuOOH and stirred for 12 hrs at room temperature. The reaction mixture was added to cold solution of $NaHSO_4$ and extracted with ethyl acetate (3×30 mL) and washed with water, brine and the combined organic layers were dried over $Na_2SO_4$, filtered and concentrated in vacuo. The resultant residue was purified by flash chromatography on silica (5% MeOH: $CH_2Cl_2$) to afford hydroxylated compound 2c (68 mg, 79%) as colourless oil.

Data for 2c: $[\alpha]_D^{25}$=−57° (c 0.7, $CHCl_3$); $^1H$ NMR (400 MHz, $CDCl_3$) δ 1.38 (s, 3H), 1.39 (s, 3H), 1.5 (s, 6H), 1.87 (t, J=5.2 Hz, 2H), 2.30 (s, 3H), 2.40 (s, 3H), 3.77 (br. s., 1H), 4.05-4.25 (m, 8H), 4.73 (br. s., 1H), 4.92 (dd, J=14.3, 7.7 Hz, 1H), 7.35 (s, 1H); $^{13}C$ NMR (100 MHz, $CDCl_3$) δ 19.0, 21.4, 25.3, 26.7, 28.6 (2C), 33.2, 38.0, 39.5, 45.4, 68.0, 71.8, 73.7, 76.7, 109.6, 115.8, 122.0, 124.7, 132.4, 132.6, 134.4, 153.4, 155.6; IR ($CHCl_3$) ν/cm$^{-1}$: 1062, 1217, 1674, 2925, 3429; HRMS (ESI): m/z calculated for $C_{23}H_{32}O_6N_2$ [M+Na]$^+$ 455.2153. found 455.2143.

Example 2: Synthesis of Hunanamycin A

A solution of 1-((2S,3S)-3-((R)-2,2-dimethyl-1,3-dioxolan-4-yl)-2,3-dihydroxypropyl)-7,7,8,9-tetramethyl-6,7-dihydro-1H,5H-pyrido[1,2,3-de]quinoxaline-2,3-dione 2c (68 mg, 0.15 mmol) in acetic acid:water (1:1; 1 mL) was stirred for 30 min at 50° C. The reaction mixture was then concentrated in vacuo, and purified by flash chromatography on $SiO_2$ (10% MeOH: $CH_2Cl_2$) to afford compound 2 (Hunanamycin A) (45 mg, 66%) as yellow solid.

Data for 2 (Hunanamycin A): $[\alpha]_D^{25}$=+15° (c 0.4, MeOH); $^1H$ NMR (500 MHz, MeOD-$d_4$) δ 1.55 (s, 6H), 1.94 (t, J=5.9 Hz, 2H), 2.34 (s, 3H), 2.46 (s, 3H), 3.63-3.71 (m, 1H), 3.74-3.84 (m, 3H), 4.08-4.19 (m, 2H), 4.20-4.32 (m, 2H), 4.77-4.81 (m, 1H), 7.46 (s, 1H); $^{13}C$ NMR (125 MHz, MeOD-$d_4$) δ 19.6, 21.6, 29.0, 29.4, 34.5, 39.4, 40.8, 46.7, 65.0, 71.0, 74.4, 75.1, 117.2, 123.4, 126.3, 133.8, 134.3, 136.1, 155.4, 156.7; IR ($CHCl_3$) δ/cm$^{-1}$: 1038, 1224, 1424, 1669, 2865, 2925, 3428; HRMS (ESI): m/z calculated for $C_{20}H_{28}O_6N_2$ [M+Na]$^+$ 415.1840. found 415.1832.

Example 3

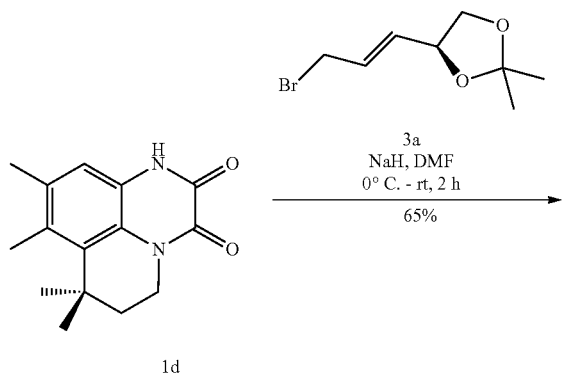

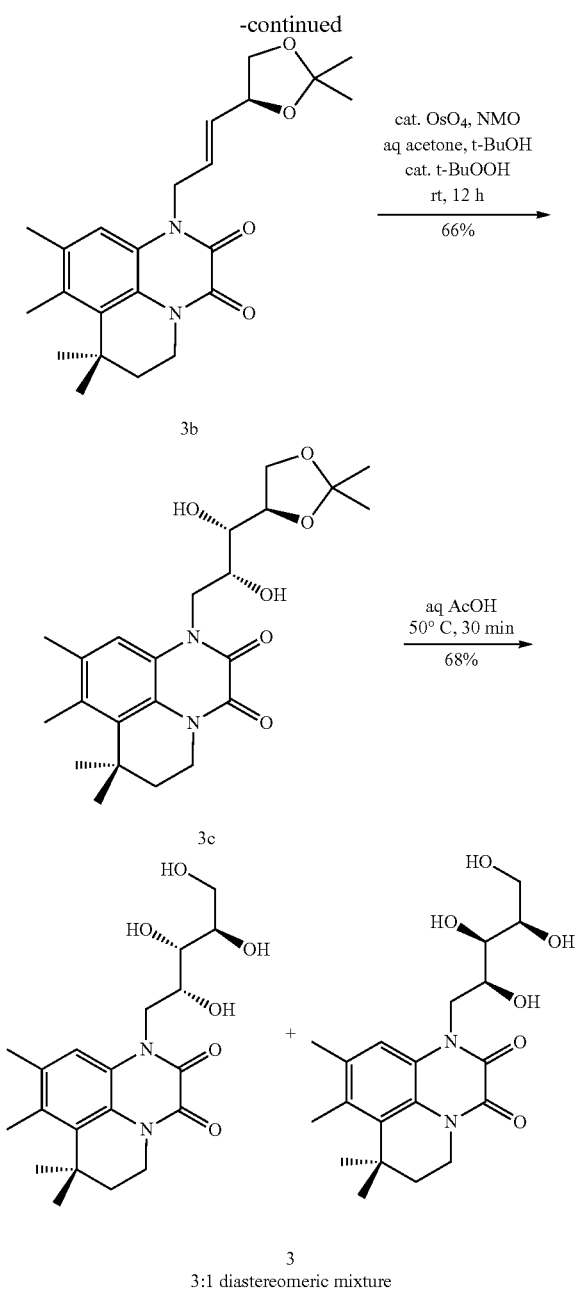

3b

3c 3
3:1 diastereomeric mixture cat. OsO4, NMO
aq acetone, t-BuOH
cat. t-BuOOH
rt, 12 h
66% aq AcOH
50° C, 30 min
68%

Example 3(a): Synthesis of (S,E)-1-(3-(2,2-dimethyl-1,3-dioxolan-4-yl)allyl)-7,7,8,9-tetramethyl-6,7-dihydro-1H,5H-pyrido[1,2,3-de]quinoxaline-2,3-dione (3b)

A solution of 7,7,8,9-tetramethyl-6,7-dihydro-1H,5H-pyrido[1,2,3-de]quinoxaline-2,3-dione 1d (60 mg, 0.23 mmol) in dry DMF (1 mL) was added dropwise to precooled suspension of sodium hydride (60% dispersion in mineral oil, 23 mg, 0.58 mmol) in 1 mL of DMF. The cooling bath was then removed, and the flask was allowed to warm to room temperature and stirred for 20 mins. (S,E)-4-(3-bromoprop-1-en-1-yl)-2,2-dimethyl-1,3-dioxolane 3a (113 mg, 0.51 mmol), dissolved in dry DMF, was added drop wise at 0° C. and stirred for 2 hrs at room temperature, then reaction mixture was added to cold water and extracted with ethyl acetate (3×10 mL). The combined organics were dried over Na$_2$SO$_4$, filtered and concentrated in vacuo. The resultant residue was purified by flash chromatography on SiO2 (30% EtOAc: CH$_2$Cl$_2$) to afford compound 3b (52 mg, 65%) as brown gummy mass.

Data for 3b: $[\alpha]_D^{25}$=+12.5° (c=0.8, CHCl$_3$); $^1$H NMR (400 MHz, CDCl$_3$) δ 1.36 (s, 3H), 1.39 (s, 3H), 1.53 (s, 6H), 1.90 (t, J=5.7 Hz, 2H), 2.30 (s, 3H), 2.42 (s, 3H), 3.56 (t, J=7.7 Hz, 1H), 4.06 (dd, J=8.2, 6.2 Hz, 1H), 4.14-4.16 (m, 2H), 4.50 (q, J=6.7 Hz, 1H), 4.85 (t, J=5.0 Hz, 2H), 5.72 (dd, J=15.6, 6.6 Hz, 1H), 5.85-5.92 (m, 1H), 6.92 (s, 1H); $^{13}$C NMR (100 MHz, CDCl$_3$) δ 19.0, 21.6, 25.8, 26.6, 28.7, 29.6, 33.2, 37.9, 39.6, 44.2, 69.2, 76.0, 109.4, 114.9, 121.9, 124.3, 126.0, 131.7, 132.0, 132.8, 134.1, 153.4, 153.5; IR (CHCl$_3$) ν/cm$^{-1}$: 757, 1215, 1677, 1745, 2400, 2925, 3020; HRMS (ESI): m/z calculated for C$_{23}$H$_{30}$O$_4$N$_2$ [M+Na]$^+$ 421.2098. found 421.2089.

Example 3(b): Synthesis of 1-((2R,3S)-3-((R)-2,2-dimethyl-1,3-dioxolan-4-yl)-2,3-dihydroxypropyl)-7,7,8,9-tetramethyl-6,7-dihydro-1H,5H-pyrido[1,2,3-de]quinoxaline-2,3-dione (3c)

A solution of (S,E)-1-(3-(2,2-dimethyl-1,3-dioxolan-4-yl)allyl)-7,7,8,9-tetramethyl-6,7-dihydro-1H,5H-pyrido[1,2,3-de]quinoxaline-2,3-dione 3b (50 mg, 0.12 mmol) in acetone:water:t-BuOH (2 mL, 7:2:1) was treated with NMO (58 mg, 0.502 mmol), osmium tetraoxide (2.5% sol. in t-BuOH) (0.255 mL, 0.0251 mmol) and cat. t-BuOOH at room temperature and stirred for 12 hrs. The reaction mixture was added to cold sol of NaHSO$_4$ and extracted with ethyl acetate (3×10 mL) and washed with water, brine. The combined organics were dried over Na$_2$SO$_4$, filtered and concentrated in vacuo. The resultant residue was purified by flash chromatography on SiO$_2$ (5% MeOH: CH$_2$Cl$_2$) to afford compound 3c (32 mg, 66%, 3:1 inseparable diastereomers) as yellow sticky solid.

Data for 3c: $^1$H NMR (400 MHz, CDCl$_3$) δ 1.27 (s, 3H), 1.32 (s, 3H), 1.53 (s, 6H), 1.91 (t, J=6.2 Hz, 2H), 2.33 (s, 3H), 2.44 (s, 3H), 3.41 (d, J=7.7 Hz, 1H), 3.95-4.01 (m, 1H), 4.01-4.32 (m, 8H), 4.49-4.55 (m, 1H), 7.15 (s, 1H); $^{13}$C NMR (100 MHz, CDCl$_3$) δ 19.1, 21.6, 25.2, 26.7, 28.6, 28.7, 33.3, 38.1, 39.6, 46.4, 67.5, 68.3, 71.6, 75.1, 109.2, 114.8, 122.1, 124.2, 132.9, 133.1, 134.7, 153.1, 155.4; IR (CHCl$_3$) ν/cm$^{-1}$: 770, 1216, 1675, 2925, 3429; HRMS (ESI): m/z calculated for C$_{23}$H$_{32}$O$_6$N$_2$ [M+Na]$^+$455.2153. found 455.2143.

Note: Minor peaks in NMR ($^1$H and $^{13}$C) which could not be cleanly distinguished, corresponds to other diastereomer.

Example 3: Synthesis of 7,7,8,9-tetramethyl-1-((2R,3S,4R)-2,3,4,5-tetrahydroxy-pentyl)-6,7-dihydro-1H,5H-pyrido[1,2,3-de]quinoxaline-2,3-dione (3)

A solution of 1-((2R,3S)-3-((R)-2,2-dimethyl-1,3-dioxolan-4-yl)-2,3-dihydroxypropyl)-7,7,8,9-tetramethyl-6,7-dihydro-1H,5H-pyrido[1,2,3-de]quinoxaline-2,3-dione 3c (25 mg, 0.057 mmol) in Acetic acid:Water (1:1) 1 mL and kept stirring for 3 h at 60° C. reaction was monitored by TLC. The reaction mixture concentrated under reduced pressure, and purified by column chromatography (10% MeOH: CH$_2$Cl$_2$) to afford compound 13 (15 mg, 68%, 3:1 inseparable diastereomers) as colourless gum.

Data for 3: $^1$H NMR (500 MHz, MeOD-d$_4$) δ1.54 (s, 6H), 1.93 (t, J=5.8 Hz, 2H), 2.35 (s, 3H), 2.46 (s, 3H), 3.48 (d, J=8.5 Hz, 1H), 3.59-3.76 (m, 2H), 3.76-3.85 (m, 1H), 4.08-4.20 (m, 2H), 4.29-4.58 (m, 3H), 7.39 and 7.43 (s, 1H);

$^{13}$C NMR (125 MHz, MeOD-d$_4$) δ 19.6, 21.7, 29.1, 29.3, 34.5, 39.4, 40.8, 47.5, 65.2, 68.6, 72.6, 72.7, 117.0, 123.4, 126.4, 133.9, 134.4, 136.2, 155.3, 156.5; IR (CHCl$_3$) v/cm$^{-1}$: 754, 1036, 1404, 1668, 2925, 3363; HRMS (ESI): m/z calculated for C$_{20}$H$_{28}$O$_6$N$_2$ [M+Na]$^+$ 415.1840. found 415.1833.

Note: Minor peaks in NMR ($^1$H and $^{13}$C) which could not be cleanly distinguished, corresponds to other diastereomer Example 4

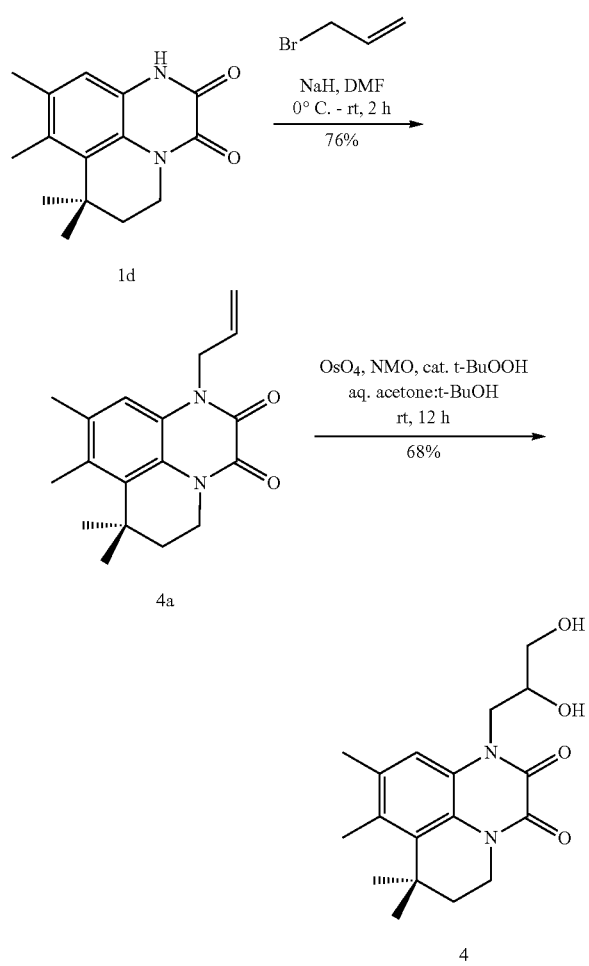

Example 4(a): Synthesis of 1-Allyl-7,7,8,9-tetramethyl-6,7-dihydro-1H,5H-pyrido[1,2,3-de]quinoxaline-2,3-dione (4a)

A solution of 7,7,8,9-tetramethyl-6,7-dihydro-1H,5H-pyrido[1,2,3-de]quinoxaline-2,3-dione 1d (30 mg, 0.11 mmol) in dry DMF (1 mL) was added drop wise to a pre-cooled suspension of sodium hydride (60% dispersion in mineral oil, 9.2 mg, 0.23 mmol) in 1 mL of DMF. Then cooling bath was removed, and the flask was allowed to warm to room temperature and stirred for 20 mins. Allyl bromide (12 µl, 0.139 mmol) was then added drop wise at 0° C. and stirred for 2 h at room temperature. The reaction was quenched by the addition of H$_2$O (5 mL) and extracted with ethyl acetate (3×10 mL). The combined organics were dried over Na$_2$SO$_4$, filtered and concentrated in vacuo. The resultant residue was purified by flash chromatography on SiO$_2$ (30% EtOAc: CH$_2$Cl$_2$) to afford compound 4a (26 mg, 76%) as colourless oil.

Data for 4a: $^1$H NMR (500 MHz, CDCl$_3$) δ 1.53 (s, 6H), 1.90 (t, J=6.1 Hz, 2H), 2.30 (s, 3H), 2.42 (s, 3H), 4.16 (t, J=5.8 Hz, 2H), 4.80-4.90 (m, 2H), 5.21-5.28 (m, 2H), 5.90-5.95 (m, 1H), 6.94 (s, 1H); $^{13}$C NMR (125 MHz, CDCl$_3$) δ 19.1, 21.6, 28.7 (2C), 33.3, 38.0, 39.7, 45.5, 115.2, 118.0, 121.9, 124.4, 130.8, 132.0, 132.8, 134.1, 153.5, 153.56; IR (CHCl$_3$) v/cm$^{-1}$: 1462, 1680, 1662, 2875, 2925; HRMS (ESI): m/z calculated for C$_{18}$H$_{22}$O$_2$N$_2$ [M+Na]$^+$ 321.1579. found 321.1577.

Example 4: Synthesis of 1-(2,3-dihydroxypropyl)-7,7,8,9-tetramethyl-6,7-dihydro-1H,5H-pyrido[1,2,3-de]quinoxaline-2,3-dione (4)

A solution of 1-allyl-7,7,8,9-tetramethyl-6,7-dihydro-1H,5H-pyrido[1,2,3-de]quinoxaline-2,3-dione 4a (20 mg, 0.067 mmol) in acetone:water:t-BuOH (2 mL, 7:2:1) was treated with NMO (31 mg, 0.268 mmol), osmium tetraoxide (2.5% sol. in $^t$BuOH) (0.136 mL, 0.013 mmol) and cat. T-BuOOH$^4$ and stirred for 12 h at room temperature. The reaction mixture was quenched with ice cold solution of NaHSO$_4$ (2 mL) and extracted with ethyl acetate (3×5 mL) and washed with water and brine. The combined organic layer were dried over Na$_2$SO$_4$, filtered and concentrated in vacuo, and purified by column chromatography (10% MeOH: CH$_2$Cl$_2$) to afford compound 4 (15 mg, 68%) as colourless oil.

Data for 4: $^1$H NMR (400 MHz, MeOD-d$_4$) δ 1.54 (s, 3H), 1.55 (s, 3H), 1.92 (t, J=6.4 Hz, 2H), 2.34 (s, 3H), 2.45 (s, 3H), 3.63 (d, J=5.5 Hz, 2H), 4.03-4.13 (m, 3H), 4.29-4.40 (m, 2H), 7.35 (s, 1H); $^{13}$C NMR (100 MHz, MeOD-d$_4$) δ 19.5, 21.5, 28.9, 29.1, 34.3, 39.1, 40.6, 47.2, 65.2, 70.6, 116.7, 123.2, 126.2, 133.7, 134.1, 135.8, 155.0, 156.1; IR (CHCl$_3$) v/cm$^{-1}$: 1398, 1595, 1668, 2855, 2924, 3418; HRMS (ESI): m/z calculated for C$_{18}$H$_{24}$O$_4$N$_2$ [M+H]$^+$ 333.1809. found 333.1802.

Example 5

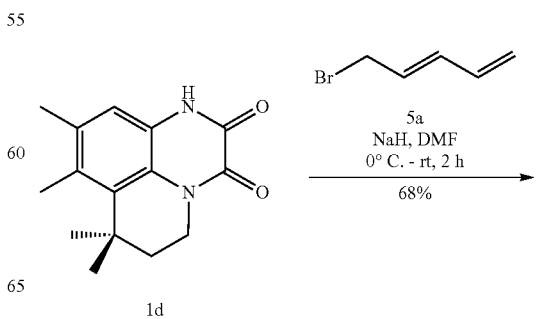

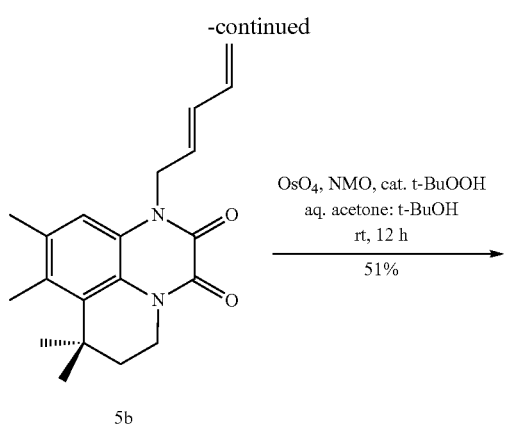

Example 5(a): Synthesis of (E)-7,7,8,9-tetramethyl-1-(penta-2,4-dien-1-yl)-6,7-dihydro-1H,5H pyrido[1,2,3-de]quinoxaline-2,3-dione (5b)

A solution of 7,7,8,9-tetramethyl-6,7-dihydro-1H,5H-pyrido[1,2,3-de]quinoxaline-2,3-dione 1d (100 mg, 0.3876 mmol) in dry DMF (5 mL) was added drop wise to a suspension of Sodium hydride (60% dispersion in mineral oil, 38 mg, 0.969 mmol) 1 ml of DMF at 0° C. After 30 min (E)-5-bromopenta-1,3-diene 5a (67 mg, 0.4651 mmol) was added drop wise dissolved in dry DMF at 0° C. and kept stirring for 2 hrs at room temperature reaction was monitored by TLC. The reaction mixture was added to cold Water and extracted with ethyl acetate (3×20 mL) and combined organic layer washed with water, brine, then dried over $Na_2SO_4$, filtered, concentrated under reduced pressure, and purified by column chromatography (30% EA: DCM) to afford alkylated compound 5b (0.085 g, 68%) as yellow oil product.

Data for 5b: $^1$H NMR (400 MHz CDCl$_3$) δ 1.51 (s, 6H), 1.88 (t, J=5.7 Hz, 2H), 2.28 (s, 3H), 2.40 (s, 3H), 4.13 (t, J=5.5 Hz, 2H), 4.86 (d, J=5.52 Hz, 2H), 5.07 (d, J=9.29 Hz, 1H), 5.18 (d, J=15.81 Hz, 1H), 5.76 (dt, J=13.99, 5.93 Hz, 1H), 6.17-6.35 (m, 2H), 6.93 (s, 1H); $^{13}$C NMR (100 MHz, CDCl$_3$) δ 19.0, 21.6, 28.6 (2C), 33.2, 37.9, 39.6, 44.4, 114.9, 118.1, 121.9, 124.3, 124.8, 125.9, 131.9, 132.7, 133.9, 135.6, 153.40, 153.45; IR $v_{max}$ (film) cm$^{-1}$: 3429, 2925, 2855, 2251, 1662, 1680, 1462, 970; HRMS (ESI): m/z calculated for $C_{20}H_{24}O_2N_2$ [M$^+$Na]$^+$ 347.1730. found 347.1728.

Example 5: Synthesis of 7,7,8,9-tetramethyl-1-(2,3,4,5-tetrahydroxypentyl)-6,7-dihydro-1H,5H-pyrido[1,2,3-de]quinoxaline-2,3-dione (5)

A solution of (E)-7,7,8,9-tetramethyl-1-(penta-2,4-dien-1-yl)-6,7-dihydro-1H,5H-pyrido[1,2,3-de]quinoxaline-2,3-dione 5b (80 mg, 0.246 mmol) in Acetone:Water:tBuOH (5 ml, 7:2:1) was treated with NMO (115 mg, 0.987 mmol), Osmium tetraoxide (2.5% sol. in tBuOH) (0.100 ml, 0.0219 mmol) and cat t-BuOOH at rt and kept stirring for 12 h at room temperature reaction was monitored by TLC. The reaction mixture was added to cold sol of NaHSO4 and extracted with ethyl acetate (3×20 mL) and washed with water, brine, the combined organic layer were dried over $Na_2SO_4$, filtered, concentrated under reduced pressure, and purified by column chromatography (10% MeOH: DCM) to afford compound 5 (0.049 g, 51%) as yellow oil product.

Data for 5: $^1$H NMR (400 MHz, MeOD-d$_4$) δ 1.54 (s, 6H), 1.92 (t, J=5.8 Hz, 2H), 2.35 (s, 3H), 2.45 (s, 3H), 3.62-3.74 (m, 3H), 3.78-3.84 (m, 1H), 4.09-4.23 (m, 2H), 4.33-4.39 (m, 2H), 4.44-4.59 (m, 1H), 7.34-7.44 (2 singlet, 1H); $^{13}$C NMR (100 MHz, MeOD-d$_4$) δ 19.7, 21.7, 29.0, 29.3, 34.5, 39.4, 40.7, 47.3, 65.1, 68.6, 70.8, 72.7, 116.9, 123.3, 126.3, 133.9, 134.3, 136.1, 155.3, 156.4; IR $v_{max}$ (film) cm$^{-1}$: 3428, 2925, 2855, 1667, 1404, 1224; HRMS (ESI): m/z calculated for $C_{20}H_{28}O_6N_2$ [M+Na]$^+$ 415.1840. found 415.1838.

Example 6

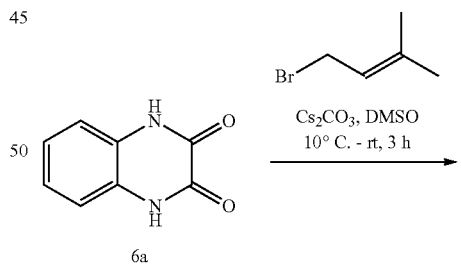

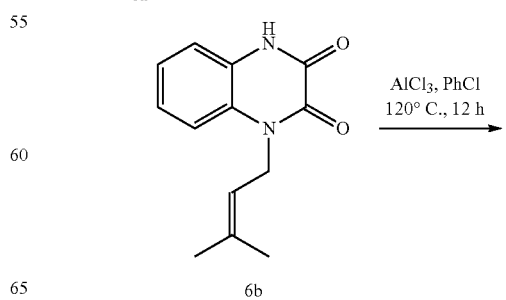

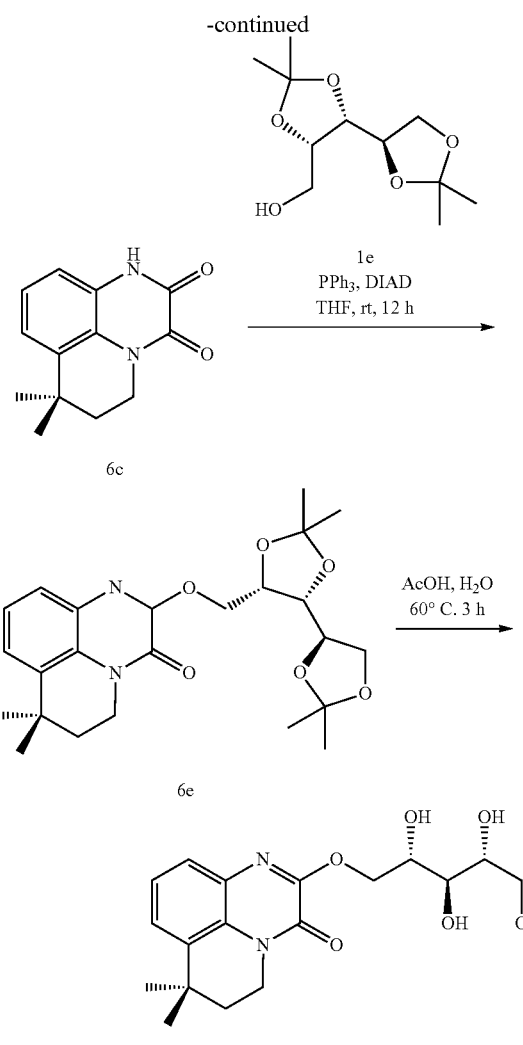

Example 6(a): Synthesis of 1-(3-methylbut-2-en-1-yl)-1,4-dihydroquinoxaline-2,3-dione (6b)

To a solution of 1,4-dihydroquinoxaline-2,3-dione 6a (2 gm, 0.012 mol) in dry DMSO (40 mL) was added caesium carbonate (4.8 g, 0.014 mol), followed by 3,3-dimethylallyl bromide (1.42 mL, 0.012 mol) diluted in 5 mL of DMSO and kept stirring for 3 hrs at room temperature reaction. The reaction mixture was added to cold water and extracted with ethyl acetate (3×100 mL). The combined organic layer was washed with brine and dried over $Na_2SO_4$, concentrated under reduced pressure, and subjected to flash chromatography over silica gel (40% EtOAc: petroleum ether) to afford mono-alkylated compound 6b (1.1 gm, 38%) as brown solid.

Data for 6b: $^1H$ NMR (500 MHz, DMSO-$d_6$) δ=12.04 (br. s., 1H), 7.32-7.08 (m, 4H), 5.24-5.02 (m, 1H), 4.85-4.61 (m, 2H), 1.82 (br. s., 3H), 1.67 (br. s., 3H); $^{13}C$ NMR (126 MHz, DMSO-$d_6$) δ=154.9, 153.6, 136.1, 126.2, 125.8, 123.5, 123.2, 118.7, 115.7, 115.0, 40.6, 25.3, 18.2.

Example 6(b): Synthesis of 7,7-dimethyl-6,7-dihydro-1H,5H-pyrido[1,2,3-de]quinoxaline-2,3-dione (6c)

A dried sealed tube charged with 1-(3-methylbut-2-en-1-yl)-1,4-dihydroquinoxaline-2,3-dione 6b (400 mg, 0.775 mmol) and $AlCl_3$ (693 mg, 5.21 mmol) in chlorobenzene (10 mL) was heated up to 120° C. for 3 hrs. The reaction was quenched by the addition of $H_2O$ (20 mL), then neutralised with saturated aqueous $NaHCO_3$. The reaction mixture was filtered through a pad of Celite® and washed with ethyl acetate. The resulting filtrate was partitioned with ethyl acetate (3×100 mL) and water. The combined organic layers were dried over $Na_2SO_4$, concentrated in vacuo and purified by flash column chromatography over silica gel (30% EtOAc: $CH_2Cl_2$) to afford compound 6c (310 mg, 77%) as brown solid.

Data for 6c: $^1H$ NMR (400 MHz, CHLOROFORM-d) δ=12.15 (br. s., 1H), 7.29 (d, J=8.1 Hz, 1H), 7.22 (d; J=7.8 Hz, 1H), 7.15 (dt, J=2.3, 7.8 Hz, 1H), 4.20 (t, J=5.5 Hz, 2H), 1.94 (t, J=6.1 Hz, 2H), 1.38 (s, 6H); $^{13}C$ NMR (101 MHz, CHLOROFORM-d) δ=155.6, 154.8, 134.4, 124.4, 124.0, 122.4, 121.3, 115.0, 39.1, 34.6, 31.6, 29.7.

Example 6(c): Synthesis of 7,7-dimethyl-2-(4S,4'R,5S)-2,2,2',2'-tetramethyl-[4,4'-bi(1,3-dioxolan)]-5-yl)methoxy)-6,7-dihydro-3H,5H-pyrido[1,2,3-de]quinoxalin-3-one (6e)

To a solution of 7,7-dimethyl-6,7-dihydro-1H,5H-pyrido[1,2,3-de]quinoxaline-2,3-dione 6c (100 mg, 0.43 mmol) in dry THF (3 mL) was added triphenylphosphine (262 mg, 1.00 mmol), ((4S,4'R,5 S)-2,2,2',2'-tetramethyl-[4,4'-bi(1,3-dioxolan)]-5-yl)methanol 6d (121 mg, 0.52 mmol) and DIAD (0.194 mL, 1.00 mmol) sequentially and stirred for 12 h at room temperature. The reaction mixture was diluted with water (5 mL) and extracted with ethyl acetate (3×10 mL), and the organic layer was washed successively with water and brine, dried over $Na_2SO_4$, and concentrated in vacuo. The residue was purified by flash silica gel column chromatography (40% EtOAc: $CH_2Cl_2$) to afford O-alkylated product 6e (122 mg, 63%) as brown coloured oil.

Data for 6e: $^1H$ NMR (400 MHz, CHLOROFORM-d) δ=7.51-7.45 (m, 1H), 7.39-7.34 (m, 1H), 7.26-7.21 (m, 1H), 4.83-4.77 (m, 1H), 4.77-4.63 (m, 2H), 4.26-4.09 (m, 5H), 4.00-3.93 (m, 1H), 1.93 (t, J=6.36 Hz, 2H), 1.49 (s, 3H), 1.41 (s, 3H), 1.38 (s, 6H), 1.37 (s, 3H), 1.31 (s, 3H); $^{13}C$ NMR (101 MHz, METHANOL-$d_4$) δ=153.2, 150.3, 133.4, 130.7, 126.8, 125.3, 123.5, 123.3, 109.7, 109.4, 77.7, 75.5, 73.5, 68.0, 65.7, 38.7, 34.7, 31.4, 27.7, 26.8, 25.5, 25.4.

Example 6: Synthesis of 7,7-dimethyl-2-(((2S,3R,4R)-2,3,4,5-tetrahydroxypentyl)oxy)-6,7-dihydro-3H,5H-pyrido[1,2,3-de]quinoxalin-3-one (6)

A solution of 7,7-dimethyl-2-4(4S,4'R,5S)-2,2,2',2'-tetramethyl-[4,4'-bi(1,3-dioxolan)]-5-yl)methoxy)-6,7-dihydro-3H,5H-pyrido[1,2,3-de]quinoxalin-3-one 22 (80 mg, 0.18 mmol) in acetic acid:water (1:1; 2 mL) was stirred for 3 h at 60° C. The reaction mixture was concentrated under reduced pressure, and purified by flash column chromatography (10% MeOH: $CH_2Cl_2$) to give compound 6 (38 mg, 58%) as colourless sticky solid. Data for 6: $^1H$ NMR (400 MHz, METHANOL-$D_3$) δ=7.51-7.40 (m, 2H), 7.33-7.22 (m, 1H), 4.69 (dd, J=3.0, 11.2 Hz, 1H), 4.48 (dd, J=7.3, 11.4 Hz, 1H), 4.26-4.16 (m, 3H), 3.89-3.63 (m, 4H), 1.97 (t, J=6.41 Hz, 2H), 1.40 (s, 6H); $^{13}C$ NMR (101 MHz, METHANOL-$D_3$) δ=154.3, 152.3, 135.3, 132.4, 127.5, 126.3, 125.3, 124.9, 74.1, 73.7, 71.8, 70.3, 64.5, 40.1, 35.7, 32.5, 30.2.

Example 7

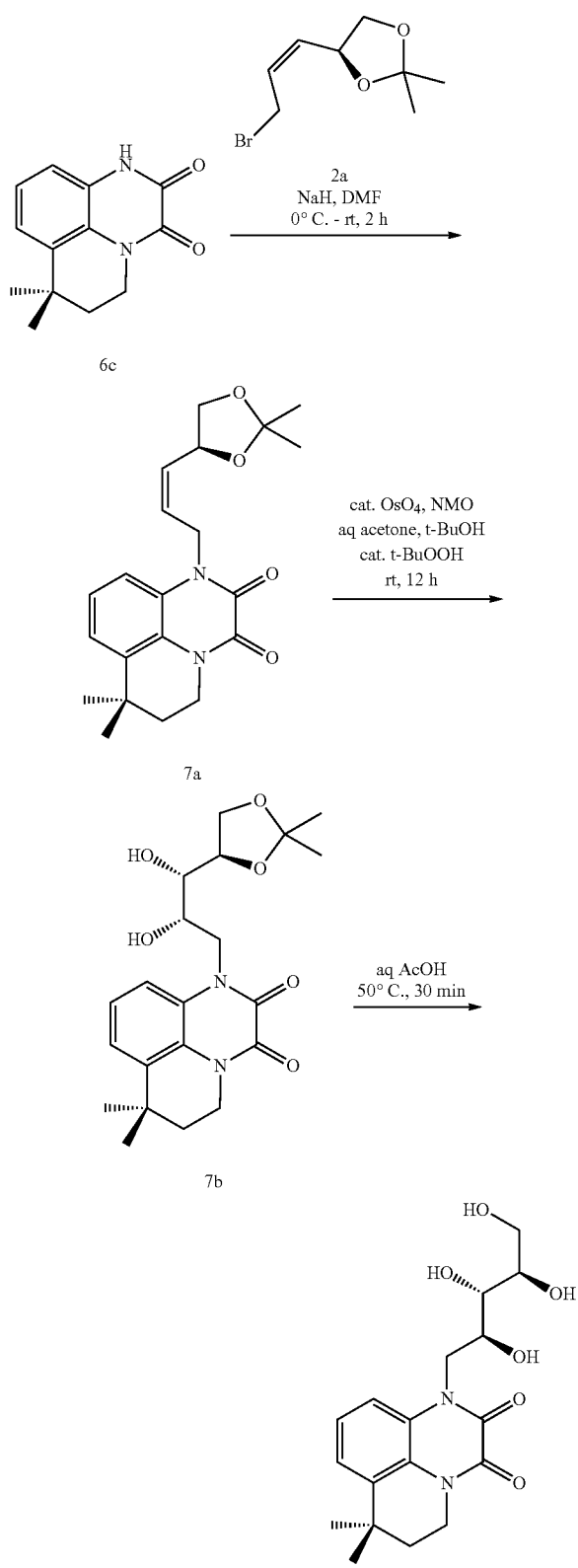

Example 7(a): Synthesis of (S,Z)-1-(3-(2,2-dimethyl-1,3-dioxolan-4-yl)allyl)-7,7-dimethyl-6,7-dihydro-1H,5H-pyrido[1,2,3-de]quinoxaline-2,3-dione (7a)

A solution of 7,7-dimethyl-6,7-dihydro-1H,5H-pyrido[1,2,3-de]quinoxaline-2,3-dione 6c (60 mg, 0.26 mmol) in dry DMF (1 mL) was added drop wise to pre-cooled (0° C.) suspension of sodium hydride (60% dispersion in mineral oil, 26 mg, 0.65 mmol) in 2 mL of DMF. The reaction mixture was allowed to warm to room temperature and stirred for 20 mins. (S,Z)-4-(3-bromoprop-1-en-1-yl)-2,2-dimethyl-1,3-dioxolane 2a (80 mg, 0.36 mmol), dissolved in dry DMF, was then added drop wise at 0° C. and stirred for 2 hrs at room temperature. The reaction mixture was added to cold water (10 mL) and extracted with ethyl acetate (3×10 mL) and the combined organic layers were washed with water, brine, then dried over $Na_2SO_4$, filtered and concentrated in vacuo, and purified by column chromatography (30% EtOAc: $CH_2Cl_2$) to afford compound 7a (55 mg, 57%) as colourless oil.

Data for 7a: $^1$H NMR (400 MHz, CHLOROFORM-d) δ=7.29-7.12 (m, 3H), 5.75-5.65 (m, 1H), 5.65-5.55 (m, 1H), 5.32-5.20 (m, 1H), 5.16-5.05 (m, 1H), 4.80-4.70 (m, 1H), 4.28-4.21 (m, 1H), 4.21-4.12 (m, 2H), 3.68-3.58 (m, 1H), 1.98-1.84 (m, 4H), 1.45 (s, 3H), 1.44 (s, 3H), 1.38 (s, 6H); $^{13}$C NMR (101 MHz, CHLOROFORM-d) δ=153.7, 153.6, 134.9, 131.9, 127.0, 126.2, 123.9, 122.6, 121.4, 113.0, 109.6, 72.1, 69.4, 40.9, 39.0, 34.3, 31.9, 29.9, 26.7, 25.8.

Example 7(b): Synthesis of 1-((2S,3S)-3-((R)-2,2-dimethyl-1,3-dioxolan-4-yl)-2,3-dihydroxypropyl)-7,7-dimethyl-6,7-dihydro-1H,5H-pyrido[1,2,3-de]quinoxaline-2,3-dione (7b)

A solution of (S,Z)-1-(3-(2,2-dimethyl-1,3-dioxolan-4-yl)allyl)-7,7-dimethyl-6,7-dihydro-1H,5H-pyrido[1,2,3-de]quinoxaline-2,3-dione 7a (50 mg, 0.13 mmol) in acetone:water:t-BuOH (2 mL, 7:2:1) was treated with NMO (63 mg, 0.54 mmol), osmium tetraoxide (2.5% sol. in t-BuOH) (0.13 mL, 0.01 mmol) and cat. t-BuOOH and stirred for 12 h at room temperature. The reaction mixture was added to cold solution of $NaHSO_4$ and extracted with ethyl acetate (3×30 mL) and washed with water, brine and the combined organic layers were dried over $Na_2SO_4$, filtered and concentrated in vacuo. The resultant residue was purified by flash chromatography on silica (5% MeOH: $CH_2Cl_2$) to afford hydroxylated compound 7b (35 mg, 64%) as colourless oil.

Data for 7b: $^1$H NMR (400 MHz, CHLOROFORM-d) δ=7.56 (dd, J=1.5, 8.3 Hz, 1H), 7.34-7.20 (m, 2H), 4.77 (dd, J=6.1, 14.9 Hz, 1H), 4.45-4.32 (m, 2H), 4.30-4.16 (m, 3H), 4.16-4.09 (m, 1H), 4.05-3.97 (m, 2H), 3.68-3.62 (m, 1H), 1.93 (t, J=6.1 Hz, 3H), 1.41 (s, 3H), 1.39 (s, 9H); $^{13}$C NMR (101 MHz, CHLOROFORM-d) δ=156.2, 153.5, 134.7, 127.0, 123.9, 122.8, 121.9, 114.6, 109.7, 73.4, 72.5, 67.6, 46.4, 39.2, 34.3, 32.0, 29.9, 26.6, 25.2.

Example 7: Synthesis of 7,7-dimethyl-1-((2S,3S,4R)-2,3,4,5-tetrahydroxypentyl)-6,7-dihydro-1H,5H-pyrido[1,2,3-de]quinoxaline-2,3-dione (7)

A solution of 1-((2S,3S)-3-((R)-2,2-dimethyl-1,3-dioxolan-4-yl)-2,3-dihydroxypropyl)-7,7-dimethyl-6,7-dihydro-1H,5H-pyrido[1,2,3-de]quinoxaline-2,3-dione 7b (35 mg, 0.08 mmol) in acetic acid:water (1:1; 1 mL) was stirred for 30 min at 50° C. The reaction mixture was then concentrated in vacuo, and purified by flash chromatography on SiO$_2$ (10% MeOH: CH$_2$Cl$_2$) to afford compound 7 (20 mg, 64%) as yellow solid.

Data for 7: $^1$H NMR (400 MHz, METHANOL-D$_3$) δ=7.55 (d, J=8.2 Hz, 1H), 7.39-7.33 (m, 1H), 7.26 (t, J=8.0 Hz, 1H), 4.77 (dd, J=9.8, 14.4 Hz, 1H), 4.61 (s, 1H), 4.33 (dd, J=2.7, 14.2 Hz, 1H), 4.27-4.21 (m, 1H), 4.19-4.14 (m, 2H), 3.83-3.73 (m, 3H), 3.70-3.61 (m, 1H), 1.96 (t, J=6.41 Hz, 2H), 1.40 (s, 3H), 1.39 (s, 3H); $^{13}$C NMR (101 MHz, METHANOL-D$_3$) δ=156.9, 155.7, 136.4, 128.5, 125.2, 124.1, 122.9, 115.6, 75.1, 74.3, 71.0, 64.9, 46.9, 40.4, 35.6, 33.2, 30.4, 30.3

Example 8

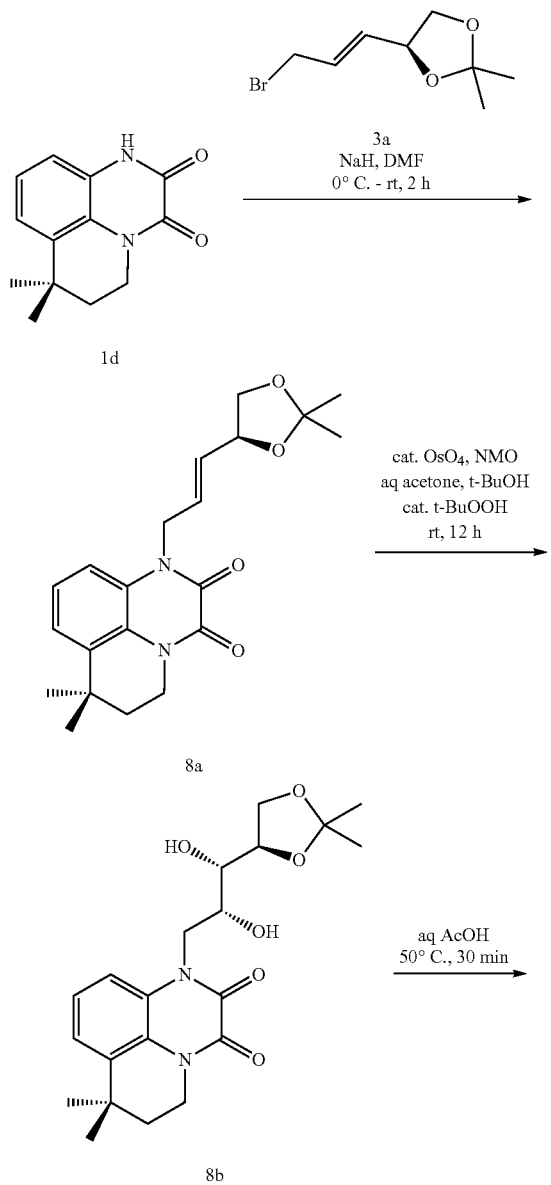

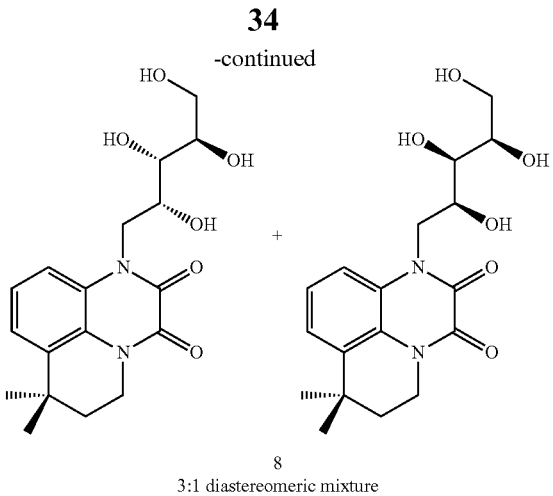

8
3:1 diastereomeric mixture

Example 8(a): Synthesis of (S,E)-1-(3-(2,2-dimethyl-1,3-dioxolan-4-yl)allyl)-7,7-dimethyl-6,7-dihydro-1H,5H-pyrido[1,2,3-de]quinoxaline-2,3-dione (8a)

A solution of 7,7-dimethyl-6,7-dihydro-1H,5H-pyrido[1,2,3-de]quinoxaline-2,3-dione 6c (60 mg, 0.26 mmol) in dry DMF (1 mL) was added dropwise to pre-cooled suspension of sodium hydride (60% dispersion in mineral oil, 26 mg, 0.65 mmol) in 1 mL of DMF. The cooling bath was then removed, and the flask was allowed to warm to room temperature and stirred for 20 mins. (S,E)-4-(3-bromoprop-1-en-1-yl)-2,2-dimethyl-1,3-dioxolane 3a (80 mg, 0.36 mmol), dissolved in dry DMF, was added drop wise at 0° C. and stirred for 2 hrs at room temperature, then reaction mixture was added to cold water and extracted with ethyl acetate (3×10 mL). The combined organics were dried over Na$_2$SO$_4$, filtered and concentrated in vacuo. The resultant residue was purified by flash chromatography on SiO$_2$ (30% EtOAc: CH$_2$Cl$_2$) to afford compound 8a (70 mg, 72%) as brown gummy mass.

Data for 8a: $^1$H NMR (400 MHz, CHLOROFORM-d) δ=7.28-7.22 (m, 1H), 7.18 (t, J=8.0 Hz, 1H), 7.09-7.05 (m, 1H), 5.90 (td, J=5.4, 15.6 Hz, 1H), 5.73 (ddd, J=1.3, 6.8, 15.6 Hz, 1H), 4.86 (t, J=4.8 Hz, 2H), 4.49 (q, J=6.8 Hz, 1H), 4.22-4.13 (m, 2H), 4.05 (dd, J=6.1, 8.2 Hz, 1H), 3.54 (t, J=7.9 Hz, 1H), 1.92 (t, J=6.27 Hz, 2H), 1.38 (s, 9H), 1.34 (s, 3H); $^{13}$C NMR (101 MHz, CHLOROFORM-d) δ=153.7, 153.7, 134.9, 131.7, 126.3, 125.9, 123.9, 122.6, 121.4, 113.2, 109.4, 76.0, 69.2, 44.3, 39.0, 34.4, 32.0, 29.9, 26.6, 25.7.

Example 8(b): Synthesis of 1-((2R,3S)-3-((R)-2,2-dimethyl-1,3-dioxolan-4-yl)-2,3-dihydroxypropyl)-7,7-dimethyl-6,7-dihydro-1H,5H-pyrido[1,2,3-de]quinoxaline-2,3-dione (8b)

A solution of (S,E)-1-(3-(2,2-dimethyl-1,3-dioxolan-4-yl)allyl)-7,7-dimethyl-6,7-dihydro-1H,5H-pyrido[1,2,3-de] quinoxaline-2,3-dione 8a (35 mg, 0.09 mmol) in acetone: water:t-BuOH (2 mL, 7:2:1) was treated with NMO (44 mg, 0.37 mmol), osmium tetraoxide (2.5% sol. in t-BuOH) (0.09 mL, 0.009 mmol) and cat. t-BuOOH at room temperature and stirred for 12 hrs. The reaction mixture was added to cold sol of NaHSO$_4$ and extracted with ethyl acetate (3×10 mL) and washed with water, brine. The combined organics were dried over Na$_2$SO$_4$, filtered and concentrated in vacuo.

The resultant residue was purified by flash chromatography on SiO$_2$ (5% MeOH: CH$_2$Cl$_2$) to afford compound 8b (28 mg, 73%, 3:1 inseparable diastereomers) as yellow sticky solid.

Data for 8b $^1$H NMR (400 MHz, CHLOROFORM-d) δ=7.40-7.20 (m, 3H), 4.59-4.46 (m, 1H), 4.39-4.27 (m, 2H), 4.27-4.09 (m, 5H), 4.02-3.87 (m, 2H), 3.48-3.39 (m, 1H), 1.93 (t, J=6.4 Hz, 2H), 1.39 (s, 6H), 1.31 (s, 3H), 1.26 (s, 3H); $^{13}$C NMR (101 MHz, CHLOROFORM-d) δ=155.5, 153.4, 135.1, 126.3, 124.2, 122.7, 122.0, 113.3, 109.2, 75.2, 71.6, 68.2, 67.3, 46.4, 39.2, 34.3, 32.0, 29.9, 29.9, 26.7, 25.1.

Note: Minor peaks in NMR ($^1$H and $^{13}$C) which could not be cleanly distinguished, corresponds to other diastereomer.

Example 8: Synthesis of 7,7-dimethyl-1-((2R,3S, 4R)-2,3,4,5-tetrahydroxypentyl)-6,7-dihydro-1H,5H-pyrido[1,2,3-de]quinoxaline-2,3-dione (8)

A solution of 1-((2R,3S)-3-((R)-2,2-dimethyl-1,3-dioxolan-4-yl)-2,3-dihydroxypropyl)-7,7-dimethyl-6,7-dihydro-1H,5H-pyrido[1,2,3-de]quinoxaline-2,3-dione 8b (30 mg, 0.07 mmol) in Acetic acid:Water (1:1) 1 mL and kept stirring for 3 hrs at 60° C. reaction was monitored by TLC. The reaction mixture concentrated under reduced pressure, and purified by column chromatography (10% MeOH: CH$_2$Cl$_2$) to afford compound 8 (15 mg, 55%, 3:1 inseparable diastereomers) as colourless gum.

Data for 8: $^1$H NMR (400 MHz, METHANOL-d$_4$) δ=7.57-7.49 (m, 1H), 7.40-7.34 (m, 1H), 7.32-7.22 (m, 1H), 4.66-4.45 (m, 2H), 4.45-4.29 (m, 2H), 4.24-4.11 (m, 2H), 3.86-3.58 (m, 2H), 1.96 (t, J=6.41 Hz, 2H), 1.40 (s, 3H), 1.39 (s, 3H); $^{13}$C NMR (101 MHz, CHLOROFORM-d) δ=156.7, 155.7, 136.5, 128.5, 125.3, 124.1, 123.0, 115.4, 72.7, 72.7, 68.6, 65.2, 47.7, 40.4, 35.6, 33.2, 30.3.

Note: Minor peaks in NMR ($^1$H and $^{13}$C) which could not be cleanly distinguished, corresponds to other diastereomer.

Example 9

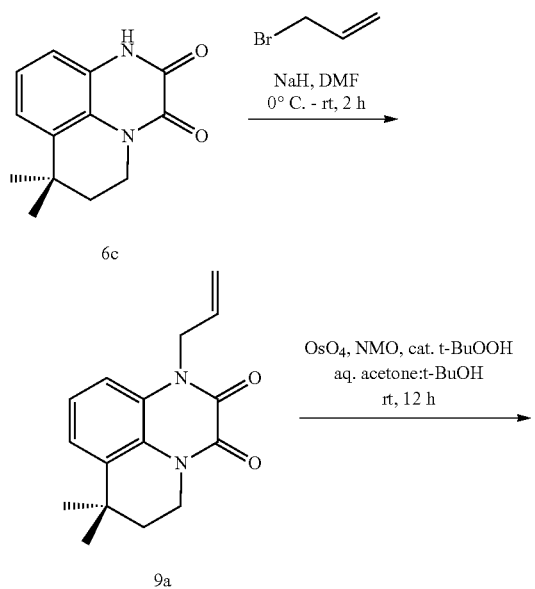

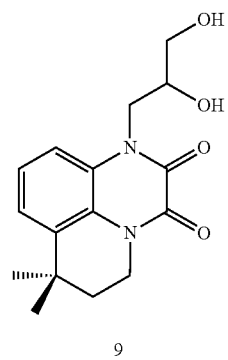

Example 9(a): Synthesis of 1-allyl-7,7-dimethyl-6, 7-dihydro-1H,5H-pyrido[1,2,3-de]quinoxaline-2,3-dione (9a)

A solution of 7,7-dimethyl-6,7-dihydro-1H,5H-pyrido[1, 2,3-de]quinoxaline-2,3-dione 6c (50 mg, 0.21 mmol) in dry DMF (1 mL) was added drop wise to a pre-cooled suspension of sodium hydride (60% dispersion in mineral oil, 19 mg, 0.47 mmol) in 1 mL of DMF. Then cooling bath was removed, and the flask was allowed to warm to room temperature and stirred for 20 mins. Allyl bromide (22 µl, 0.26 mmol) was then added drop wise at 0° C. and stirred for 2 hrs at room temperature. The reaction was quenched by the addition of H$_2$O (5 mL) and extracted with ethyl acetate (3×10 mL). The combined organics were dried over Na$_2$SO$_4$, filtered and concentrated in vacuo. The resultant residue was purified by flash chromatography on SiO$_2$ (30% EtOAc: CH$_2$Cl$_2$) to afford compound 9a (38 mg, 65%) as colourless oil.

Data for 9a: $^1$H NMR (400 MHz, CHLOROFORM-d) δ=7.29-7.22 (m, 1H), 7.18 (t, J=7.9 Hz, 1H), 7.13-7.07 (m, 1H), 5.92 (tdd, J=5.1, 10.4, 17.3 Hz, 1H), 5.36-5.17 (m, 2H), 4.95-4.79 (m, 2H), 4.27-4.08 (m, 2H), 1.93 (t, J=6.27 Hz, 2H), 1.39 (s, 6H); $^{13}$C NMR (101 MHz, CHLOROFORM-d) δ=153.8, 153.76, 134.8, 130.6, 126.4, 123.7, 122.6, 121.3, 118.2, 113.4, 45.6, 39.1, 34.4, 32.0, 29.9.

Example 9: Synthesis of 1-(2,3-dihydroxypropyl)-7, 7-dimethyl-6,7-dihydro-1H,5H-pyrido[1,2,3-de]quinoxaline-2,3-dione (9)

A solution of 1-allyl-7,7-dimethyl-6,7-dihydro-1H,5H-pyrido[1,2,3-de]quinoxaline-2,3-dione 9a (50 mg, 0.21 mmol) in acetone:water:t-BuOH (2 mL, 7:2:1) was treated with NMO (101 mg, 0.86 mmol), osmium tetraoxide (2.5% sol. in t-BuOH) (0.22 mL, 0.02 mmol) and cat. T-BuOOH and stirred for 12 hrs at room temperature. The reaction mixture was quenched with ice cold solution of NaHSO$_4$ (2 mL) and extracted with ethyl acetate (3×5 mL) and washed with water and brine. The combined organic layer were dried over Na$_2$SO$_4$, filtered and concentrated in vacuo, and purified by column chromatography (10% MeOH: CH$_2$Cl$_2$) to afford compound 9 (38 mg, 58%) as colourless oil.

Data for 9: $^1$H NMR (400 MHz, METHANOL-d$_4$) δ=7.12-6.94 (m, 3H), 4.08-3.79 (m, 5H), 3.66-3.46 (m, 2H), 2.00-1.82 (m, 2H), 1.42-1.23 (m, 6H); $^{13}$C NMR (101 MHz, METHANOL-d$_4$) δ=155.5 (2C), 130.2, 129.8, 126.3, 122.7, 117.7, 107.7, 71.7, 65.0, 45.5, 37.9, 37.6, 32.9, 29.0.

Example 10

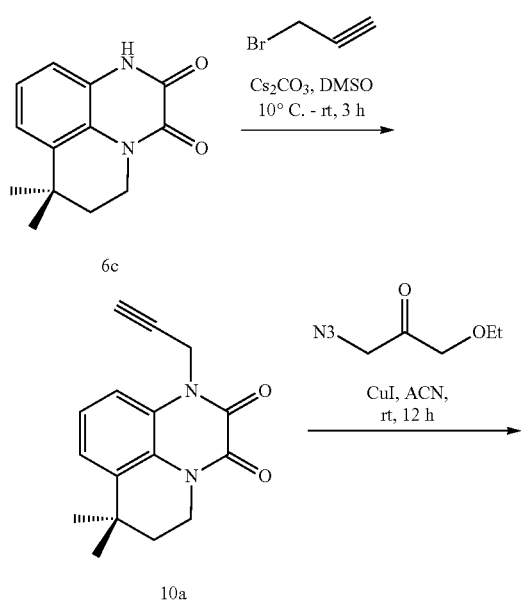

Example 10: Synthesis of ethyl 2-(4-((7,7-dimethyl-2,3-dioxo-2,3,6,7-tetrahydro-1H,5H-pyrido[1,2,3-de]quinoxalin-1-yl)methyl)-1H-1,2,3-triazol-1-yl)acetate (10)

A solution of 7,7-dimethyl-1-(prop-2-yn-1-yl)-6,7-dihydro-1H,5H-pyrido[1,2,3-de]quinoxaline-2,3-dione 10a (150 mg, 0.55 mmol) in acetonitrile (5 mL) was treated with Ethyl azidoacetate (146 mg, 0.61 mmol and cat. CuI and stirred for 12 hrs at room temperature. The reaction mixture was added to water and extracted with ethyl acetate (3×30 mL) and washed with water, brine and the combined organic layers were dried over $Na_2SO_4$, filtered and concentrated in vacuo. The resultant residue was purified by flash chromatography on silica (50% Ethyl acetate: Pet ether) to afford compound 10 (183 mg, 82%) as brown oil.

Data for 10: $^1$H NMR (400 MHz, CHLOROFORM-d) δ=7.90 (s, 1H), 7.73 (dd, J=3.2, 6.4 Hz, 1H), 7.25-7.21 (m, 2H), 5.48 (s, 2H), 5.12 (s, 2H), 4.22 (q, J=7.2 Hz, 2H), 4.17-4.12 (m, 2H), 1.90 (t, J=6.41 Hz, 2H), 1.35 (s, 6H), 1.25 (t, J=7.1 Hz, 3H); $^{13}$C NMR (101 MHz, CHLOROFORM-d) δ=166.0, 154.0, 153.6, 142.5, 134.7, 126.2, 125.5, 124.1, 122.5, 121.6, 113.8, 62.4, 50.8, 39.0, 34.3, 31.9, 29.8, 13.9.

Example 10(a): Synthesis of 7,7-dimethyl-1-(prop-2-yn-1-yl)-6,7-dihydro-1H,5H-pyrido[1,2,3-de]quinoxaline-2,3-dione (10a)

To a solution of 7,7-dimethyl-6,7-dihydro-1H,5H-pyrido[1,2,3-de]quinoxaline-2,3-dione 6c (500 mg, 2.17 mmol) in dry DMF (5 mL) was added caesium carbonate (1.05 gm, 3.25 mmol) followed by propargyl bromide (0.196 mL, 2.60 mmol) dissolved in dry DMF, was then added drop wise at 0° C. and stirred for 2 hrs at room temperature. The reaction mixture was added to cold water (10 mL) and extracted with ethyl acetate (3×10 mL) and the combined organic layers were washed with water, brine, then dried over $Na_2SO_4$, filtered and concentrated in vacuo, and purified by column chromatography (30% EtOAc: $CH_2Cl_2$) to afford compound 10a (480 mg, 82%) as brown sticky solid.

Data for 10a: $^1$H NMR (400 MHz, CHLOROFORM-d) δ=7.35-7.19 (m, 3H), 4.99 (d, J=1.8 Hz, 2H), 4.17-4.13 (m, 2H), 2.28 (s, 1H), 1.93 (t, J=6.27 Hz, 2H), 1.36 (s, 6H); $^{13}$C NMR (101 MHz, CHLOROFORM-d) δ=153.4, 153.3, 134.9, 125.6, 123.9, 122.6, 121.7, 113.3, 76.7, 73.4, 39.1, 34.3, 32.7, 31.9, 29.9.

Example 11

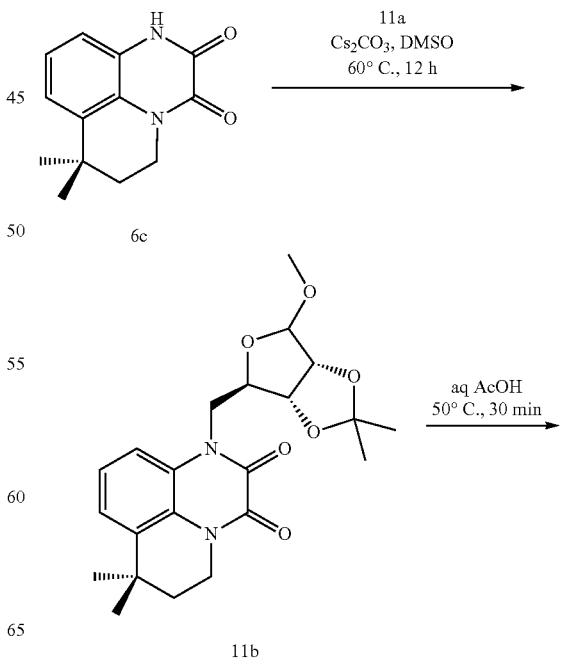

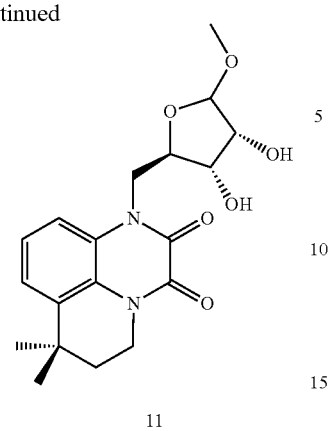

11

Example 11(a): Synthesis of 1-(((3aR,4R,6aR)-6-methoxy-2,2-dimethyltetrahydrofuro[3,4-d][1,3]dioxol-4-yl)methyl)-7,7-dimethyl-6,7-dihydro-1H,5H-pyrido[1,2,3-de]quinoxaline-2,3-dione (11b)

To a solution of 7,7-dimethyl-6,7-dihydro-1H,5H-pyrido[1,2,3-de]quinoxaline-2,3-dione 6c (150 mg, 0.65 mmol) in dry DMF (5 mL) was added caesium carbonate (317 mg, 0.97 mmol) followed by ((3aR,4R,6aR)-6-methoxy-2,2-dimethyltetrahydrofuro[3,4-d][1,3]dioxol-4-yl)methyl 4-methylbenzenesulfonate 11a (280 mg, 0.78 mmol) was then added and stirred for 12 hrs at room temperature. The reaction mixture was added to cold water (10 mL) and extracted with ethyl acetate (3×10 mL) and the combined organic layers were washed with water, brine, then dried over $Na_2SO_4$, filtered and concentrated in vacuo, and purified by column chromatography (30% Ethyl acetate: Dichloromethane) to afford compound 11b (130 mg, 47%) as brown sticky solid.

Data for 11b: $^1$H NMR (400 MHz, CHLOROFORM-d) δ=7.36-7.15 (m, 3H), 5.03 (s, 1H), 4.98-4.92 (m, 2H), 4.76 (d, J=7.6 Hz, 1H), 4.46 (dd, J=3.1, 10.1 Hz, 1H), 4.18 (t, J=6.2 Hz, 2H), 3.87 (dd, J=3.4, 14.4 Hz, 1H), 3.44 (s, 3H), 1.93 (t, J=6.11 Hz, 2H), 1.41 (s, 3H), 1.39 (s, 6H), 1.26 (s, 3H); $^{13}$C NMR (101 MHz, DEUTERIUM OXIDE) δ=154.2, 153.4, 135.2, 125.9, 124.0, 122.8, 121.6, 112.8, 112.3, 110.0, 85.3, 83.3, 82.3, 55.3, 45.1, 39.0, 34.3, 32.0, 29.9, 26.2, 24.7.

Example 11: Synthesis of 1-(((2R,3S,4R)-3,4-dihydroxy-5-methoxytetrahydrofuran-2-yl)methyl)-7,7-dimethyl-6,7-dihydro-1H,5H-pyrido[1,2,3-de]quinoxaline-2,3-dione (11)

A solution of 1-(((3aR,4R,6aR)-6-methoxy-2,2-dimethyltetrahydrofuro[3,4-d][1,3]dioxol-4-yl)methyl)-7,7-dimethyl-6,7-dihydro-1H,5H-pyrido[1,2,3-de]quinoxaline-2,3-dione 11b (60 mg, 0.14 mmol) in Acetic acid:Water (1:1) 1 mL and kept stirring for 3 hrs at 60° C. reaction was monitored by TLC. The reaction mixture concentrated under reduced pressure, and purified by column chromatography (10% MeOH: $CH_2Cl_2$) to afford compound 11 (18 mg, 33%) as colourless gum.

Data for 11: $^1$H NMR (400 MHz, METHANOL-$d_4$) δ=7.44 (d, J=8.3 Hz, 1H), 7.38 (d, J=8.8 Hz, 1H), 7.28 (t, J=8.1 Hz, 1H), 4.70 (s, 1H), 4.59-4.52 (m, 2H), 4.35-4.29 (m, 1H), 4.28-4.21 (m, 1H), 4.21-4.13 (m, 2H), 3.91 (d, J=4.4 Hz, 1H), 3.30 (s, 3H), 1.97 (t, J=6.36 Hz, 2H), 1.41 (s, 3H), 1.41 (s, 3H); $^{13}$C NMR (101 MHz, CHLOROFORM-d) δ=156.4, 155.6, 136.5, 128.2, 125.2, 124.1, 123.0, 115.4, 110.4, 80.7, 76.3, 74.9, 56.0, 47.5, 40.4, 35.6, 33.2, 30.4, 30.3.

Example 12

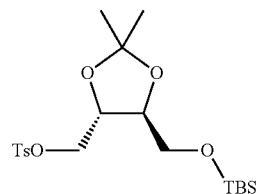

12a

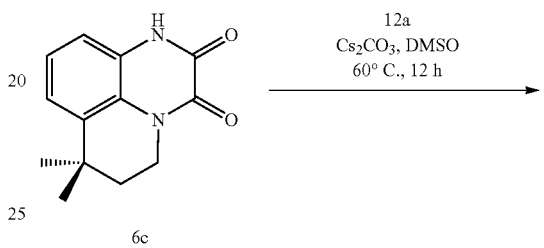

6c

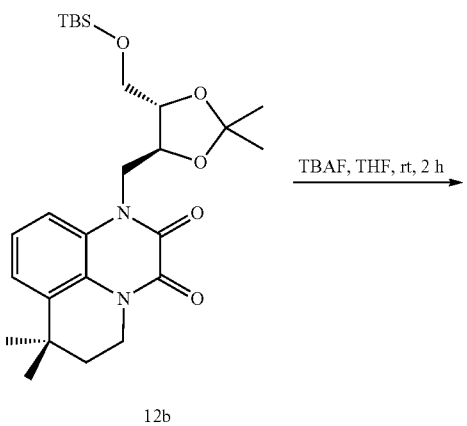

12b

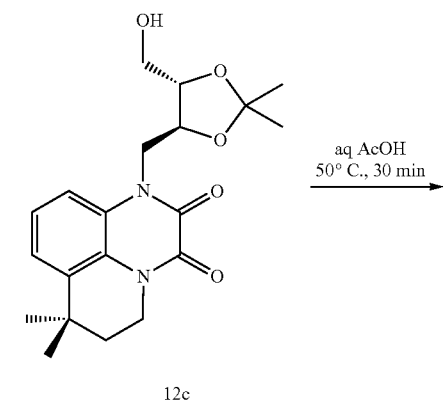

12c

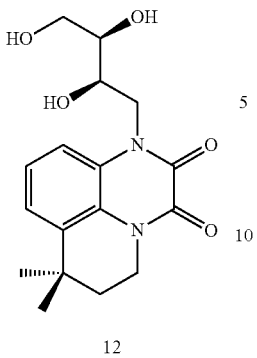

12

Example 12(a): Synthesis of 1-(((4S,5S)-5-(((tert-butyldimethylsilyl)oxy)methyl)-2,2-dimethyl-1,3-dioxolan-4-yl)methyl)-7,7-dimethyl-6,7-dihydro-1H,5H-pyrido[1,2,3-de]quinoxaline-2,3=dione (12b)

To a solution of 7,7-dimethyl-6,7-dihydro-1H,5H-pyrido[1,2,3-de]quinoxaline-2,3-dione 6c (150 mg, 0.65 mmol) in dry DMF (5 mL) was added caesium carbonate (275 mg, 0.84 mmol) followed by ((4S,5S)-5-(((tert-butyldimethylsilyl)oxy)methyl)-2,2-dimethyl-1,3-dioxolan-4-yl)methyl 4-methylbenzenesulfonate 12a (336 mg, 0.78 mmol) was then added and stirred for 12 hrs at 60° C. The reaction mixture was added to cold water (10 mL) and extracted with ethyl acetate (3×10 mL) and the combined organic layers were washed with water, brine, then dried over $Na_2SO_4$, filtered and concentrated in vacuo, and purified by column chromatography (30% Ethyl acetate: pet ether) to afford compound 12b (130 mg, 40%) as yellow sticky solid.

Data for 12b: $^1$H NMR (500 MHz, CHLOROFORM-d) δ=7.36 (dd, J=1.1, 8.4 Hz, 1H), 7.25 (dd, J=1.1, 7.6 Hz, 1H), 7.19 (t, J=8.0 Hz, 1H), 4.50 (d, J=5.3 Hz, 2H), 4.44-4.33 (m, 1H), 4.18 (t, J=6.48 Hz, 2H), 3.99 (ddd, J=4.0, 5.5, 7.6 Hz, 1H), 3.85 (dd, J=3.8, 10.7 Hz, 1H), 3.77 (dd, J=5.7, 10.7 Hz, 1H), 1.92 (t, J=6.48 Hz, 2H), 1.44 (s, 3H), 1.39 (s, 3H), 1.37 (s, 3H), 1.34 (s, 3H), 0.86 (s, 9H), 0.07 (s, 3H), 0.03 (s, 3H); $^{13}$C NMR (126 MHz, CHLOROFORM-d) δ=154.3, 153.6, 134.7, 126.9, 123.6, 122.7, 121.4, 113.8, 109.8, 79.6, 76.0, 63.1, 45.9, 39.1, 34.4, 32.0, 30.0, 30.0, 26.9, 25.9, 18.3, −5.4, −5.6.

Example 12(b): Synthesis of 1-(((4S,5S)-5-(hydroxymethyl)-2,2-dimethyl-1,3-dioxolan-4-yl)methyl)-7,7-dimethyl-6,7-dihydro-1H,5H-pyrido[1,2,3-de]quinoxaline-2,3-dione (12c)

A solution of 1-(((4S,5S)-5-(((tert-butyldimethylsilyl)oxy)methyl)-2,2-dimethyl-1,3-dioxolan-4-yl)methyl)-7,7-dimethyl-6,7-dihydro-1H,5H-pyrido[1,2,3-de]quinoxaline-2,3-dione 12b (90 mg, 0.18 mmol) in THF 5 mL was added tetra-n-butyl ammonium fluoride TBAF (1M Solution in THF) (0.22 mL, 0.22 mmol) and kept stirring at room temperature for 2 hrs the reaction was monitored by TLC. The reaction mixture diluted with water and extracted with ethyl acetate. Organic layer was then concentrated under reduced pressure, and purified by column chromatography (30% Ethyl acetate: dichloromethane) to afford compound 12c (52 mg, 76%) as colourless gum.

Data for 12c: $^1$H NMR (400 MHz, CHLOROFORM-d) δ=7.47 (d, J=7.8 Hz, 1H), 7.39 (d, J=7.3 Hz, 1H), 7.28-7.23 (m, 1H), 4.73 (dd, J=5.3, 10.8 Hz, 1H), 4.54-4.48 (m, 1H), 4.36-4.30 (m, 1H), 4.22-4.11 (m, 3H), 3.91 (dd, J=4.1, 11.9 Hz, 1H), 3.84 (dd, J=3.7, 11.9 Hz, 1H), 1.93 (t, J=5.5 Hz, 2H), 1.48 (s, 3H), 1.45 (s, 3H), 1.38 (s, 6H); $^{13}$C NMR (101 MHz, CHLOROFORM-d) δ=152.7, 150.2, 133.6, 130.5, 126.8, 125.3, 123.7, 123.7, 109.7, 79.8, 75.8, 66.9, 62.6, 38.7, 34.6, 31.4, 29.7, 27.0, 26.8.

Example 12: Synthesis of 7,7-dimethyl-1-((2R,3R)-2,3,4-trihydroxybutyl)-6,7-dihydro-1H,5H-pyrido[1,2,3-de]quinoxaline-2,3-dione (12)

A solution of 1-(((4S,5S)-5-(hydroxymethyl)-2,2-dimethyl-1,3-dioxolan-4-yl)methyl)-7,7-dimethyl-6,7-dihydro-1H,5H-pyrido[1,2,3-de]quinoxaline-2,3-dione 12c (40 mg, 0.10 mmol) in Acetic acid:Water (1:1) 1 mL and kept stirring for 2 hrs at 60° C. reaction was monitored by TLC. The reaction mixture concentrated under reduced pressure, and purified by column chromatography (5% Methanol: dichloromethane) to afford compound 12 (25 mg, 83%) as colourless gum.

Data for 12: $^1$H NMR (400 MHz, METHANOL-$d_4$) δ=7.54 (d, J=7.8 Hz, 1H), 7.40-7.34 (m, 1H), 7.32-7.24 (m, 1H), 4.56 (dd, J=8.6, 14.2 Hz, 1H), 4.37 (dd, J=4.4, 14.2 Hz, 1H), 4.22-4.10 (m, 3H), 3.74-3.63 (m, 3H), 1.97 (t, J=6.11 Hz, 2H), 1.42 (s, 3H), 1.41 (s, 3H); $^{13}$C NMR (101 MHz, CHLOROFORM-d) δ=156.7, 155.6, 136.4, 128.6, 125.3, 124.1, 122.9, 115.5, 73.6, 69.7, 64.2, 47.7, 40.4, 35.6, 33.2, 30.4, 30.4.

Example 13

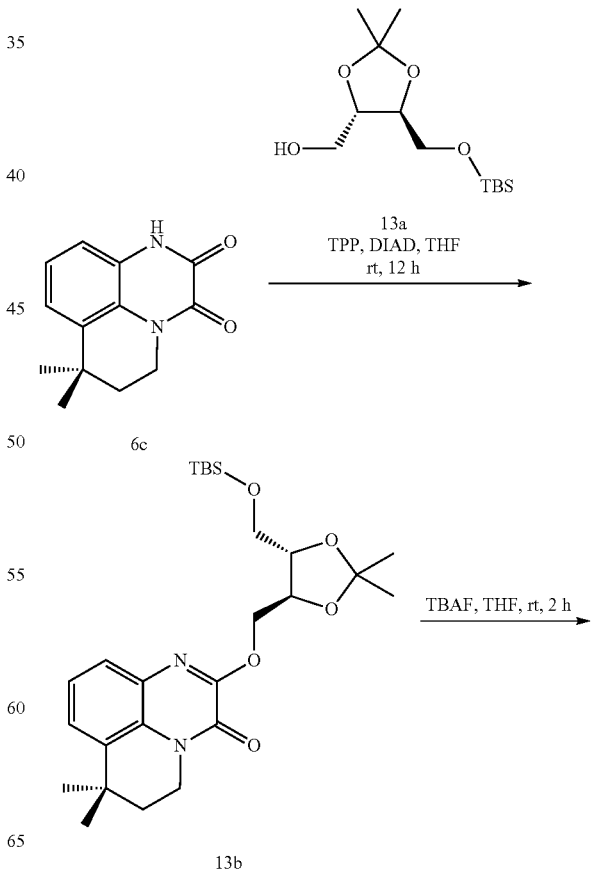

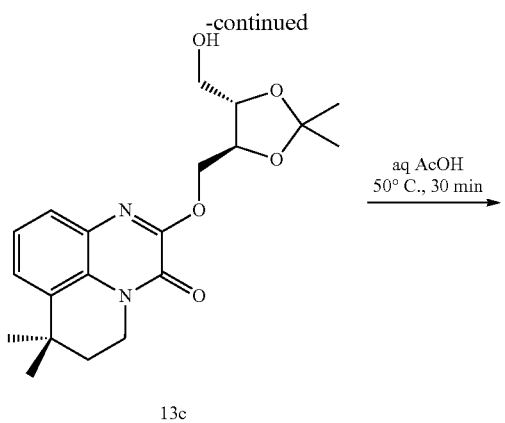

Example 13(a): Synthesis of 2-(((4S,5S)-5-(((tert-butyldimethylsilyoxy)methyl)-2,2-dimethyl-1,3-dioxolan-4-yl)methoxy)-7,7-dimethyl-6,7-dihydro-3H,5H-pyrido[1,2,3-de]quinoxalin-3-one (13b)

To a solution of 7,7-dimethyl-6,7-dihydro-1H,5H-pyrido[1,2,3-de]quinoxaline-2,3-dione 6c (150 mg, 0.65 mmol) in dry THF (6 mL) was added triphenylphosphine (392 mg, 1.49 mmol), ((4S,5S)-5-(((tert-butyldimethylsilyl)oxy)methyl)-2,2-dimethyl-1,3-dioxolan-4-yl)methanol 13a (233 mg, 0.84 mmol) and DIAD (0.283 mL, 1.49 mmol) sequentially and stirred for 12 hrs at room temperature. The reaction mixture was diluted with water (15 mL) and extracted with ethyl acetate (3×20 mL), and the organic layer was washed successively with water and brine, dried over $Na_2SO_4$, and concentrated in vacuo. The residue was purified by flash silica gel column chromatography (20% Ethyl acetate: pet ether) to afford O-alkylated product 13b (188 mg, 59%) as brown coloured oil.

Data for 13b: $^1$H NMR (400 MHz, CHLOROFORM-d) δ=7.44 (d, J=7.8 Hz, 1H), 7.35 (d, J=7.8 Hz, 1H), 7.25-7.16 (m, 1H), 4.61 (d, J=4.6 Hz, 2H), 4.45-4.36 (m, 1H), 4.22-4.13 (m, 2H), 4.10-4.00 (m, 1H), 3.85 (dd, J=3.9, 10.5 Hz, 1H), 3.78 (dd, J=5.4, 10.5 Hz, 1H), 1.91 (t, J=6.0 Hz, 2H), 1.46 (s, 3H), 1.41 (s, 3H), 1.30 (s, 3H), 1.29 (s, 3H), 0.84 (s, 9H), 0.04 (s, 3H), 0.03 (s, 3H); $^{13}$C NMR (101 MHz, CHLOROFORM-d) δ=153.1, 150.1, 133.3, 130.6, 126.7, 125.2, 123.4, 123.3, 109.7, 78.3, 76.2, 67.3, 63.4, 38.6, 34.7, 31.3, 29.7, 25.8, 21.6, 18.2, −5.5, −5.6.

Example 13(b): Synthesis of 2-(4S,5S)-5-(hydroxymethyl)-2,2-dimethyl-1,3-dioxolan-4-yl)methoxy)-7,7-dimethyl-6,7-dihydro-3H,5H-pyrido[1,2,3-de]quinoxalin-3-one (13c)

A solution of 2-(((4S,5S)-5-(((tert-butyldimethylsilyl)oxy)methyl)-2,2-dimethyl-1,3-dioxolan-4-yl)methoxy)-7,7-dimethyl-6,7-dihydro-3H,5H-pyrido[1,2,3-de]quinoxalin-3-one 13b (60 mg, 0.12 mmol) in THF 5 mL was added tetra-n-butyl ammonium fluoride TBAF (1M Solution in THF) (0.147 mL, 0.14 mmol) and kept stirring at room temperature for 2 hrs the reaction was monitored by TLC. The reaction mixture diluted with water and extracted with ethyl acetate. Organic layer was then concentrated under reduced pressure, and purified by column chromatography (20% Ethyl acetate: dichloromethane) to afford compound 13c (30 mg, 66%) as colourless gum.

Data for 13c: $^1$H NMR (400 MHz, CHLOROFORM-d) δ=7.50-7.45 (m, 1H), 7.41-7.36 (m, 1H), 7.27-7.22 (m, 1H), 4.74 (dd, J=4.6, 11.2 Hz, 1H), 4.51 (dd, J=5.9, 11.2 Hz, 1H), 4.36-4.29 (m, 1H), 4.23-4.17 (m, 2H), 4.14 (td, J=4.3, 8.3 Hz, 1H), 3.95-3.77 (m, 2H), 2.63 (br. s., 1H), 1.94 (t, J=6.1 Hz, 2H), 1.48 (s, 3H), 1.45 (s, 3H), 1.38 (s, 6H); $^{13}$C NMR (101 MHz, CHLOROFORM-d) δ=152.8, 150.3, 133.6, 130.6, 126.8, 125.4, 125.3, 123.7, 123.7, 109.7, 79.9, 75.8, 66.9, 62.6, 38.8, 34.7, 31.5, 29.8, 27.0, 26.8.

Example 13: Synthesis of 7,7-dimethyl-2-((2S,3S)-2,3,4-trihydroxybutoxy)-6,7-dihydro-3H,5H-pyrido[1,2,3-de]quinoxalin-3-one (13)

A solution of 2-(((4S,5S)-5-(hydroxymethyl)-2,2-dimethyl-1,3-dioxolan-4-yl)methoxy)-7,7-dimethyl-6,7-dihydro-3H,5H-pyrido[1,2,3-de]quinoxalin-3-one 13c (30 mg, 0.08 mmol) in Acetic acid:Water (1:1) 1 mL and kept stirring for 2 hrs at 60° C. reaction was monitored by TLC. The reaction mixture concentrated under reduced pressure, and purified by column chromatography (5% Methanol: dichloromethane) to afford compound 13 (18 mg, 69%) as colourless gum.

Data for 13: $^1$H NMR (400 MHz, METHANOL-d$_4$) δ=7.50 (d, J=7.8 Hz, 2H), 7.31 (t, J=7.8 Hz, 1H), 4.64-4.43 (m, 2H), 4.29-4.19 (m, 2H), 4.19-4.08 (m, 1H), 3.82-3.52 (m, 3H), 2.03-1.96 (m, 2H), 1.42 (s, 6H); $^{13}$C NMR (101 MHz, CHLOROFORM-d) δ=154.5, 152.4, 135.6, 132.6, 127.9, 126.4, 125.3, 125.1, 73.2, 70.6, 70.3, 64.4, 40.2, 35.9, 32.7, 30.0.

Example 14

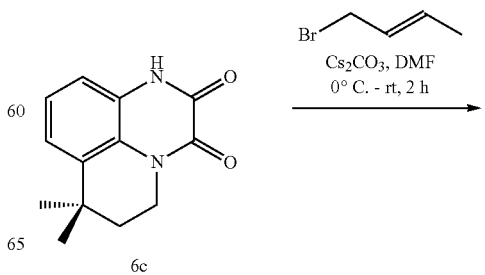

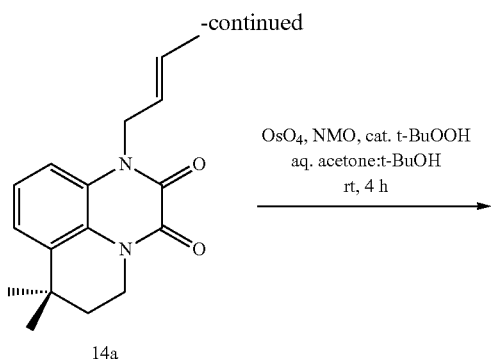

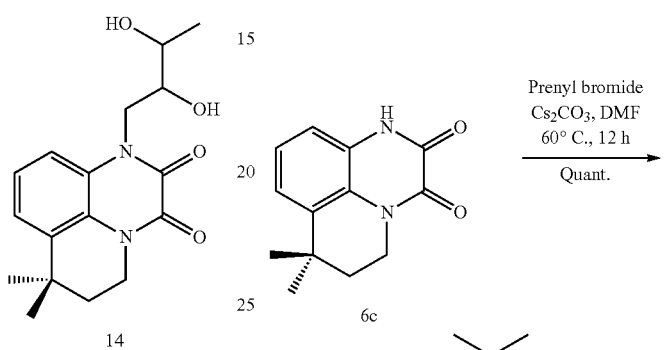

Example 14(a): Synthesis of (E)-1-(but-2-en-1-yl)-7,7-dimethyl-6,7-dihydro-1H,5H-pyrido[1,2,3-de]quinoxaline-2,3-dione (14a)

To a solution of 7,7-dimethyl-6,7-dihydro-1H,5H-pyrido[1,2,3-de]quinoxaline-2,3-dione 6c (200 mg, 0.86 mmol) in dry DMF (10 mL) was added caesium carbonate (367 mg, 1.13 mmol) followed by crotyl bromide (0.108 mL, 1.04 mmol) was then added and stirred for 4 hrs at room temperature. The reaction mixture was added to cold water (30 mL) and extracted with ethyl acetate (3×30 mL) and the combined organic layers were washed with water, brine, then dried over $Na_2SO_4$, filtered and concentrated in vacuo, and purified by column chromatography (30% Ethyl acetate: pet ether) to afford compound 14a (205 mg, 83%) as yellow sticky solid.

Data for 14a: $^1$H NMR (400 MHz, CHLOROFORM-d) δ=7.30-7.08 (m, 3H), 5.84-5.69 (m, 1H), 5.65-5.46 (m, 1H), 4.80 (d, J=5.6 Hz, 2H), 4.19 (t, J=6.36 Hz, 2H), 1.92 (t, J=6.36 Hz, 2H), 1.69 (d, J=6.4 Hz, 3H), 1.39 (s, 6H); $^{13}$C NMR (101 MHz, CHLOROFORM-d) δ=153.8, 153.7, 134.7, 130.1, 128.9, 126.6, 123.7, 123.4, 121.2, 113.4, 45.0, 39.0, 34.5, 32.0, 29.9, 17.7.

Example 14: Synthesis of 1-(2,3-dihydroxybutyl)-7,7-dimethyl-6,7-dihydro-1H,5H-pyrido[1,2,3-de]quinoxaline-2,3-dione (14)

A solution of (E)-1-(but-2-en-1-yl)-7,7-dimethyl-6,7-dihydro-1H,5H-pyrido[1,2,3-de]quinoxaline-2,3-dione 14a (120 mg, 0.48 mmol) in acetone:water:t-BuOH (4 mL, 7:2:1) was treated with NMO (224 mg, 1.93 mmol), osmium tetraoxide (2.5% sol. in t-BuOH) (0.049 mL, 0.004 mmol) and cat. t-BuOOH and stirred for 4 hrs at room temperature. The reaction mixture was added to cold solution of $NaHSO_4$ and extracted with ethyl acetate (3×30 mL) and washed with water, brine and the combined organic layers were dried over $Na_2SO_4$, filtered and concentrated in vacuo. The resultant residue was purified by flash chromatography on silica (5% MeOH: $CH_2Cl_2$) to afford hydroxylated compound 14 (96 mg, 71%) as colourless oil.

Data for 14: $^1$H NMR (400 MHz, CHLOROFORM-d) δ=7.50 (d, J=8.3 Hz, 1H), 7.35 (d, J=7.8 Hz, 1H), 7.25 (t, J=8.1 Hz, 1H), 4.47 (dd, J=8.8, 14.2 Hz, 1H), 4.28 (dd, J=3.9, 14.2 Hz, 1H), 4.18-4.12 (t, J=6.36 Hz, 2H), 3.91-3.79 (m, 2H), 1.97-1.92 (t, J=6.36 Hz, 2H), 1.40 (s, 3H), 1.38 (s, 3H), 1.27 (d, J=6.4 Hz, 3H); $^{13}$C NMR (101 MHz, METHANOL-$d_4$) δ=156.6, 155.6, 136.4, 128.6, 125.2, 124.1, 122.9, 115.6, 73.2, 69.5, 47.6, 40.4, 35.6, 33.1, 30.4, 30.4, 19.2.

Example 15

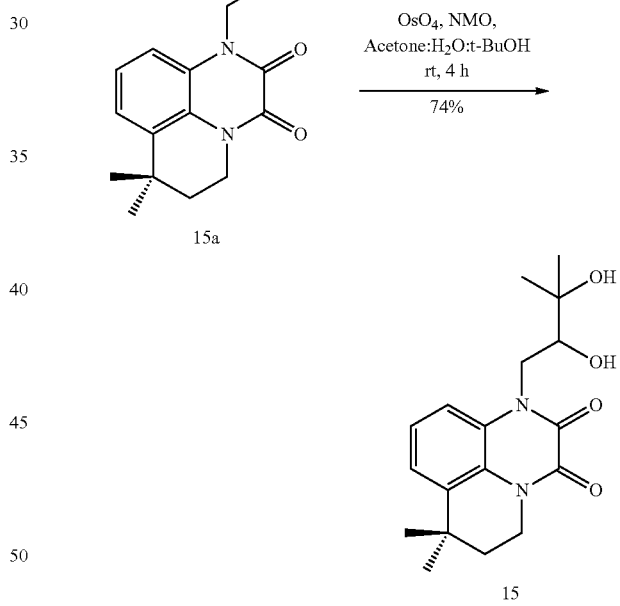

Example 15(a): Synthesis of 7,7-dimethyl-1-(3-methylbut-2-en-1-yl)-6,7-dihydro-1H, 5H-pyrido[1,2,3-de]quinoxaline-2,3-dione (15a)

To a solution of 7,7-dimethyl-6,7-dihydro-1H,5H-pyrido[1,2,3-de]quinoxaline-2,3-dione 6c (100 mg, 0.43 mmol) in dry DMF (5 mL) was added caesium carbonate (169 mg, 0.52 mmol) followed by prenyl bromide (0.077 mL, 0.52 mmol) was then added and stirred for 4 hrs at room temperature. The reaction mixture was added to cold water (30 mL) and extracted with ethyl acetate (3×30 mL) and the combined organic layers were washed with water, brine, then dried over $Na_2SO_4$, filtered and concentrated in vacuo, and purified by column chromatography (30% Ethyl acetate: pet ether) to afford compound 15a (122 mg, 94%) as yellow sticky solid.

Data for 15a: $^1$H NMR (400 MHz, CHLOROFORM-d) δ=7.30-7.17 (m, 2H), 7.09 (d, J=8.1 Hz, 1H), 5.19 (t, J=6.2 Hz, 1H), 4.87 (d, J=6.4 Hz, 2H), 4.20 (t, J=6.3 Hz, 2H), 1.96-1.91 (t, J=6.1 Hz, 2H), 1.89 (s, 3H), 1.74 (s, 3H), 1.40 (s, 6H); $^{13}$C NMR (101 MHz, METHANOL-d$_4$) δ=153.9, 153.8, 137.3, 134.8, 126.6, 123.7, 122.7, 121.1, 118.0, 113.2, 41.8, 39.0, 34.5, 32.0, 29.9, 25.6, 18.4.

Example 15: Synthesis of 1-(2,3-dihydroxy-3-methylbutyl)-7,7-dimethyl-6,7-dihydro-1H,5H-pyrido[1,2,3-de]quinoxaline-2,3-dione (15)

A solution of 7,7-dimethyl-1-(3-methylbut-2-en-1-yl)-6,7-dihydro-1H,5H-pyrido[1,2,3-de]quinoxaline-2,3-dione 15a (112 mg, 0.37 mmol) in acetone:t-BuOH (2 mL, 8:2) was treated with 50% aq. NMO (0.34 mL, 1.48 mmol), osmium tetraoxide (2.5% sol. in t-BuOH) (0.037 mL, 0.003 mmol) and cat. t-BuOOH and stirred for 4 h at room temperature. The reaction mixture was added to cold solution of NaHSO$_4$ and extracted with ethyl acetate (3×30 mL) and washed with water, brine and the combined organic layers were dried over Na$_2$SO$_4$, filtered and concentrated in vacuo. The resultant residue was purified by flash chromatography on silica (5% MeOH: CH$_2$Cl$_2$) to afford hydroxylated compound 15 (52 mg, 41%) as colourless oil.

Data for 15: $^1$H NMR (400 MHz, METHANOL-d$_4$) δ=7.48 (d, J=8.3 Hz, 1H), 7.34 (d, J=7.6 Hz, 1H), 7.25 (t, J=8.1 Hz, 1H), 4.54 (dd, J=10.1, 14.1 Hz, 1H), 4.34 (dd, J=2.0, 14.2 Hz, 1H), 4.21-4.10 (m, 2H), 3.81 (dd, J=2.0, 9.8 Hz, 1H), 1.95 (t, J=6.2 Hz, 2H), 1.40 (s, 3H), 1.38 (s, 3H), 1.3 (s, 6H); $^{13}$C NMR (101 MHz, CHLOROFORM-d) δ=156.7, 155.6, 136.4, 128.7, 125.1, 124.1, 122.8, 115.7, 76.3, 73.5, 46.8, 40.4, 35.6, 33.1, 30.4, 30.3, 27.0, 24.8.

Example 16

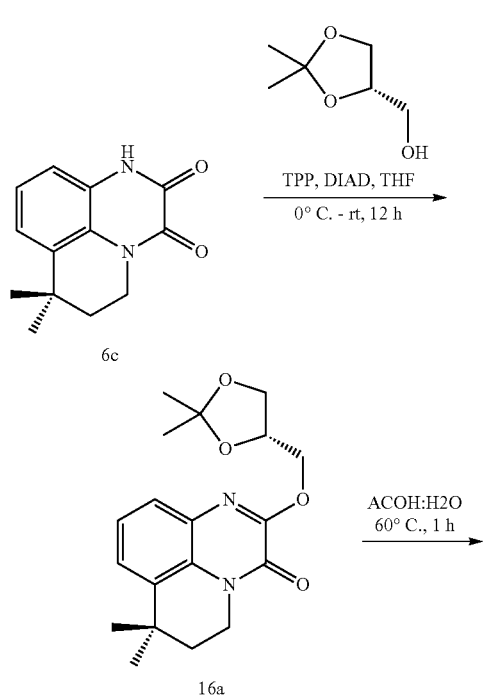

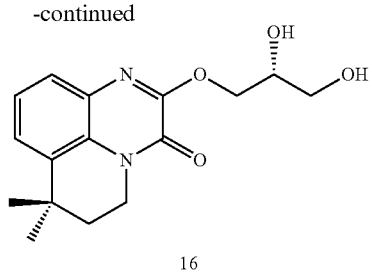

Example 16(a): Synthesis of (S)-2-((2,2-dimethyl-1,3-dioxolan-4-yl)methoxy)-7,7-dimethyl-6,7-dihydro-3H,5H-pyrido[1,2,3-de]quinoxalin-3-one (16a)

To a solution of 7,7-dimethyl-6,7-dihydro-1H,5H-pyrido[1,2,3-de]quinoxaline-2,3-dione 6c (100 mg, 0.43 mmol) in dry THF (5 mL) was added triphenylphosphine (262 mg, 1.00 mmol), (S)-(2,2-dimethyl-1,3-dioxolan-4-yl)methanol (68 mg, 0.51 mmol) and DIAD (0.194 mL, 1.00 mmol) sequentially and stirred for 12 hrs at room temperature. The reaction mixture was diluted with water 10 mL) and extracted with ethyl acetate (3×10 mL), and the organic layer was washed successively with water and brine, dried over Na$_2$SO$_4$, and concentrated in vacuo. The residue was purified by flash silica gel column chromatography (10% EtOAc: CH$_2$Cl$_2$) to afford O-alkylated product 16a (82 mg, 64%) as brown coloured oil.

Data for 16a: $[α]_D^{25}$=10.2° (c 0.6, CHCl3); $^1$H NMR (400 MHz, CHLOROFORM-d) δ=7.50-7.44 (m, 1H), 7.37 (dd, J=1.3, 7.7 Hz, 1H), 7.24 (t, J=7.8 Hz, 1H), 4.65-4.53 (m, 2H), 4.47-4.39 (m, 1H), 4.22-4.13 (m, 3H), 3.97 (dd, J=5.5, 8.7 Hz, 1H), 1.93 (t, J=6.1 Hz, 2H), 1.49 (s, 3H), 1.39 (s, 3H); 1.38 (s, 6H); $^{13}$C NMR (101 MHz, METHANOL-d$_4$) δ=153.0, 150.2, 133.5, 130.6, 126.8, 125.3, 123.6, 123.5, 109.7, 73.3, 67.4, 67.1, 38.7, 34.7, 31.4, 29.7, 26.8, 25.4.

Example 16: Synthesis of (R)-2-(2,3-dihydroxypropoxy)-7,7-dimethyl-6,7-dihydro-3H,5H-pyrido[1,2,3-de]quinoxalin-3-one (16)

A solution of (S)-2-((2,2-dimethyl-1,3-dioxolan-4-yl)methoxy)-7,7-dimethyl-6,7-dihydro-3H,5H-pyrido[1,2,3-de]quinoxalin-3-one 16a (80 mg, 0.23 mmol) in acetic acid:water (1:1; 1 mL) was stirred for 3 h at 60° C. The reaction mixture was concentrated under reduced pressure, and purified by flash column chromatography (10% MeOH: CH$_2$Cl$_2$) to give compound 16 (38 mg, 54%) as colourless sticky solid.

Data for 16: $[α]_D^{25}$=-0.47° (c 4.6, MeOH); $^1$H NMR (400 MHz, METHANOL-D$_3$) δ=7.42 (t, J=8.7 Hz, 2H), 7.24 (t, J=7.8 Hz, 1H), 4.50 (dd, J=3.7, 11.0 Hz, 1H), 4.36 (dd, J=6.9, 11.0 Hz, 1H), 4.20-4.12 (m, 2H), 4.10-4.00 (m, 1H), 3.68 (d, J=6.0 Hz, 2H), 1.93 (t, J=5.9 Hz, 2H), 1.36 (s, 6H); $^{13}$C NMR (101 MHz, METHANOL-D$_3$) δ=153.9, 152.0, 135.0, 132.0, 127.3, 126.2, 125.1, 124.7, 70.9, 69.8, 63.7, 39.9, 35.5, 32.3, 30.1.

Example 17

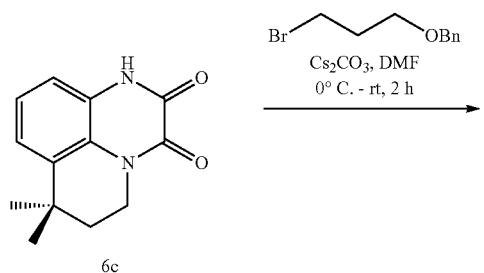

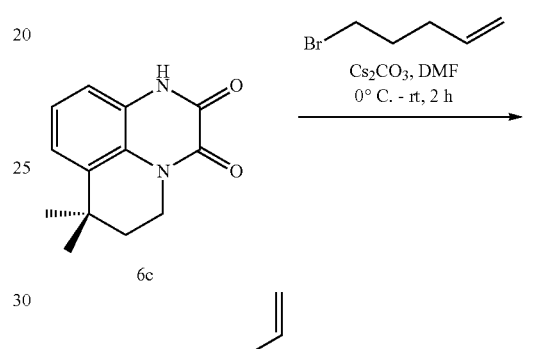

Example 17(a): Synthesis of 1-(3-(benzyloxy)propyl)-7,7-dimethyl-6,7-dihydro-1H,5H-pyrido[1,2,3-de]quinoxaline-2,3-dione (17a)

To a solution of 7,7-dimethyl-6,7-dihydro-1H,5H-pyrido[1,2,3-de]quinoxaline-2,3-dione 6c (200 mg, 0.86 mmol) in dry DMF (5 mL) was added caesium carbonate (339 mg, 1.04 mmol) followed by ((3-bromopropoxy)methyl)benzene (0.288 mg, 1.04 mmol) was then added and stirred for 4 hrs at room temperature. The reaction mixture was added to cold water (20 mL) and extracted with ethyl acetate (3×30 mL) and the combined organic layers were washed with water, brine, then dried over Na$_2$SO$_4$, filtered and concentrated in vacuo, and purified by column chromatography (20% Ethyl acetate: pet ether) to afford compound 17a (214 mg, 65%) as yellow sticky solid.

Data for 17a: Confirmed by Mass spectroscopy; M+1=379

Example 17: Synthesis of 1-(3-hydroxypropyl)-7,7-dimethyl-6,7-dihydro-1H,5H-pyrido[1,2,3-de]quinoxaline-2,3-dione (17)

A solution of 1-(3-(benzyloxy)propyl)-7,7-dimethyl-6,7-dihydro-1H,5H-pyrido[1,2,3-de]quinoxaline-2,3-dione 17a (120 mg, 0.31 mmol) in methanol (2 mL) was added Pd/C (10 mg) stirred for 12 hrs at room temperature under hydrogen atmosphere. The reaction mixture was then filtered through celite pad concentrated under reduced pressure, and purified by flash column chromatography (40% EtOAc: CH$_2$Cl$_2$) to give compound 17 (60 mg, 66%) as colorless sticky solid.

Data for 17: $^1$H NMR (400 MHz, CHLOROFORM-d) δ=7.33-7.18 (m, 3H), 4.41 (t, J=6.5 Hz, 2H), 4.24-4.15 (m, 2H), 3.64 (t, J=5.5 Hz, 2H), 3.31 (br. s., 1H), 2.03 (quin, J=6.0 Hz, 2H), 1.98-1.90 (m, 2H), 1.40 (s, 6H); $^{13}$C NMR (101 MHz, CHLOROFORM-d) δ=154.8, 153.4, 135.0, 126.0, 124.0, 122.8, 121.6, 112.9, 58.5, 40.2, 39.1, 34.3, 32.0, 29.9, 29.8.

Example 18

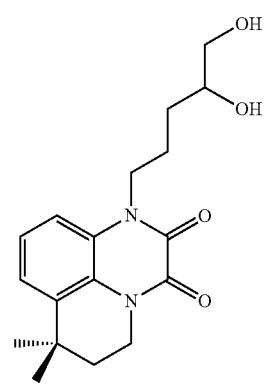

Example 18(a): Synthesis of 7,7-dimethyl-1-(pent-4-en-1-yl)-6,7-dihydro-1H,5H-pyrido[1,2,3-de]quinoxaline-2,3-dione (18a)

To a solution of 7,7-dimethyl-6,7-dihydro-1H,5H-pyrido[1,2,3-de]quinoxaline-2,3-dione 6c (200 mg, 0.86 mmol) in dry DMF (5 mL) was added caesium carbonate (339 mg, 1.04 mmol) followed by 5-bromopent-1-ene (250 mg, 1.04 mmol) was then added and stirred for 4 hrs at room temperature. The reaction mixture was added to cold water (15 mL) and extracted with ethyl acetate (3×30 mL) and the combined organic layers were washed with water, brine, then dried over $Na_2SO_4$, filtered and concentrated in vacuo, and purified by column chromatography (30% Ethyl acetate: pet ether) to afford compound 18a (168 mg, 64%) as yellow sticky solid.

Data for 18a: $^1$H NMR (400 MHz, CHLOROFORM-d) δ=7.45 (d, J=6.9 Hz, 1H), 7.34 (d, J=7.3 Hz, 1H), 7.30-7.16 (m, 1H), 5.93-5.78 (m, 1H), 5.11-4.94 (m, 2H), 4.47 (t, J=6.9 Hz, 2H), 4.22-4.16 (t, J=6.4 Hz, 2H), 2.24 (q, J=7.3 Hz, 2H), 1.98 (quin, J=7.1 Hz, 2H), 1.92 (t, J=6.4 Hz, 2H), 1.37 (s, 6H); $^{13}$C NMR (101 MHz, CHLOROFORM-d) δ=153.5, 150.5, 137.7, 133.4, 131.0, 126.6, 125.1, 123.5, 123.1, 115.1, 66.7, 38.7, 34.7, 31.4, 30.0, 29.7, 27.6

Example 18: Synthesis of 1-(4,5-dihydroxypentyl)-7,7-dimethyl-6,7-dihydro-1H,5H-pyrido[1,2,3-de]quinoxaline-2,3-dione (18)

A solution of 7,7-dimethyl-1-(pent-4-en-1-yl)-6,7-dihydro-1H,5H-pyrido[1,2,3-de]quinoxaline-2,3-dione 18a (150 mg, 0.50 mmol) in acetone:t-BuOH (2 mL, 8:2) was treated with 50% aq. NMO (0.469 mL, 2.00 mmol), osmium tetraoxide (2.5% sol. in t-BuOH) (0.05 mL, 0.005 mmol) and cat. t-BuOOH and stirred for 4 h at room temperature. The reaction mixture was added to cold solution of $NaHSO_4$ and extracted with ethyl acetate (3×30 mL) and washed with water, brine and the combined organic layers were dried over $Na_2SO_4$, filtered and concentrated in vacuo. The resultant residue was purified by flash chromatography on silica (5% MeOH: $CH_2Cl_2$) to afford hydroxylated compound 18 (124 mg, 76%) as colorless oil.

Data for 18: $^1$H NMR (400 MHz, METHANOL-$d_4$) δ=7.46 (d, J=7.8 Hz, 2H), 7.31-7.24 (m, 1H), 4.51-4.47 (m, 2H), 4.21-4.16 (m, 2H), 3.69 (dt, J=4.5, 9.5 Hz, 1H), 3.56-3.45 (m, 2H), 2.12-2.01 (m, 1H), 2.01-1.89 (m, 3H), 1.82-0.1.71 (m, 1H), 1.64-1.50 (m, 1H), 1.40 (s, 6H); $^{13}$C NMR (101 MHz, METHANOL-$d_4$) δ=154.6, 152.2, 135.4, 132.6, 127.7, 126.3, 125.2, 124.8, 73.0, 68.7, 67.5, 40.1, 35.9, 32.6, 31.0, 30.2, 26.0.

Example 19

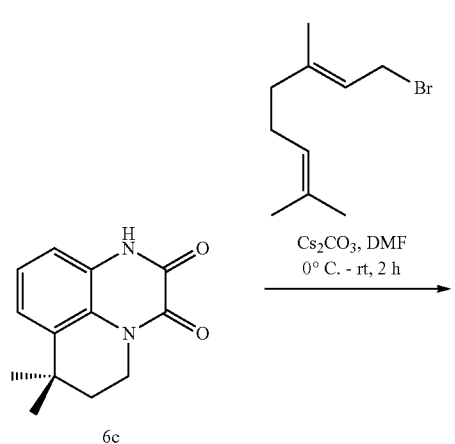

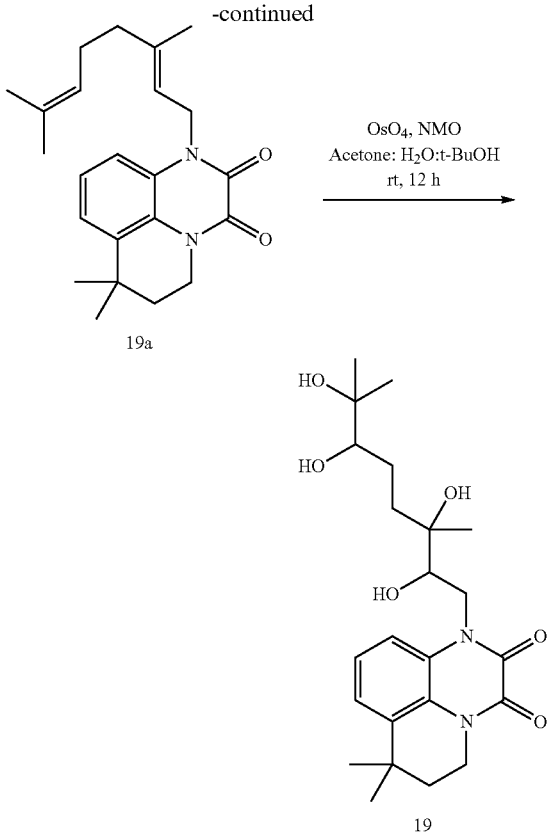

Example 19(a): Synthesis of (E)-1-(3,7-dimethyl-octa-2,6-dien-1-yl)-7,7-dimethyl-6,7-dihydro-1H,5H-pyrido[1,2,3-de]quinoxaline-2,3-dione (19a)

To a solution of 7,7-dimethyl-6,7-dihydro-1H,5H-pyrido[1,2,3-de]quinoxaline-2,3-dione 6c (200 mg, 0.86 mmol) in dry DMF (5 mL) was added caesium carbonate (339 mg, 1.04 mmol) followed by (E)-1-bromo-3,7-dimethylocta-2,6-diene (226 mg, 1.04 mmol) was then added and stirred for 4 hrs at room temperature. The reaction mixture was added to cold water (15 mL) and extracted with ethyl acetate (3×30 mL) and the combined organic layers were washed with water, brine, then dried over $Na_2SO_4$, filtered and concentrated in vacuo, and purified by column chromatography (30% Ethyl acetate: pet ether) to afford compound 19a (172 mg, 53%) as yellow sticky solid.

Data for 19a: $^1$H NMR (400 MHz, CHLOROFORM-d) δ=7.26-7.15 (m, 2H), 7.05 (d, J=8.2 Hz, 1H), 5.14 (t, J=5.7 Hz, 1H), 5.03-4.97 (m, 1H), 4.85 (d, J=5.5 Hz, 2H), 4.17 (t, J=5.9 Hz, 2H), 2.10-1.95 (m, 4H), 1.95-1.88 (m, 2H), 1.85 (s, 3H), 1.60 (s, 3H), 1.55 (s, 3H), 1.37 (s, 6H); $^{13}$C NMR (101 MHz, CHLOROFORM-d) δ=153.8, 153.7, 140.5, 134.7, 131.7, 126.5, 123.7, 123.5, 122.6, 121.1, 117.9, 113.3, 109.9, 41.8, 39.3, 39.0, 34.4, 31.9, 29.9, 26.1, 25.6, 17.6, 16.7

Example 19: Synthesis of 7,7-dimethyl-1-(2,3,6,7-tetrahydroxy-3,7-dimethyloctyl)-6,7-dihydro-1H,5H-pyrido[1,2,3-de]quinoxaline-2,3-dione (19)

A solution of (E)-1-(3,7-dimethylocta-2,6-dien-1-yl)-7,7-dimethyl-6,7-dihydro-1H,5H-pyrido[1,2,3-de]quinoxaline- 2,3-dione 19a (152 mg, 0.49 mmol) in acetone:t-BuOH (3 mL, 8:2) was treated with 50% aq. NMO (0.462 mL, 1.96 mmol), osmium tetraoxide (2.5% sol. in t-BuOH) (0.04 mL, 0.004 mmol) and cat. t-BuOOH and stirred for 4 h at room temperature. The reaction mixture was added to cold solution of NaHSO$_4$ and extracted with ethyl acetate (3×30 mL) and washed with water, brine and the combined organic layers were dried over Na$_2$SO$_4$, filtered and concentrated in vacuo. The resultant residue was purified by flash chromatography on silica (5% MeOH: CH$_2$Cl$_2$) to afford hydroxylated compound 19 (94 mg, 52%) as colourless oil.

Data for 19: $^1$H NMR (400 MHz, CHLOROFORM-d) δ=7.41 (d, J=7.6 Hz, 1H), 7.31-7.12 (m, 2H), 4.49-4.40 (m, 1H), 4.39-4.27 (m, 1H), 4.17-4.04 (m, 2H), 3.83 (d, J=7.3 Hz, 1H), 3.29-3.18 (m, 2H), 1.89 (t, J=6.1 Hz, 3H), 1.73-1.60 (m, 2H), 1.34 (s, 3H), 1.33 (s, 3H), 1.25 (s, 3H), 1.11 (br. s., 6H); $^{13}$C NMR (101 MHz, METHANOL-d$_4$) δ=156.0, 154.8, 135.6, 127.9, 124.8, 123.2, 122.4, 115.0, 79.6, 75.2, 74.7, 73.6, 46.4, 39.9, 35.5, 35.0, 32.6, 30.3, 25.6, 24.7, 22.9.

Example 20

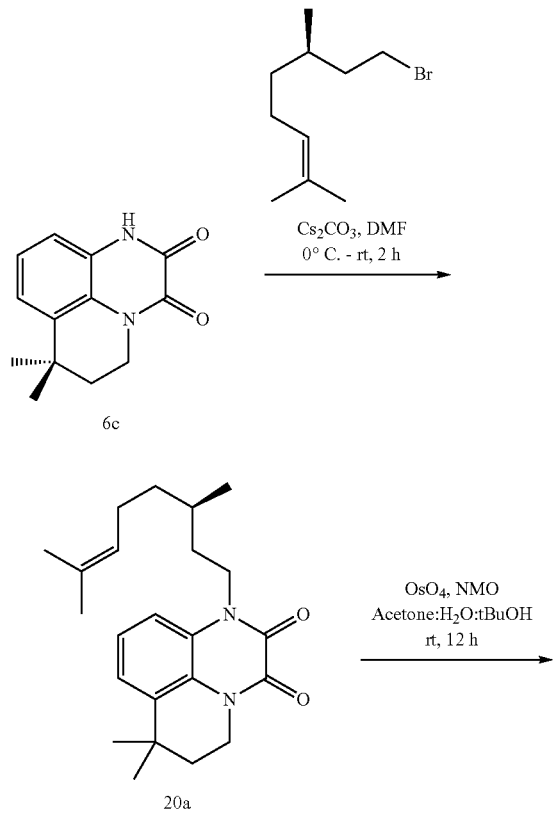

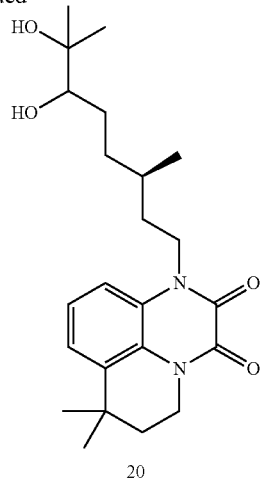

Example 20(a): Synthesis of (R)-1-(3,7-dimethyl-oct-6-en-1-yl)-7,7-dimethyl-6,7-dihydro-1H,5H-pyrido[1,2,3-de]quinoxaline-2,3-dione (20a)

To a solution of 7,7-dimethyl-6,7-dihydro-1H,5H-pyrido[1,2,3-de]quinoxaline-2,3-dione 6c (200 mg, 0.86 mmol) in dry DMF (5 mL) was added caesium carbonate (339 mg, 1.04 mmol) followed by (R)-8-bromo-2,6-dimethyloct-2-ene (323 mg, 1.04 mmol) was then added and stirred for 4 hrs at room temperature. The reaction mixture was added to cold water (15 mL) and extracted with ethyl acetate (3×30 mL) and the combined organic layers were washed with water, brine, then dried over Na$_2$SO$_4$, filtered and concentrated in vacuo, and purified by column chromatography (40% Ethyl acetate: pet ether) to afford compound 20a (152 mg, 47%) as colourless sticky solid.

Example 20: Synthesis of 1-((3R)-6,7-dihydroxy-3,7-dimethyloctyl)-7,7-dimethyl-6,7-dihydro-1H,5H-pyrido[1,2,3-de]quinoxaline-2,3-dione (20)

A solution of (R)-1-(3,7-dimethyloct-6-en-1-yl)-7,7-dimethyl-6,7-dihydro-1H,5H-pyrido[1,2,3-de]quinoxaline-2,3-dione 20a (140 mg, 0.38 mmol) in acetone:t-BuOH (3 mL, 8:2) was treated with 50% aq. NMO (0.356 mL, 1.52 mmol), osmium tetraoxide (2.5% sol. in t-BuOH) (0.03 mL, 0.003 mmol) and cat. t-BuOOH and stirred for 4 h at room temperature. The reaction mixture was added to cold solution of NaHSO$_4$ and extracted with ethyl acetate (3×30 mL) and washed with water, brine and the combined organic layers were dried over Na$_2$SO$_4$, filtered and concentrated in vacuo. The resultant residue was purified by flash chromatography on silica (5% MeOH: CH$_2$Cl$_2$) to afford hydroxylated compound 20 (61 mg, 40%) as colourless oil.

Data for 20: $^1$H NMR (400 MHz, CHLOROFORM-d) δ=7.30-7.18 (m, 2H), 7.15-7.06 (m, 1H), 4.32-4.20 (m, 2H), 4.20-4.13 (m, 2H), 3.42-3.31 (m, 1H), 2.60 (br. s., 3H), 1.95-1.88 (m, 2H), 1.84-1.57 (m, 6H), 1.37 (s, 6H), 1.21 (s, 3H), 1.16 (d, J=5.1 Hz, 3H), 1.03 (dd, J=5.9, 12.5 Hz, 3H); $^{13}$C NMR (101 MHz, CHLOROFORM-d) δ=153.8, 153.7, 135.0, 126.2, 123.9, 122.7, 121.2, 112.8, 78.8, 78.2, 73.1, 73.1, 41.6, 39.0, 34.4, 32.0, 29.9, 28.4, 26.5, 23.1, 19.5.

Example 21

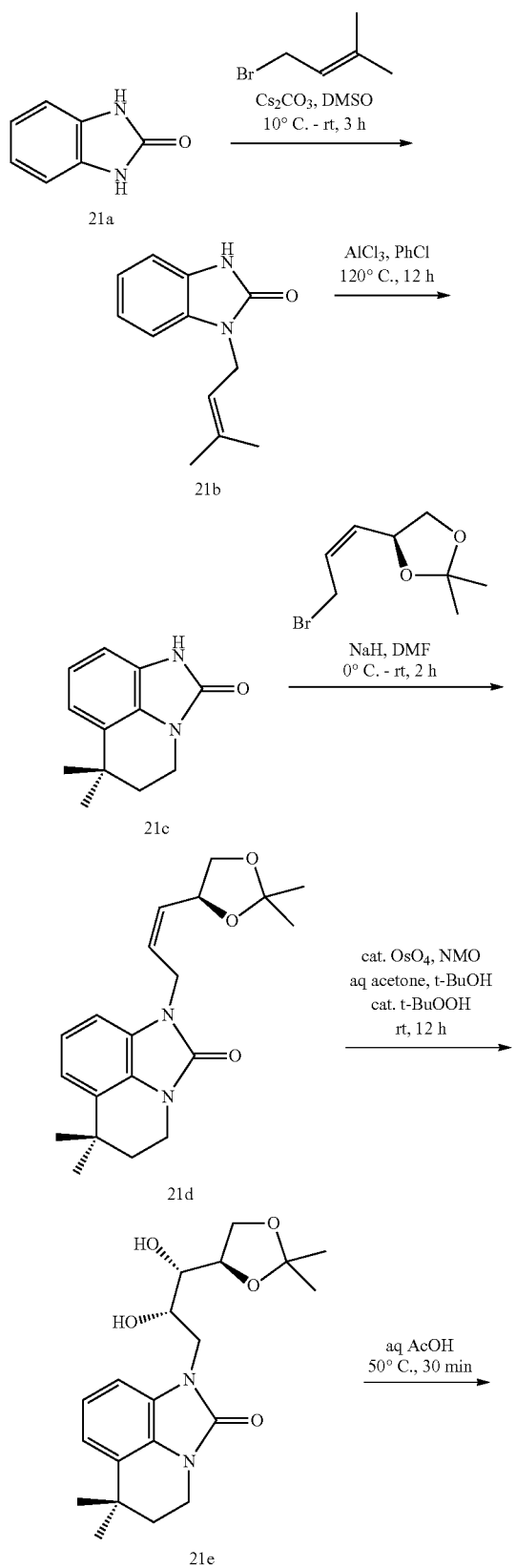

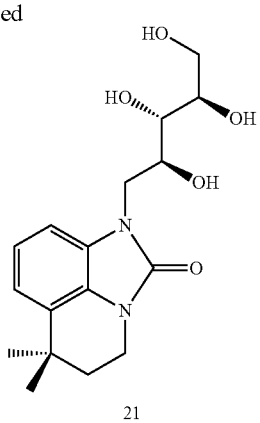

Example 21(a): Synthesis of 1-(3-methylbut-2-en-1-yl)-1,3-dihydro-2H-benzo[d]imidazol-2-one (21b)

To a solution of 1,3-dihydro-2H-benzo[d]imidazol-2-one 21a (2 gm, 0.012 mol) in dry DMSO (40 mL) was added cesium carbonate (4.8 g, 0.014 mol), followed by 3,3-dimethylallyl bromide (1.42 mL, 0.012 mol) diluted in 5 mL of DMSO and kept stirring for 3 hrs at room temperature reaction. The reaction mixture was added to cold water and extracted with ethyl acetate (3×100 mL). The combined organic layer was washed with brine and dried over $Na_2SO_4$, concentrated under reduced pressure, and subjected to flash chromatography over silica gel (40% EtOAc: petroleum ether) to afford mono-alkylated compound 21b (1.1 gm, 38%) as brown solid.

Data for 21b: $^1$H NMR (400 MHz, CHLOROFORM-d) δ=10.57 (br. s., 1H), 7.18-7.11 (m, 1H), 7.10-7.01 (m, 2H), 7.00-6.93 (m, 1H), 5.30 (t, J=6.7 Hz, 1H), 4.53 (d, J=6.5 Hz, 2H), 1.88 (s, 3H), 1.75 (s, 3H); $^{13}$C NMR (101 MHz, CHLOROFORM-d) S=155.7, 136.4, 130.2, 128.2, 121.4, 121.0, 118.9, 109.7, 108.2, 38.8, 25.6, 18.1.

Example 21(b): Synthesis of 6,6-dimethyl-5,6-dihydro-4H-imidazo[4,5,1-ij]quinolin-2(1H)-one (21c)

A dried sealed tube charged with 1-(3-methylbut-2-en-1-yl)-1,3-dihydro-2H-benzo[d]imidazol-2-one 21b (200 mg, 0:775 mmol) and $AlCl_3$ (613 mg, 4.65 mmol) in chlorobenzene (10 mL) was heated up to 120° C. for 12 h. The reaction was quenched by the addition of $H_2O$ (20 mL), then neutralized with saturated aqueous $NaHCO_3$. The reaction mixture was filtered through a pad of Celite® and washed with ethyl acetate. The resulting filtrate was partitioned with ethyl acetate (3×100 mL) and water. The combined organic layers were dried over $Na_2SO_4$, concentrated in vacuo and purified by flash column chromatography over silica gel (30% EtOAc: $CH_2Cl_2$) to afford compound 21c (130 mg, 65%) as brown solid.

Data for 21c: $^1$H NMR (500 MHz, CHLOROFORM-d) δ=10.75 (br. s., 1H), 7.06-6.89 (m, 3H), 3.94 (t, J=5.6 Hz, 2H), 1.92 (t, J=5.6 Hz, 2H), 1.36 (s, 6H); $^{13}$C NMR (126 MHz, CHLOROFORM-d) δ=155.1, 128.4, 126.5, 126.1, 121.2, 115.9, 107.2, 36.6, 36.0, 31.6, 28.5.

Example 21(c): Synthesis of (S,Z)-1-(3-(2,2-dimethyl-1,3-dioxolan-4-yl)allyl)-6,6-dimethyl-5,6-dihydro-4H-imidazo[4,5,1-ij]quinolin-2(1H)-one (21d)

A solution of 6,6-dimethyl-5,6-dihydro-4H-imidazo[4,5,1-ij]quinolin-2(1H)-one 21c (70 mg, 0.27 mmol) in dry DMF (1 mL) was added drop wise to pre-cooled (0° C.) suspension of sodium hydride (60% dispersion in mineral oil, 27 mg, 0.67 mmol) in 2 mL of DMF. The reaction mixture was allowed to warm to room temperature and stirred for 20 mins. (S,Z)-4-(3-bromoprop-1-en-1-yl)-2,2-dimethyl-1,3-dioxolane (119 mg, 0.54 mmol), dissolved in dry DMF, was then added drop wise at 0° C. and stirred for 2 h at room temperature. The reaction mixture was added to cold water (10 mL) and extracted with ethyl acetate (3×10 mL) and the combined organic layers were washed with water, brine, then dried over $Na_2SO_4$, filtered and concentrated in vacuo, and purified by column chromatography (30% EtOAc: $CH_2Cl_2$) to afford compound 21d (80 mg, 74%) as colourless oil.

Data for 21d: $[\alpha]_D^{25}$=−0.83° (c 0.2, $CHCl_3$); $^1$H NMR (400 MHz, CHLOROFORM-d) δ=7.05-6.97 (m, 2H), 6.85 (dd, J=1.8, 6.9 Hz, 1H), 5.77-5.63 (m, 2H), 5.13-5.04 (m, 1H), 4.76-4.67 (m, 1H), 4.56-4.46 (m, 1H), 4.20 (dd, J=6.4, 8.2 Hz, 1H), 3.90 (t, J=5.95 Hz, 2H), 3.62 (t, J=7.8 Hz, 1H), 1.90 (t, J=5.95 Hz, 2H), 1.46 (s, 3H), 1.45 (s, 3H), 1.35 (s, 6H); $^{13}$C NMR (101 MHz, CHLOROFORM-d) δ=152.9, 130.9, 128.5, 128.4, 127.4, 125.1, 120.9, 116.3, 109.5, 105.5, 71.7, 69.4, 38.3, 36.6, 36.3, 31.8, 28.5, 26.7, 25.9.

Example 21(d): Synthesis of 1-((2S,3S)-3-((R)-2,2-dimethyl-1,3-dioxolan-4-yl)-2,3-dihydroxypropyl)-6,6-dimethyl-5,6-dihydro-4H-imidazo[4,5,1-ij]quinolin-2(1H)-one (21e)

A solution of (S,Z)-1-(3-(2,2-dimethyl-1,3-dioxolan-4-yl) allyl)-6,6-dimethyl-5,6-dihydro-4H-imidazo[4,5,1-ij]quinolin-2(1H)-one 21d (80 mg, 0.20 mmol) in acetone:water:t-BuOH (5 mL, 7:2:1) was treated with NMO (94 mg, 1.30 mmol), osmium tetraoxide (2.5% sol. in t-BuOH) (0.4 mL, 0.040 mmol) and cat. t-BuOOH and stirred for 12 h at room temperature. The reaction mixture was added to cold solution of $NaHSO_4$ and extracted with ethyl acetate (3×30 mL) and washed with water, brine and the combined organic layers were dried over $Na_2SO_4$, filtered and concentrated in vacuo. The resultant residue was purified by flash chromatography on silica (5% MeOH: $CH_2Cl_2$) to afford hydroxylated compound 37 (68 mg, 79%) as colourless oil.

Data for 21e: $[\alpha]_D^{25}$=−51° (c 6.0, $CHCl_3$); $^1$H NMR (500 MHz, CHLOROFORM-d) δ=7.11-6.97 (m, 3H), 5.33 (br. s., 1H), 4.38-4.28 (m, 1H), 4.22-4.16 (m, 2H), 4.03-3.84 (m, 6H), 3.32 (t, J=8.1 Hz, 1H), 2.00-1.86 (m, 2H), 1.41-1.30 (m, 12H); $^{13}$C NMR (126 MHz, CHLOROFORM-d) δ=155.0, 129.2, 128.6, 124.9, 121.5, 116.6, 109.8, 107.3, 78.6, 75.0, 70.6, 68.2, 44.1, 36.5, 36.5, 31.7, 28.6, 28.5, 26.5, 25.0.

Example 21: Synthesis of 6,6-dimethyl-1-((2S,3S,4R)-2,3,4,5-tetrahydroxypentyl)-5,6-dihydro-4H-imidazo[4,5,1-ij]quinolin-2(1H)-one (21)

A solution of 1-((2S,3S)-3-((R)-2,2-dimethyl-1,3-dioxolan-4-yl)-2,3-dihydroxypropyl)-6,6-dimethyl-5,6-dihydro-4H-imidazo[4,5,1-ij]quinolin-2(1H)-one 21e (68 mg, 0.15 mmol) in acetic acid:water (1:1; 1 mL) was stirred for 30 min at 50° C. The reaction mixture was then concentrated in vacuo, and purified by flash chromatography on $SiO_2$ (10% MeOH: $CH_2Cl_2$) to afford compound 21 (45 mg, 66%) as yellow solid.

Data for 21: $^1$H NMR (400 MHz, METHANOL-$D_4$) δ=7.15-6.91 (m, 3H), 4.15-4.02 (m, 3H), 3.89 (t, J=5.5 Hz, 2H), 3.82-3.74 (m, 2H), 3.70-3.57 (m, 2H), 1.92 (t, J=5.5 Hz, 2H), 1.34 (s, 6H); $^{13}$C NMR (101 MHz, METHANOL- $D_3$) δ=155.8, 130.1, 129.9, 126.3, 122.7, 117.6, 108.0, 74.4, 74.4, 72.5, 64.8, 45.4, 37.9, 37.6, 32.9, 29.0;

Example 22

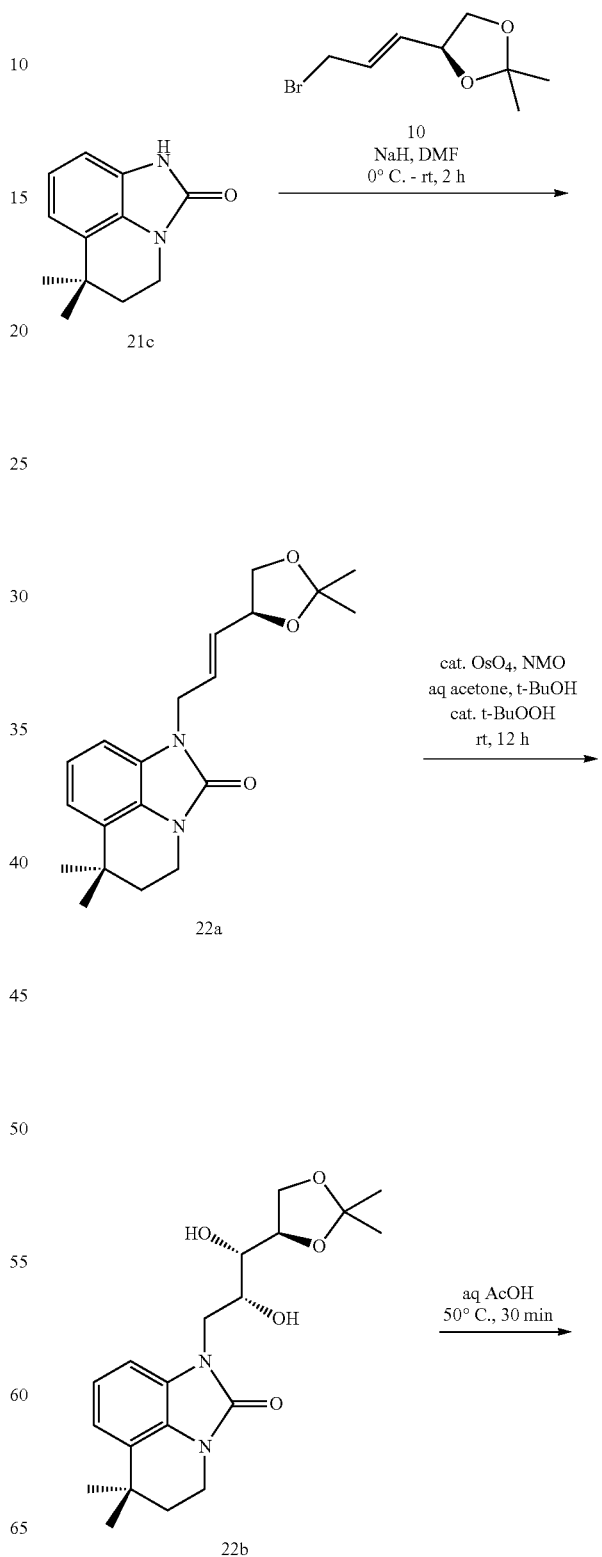

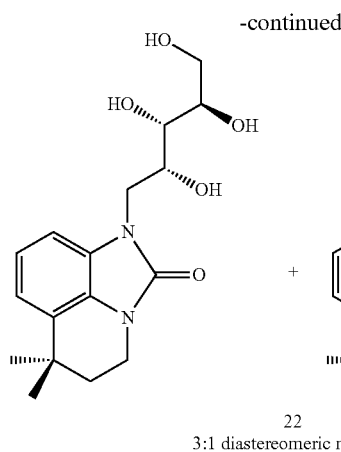

22
3:1 diastereomeric mixture

Example 22(a): Synthesis of (S,E)-1-(3-(2,2-dimethyl-1,3-dioxolan-4-yl)allyl)-6,6-dimethyl-5,6-dihydro-4H-imidazo[4,5,1-ij]quinolin-2(1H)-one (22a)

A solution of 6,6-dimethyl-5,6-dihydro-4H-imidazo[4,5,1-ij]quinolin-2(1H)-one 21c (60 mg, 0.23 mmol) in dry DMF (1 mL) was added dropwise to pre-cooled suspension of sodium hydride (60% dispersion in mineral oil, 23 mg, 0.58 mmol) in 1 mL of DMF. The cooling bath was then removed, and the flask was allowed to warm to room temperature and stirred for 20 mins. (S,E)-4-(3-bromoprop-1-en-1-yl)-2,2-dimethyl-1,3-dioxolane (113 mg, 0.51 mmol), dissolved in dry DMF, was added drop wise at 0° C. and stirred for 2 h at room temperature, then reaction mixture was added to cold water and extracted with ethyl acetate (3×10 mL). The combined organics were dried over Na$_2$SO$_4$, filtered and concentrated in vacuo. The resultant residue was purified by flash chromatography on SiO2 (30% EtOAc: CH$_2$Cl$_2$) to afford compound 22a (52 mg, 65%) as brown gummy mass.

Data for 22a: $[\alpha]_D^{25}$=+1.98° (c=0.2, CHCl$_3$); $^1$H NMR (500 MHz, CHLOROFORM-d) δ=7.03-6.94 (m, 2H), 6.80 (dd, J=2.0, 6.6 Hz, 1H), 5.90 (td, J=5.5, 15.6 Hz, 1H), 5.73 (dd, J=7.0, 15.6 Hz, 1H), 4.56-4.41 (m, 3H), 4.07 (dd, J=6.3, 8.1 Hz, 1H), 3.94-3.85 (m, 2H), 3.57 (t, J=7.8 Hz, 1H), 1.94-1.87 (m, 2H), 1.41 (s, 3H), 1.37 (s, 3H), 1.36 (s, 6H); $^{13}$C NMR (126 MHz, CHLOROFORM-d) δ=153.0, 130.7, 128.4, 128.0, 127.6, 125.1, 120.9, 116.3, 109.4, 105.7, 76.1, 69.3, 42.4, 36.6, 36.3, 31.8, 28.5, 26.6, 25.8.

Example 22(b): Synthesis of 1-((2R,3S)-3-((R)-2,2-dimethyl-1,3-dioxolan-4-yl)-2,3-dihydroxypropyl)-6,6-dimethyl-5,6-dihydro-4H-imidazo[4,5,1-ij]quinolin-2(1H)-one (22b)

A solution of (S,E)-1-(3-(2,2-dimethyl-1,3-dioxolan-4-yl)allyl)-6,6-dimethyl-5,6-dihydro-4H-imidazo[4,5,1-ij]quinolin-2(1H)-one 22a (50 mg, 0.12 mmol) in acetone:water:$^t$BuOH (2 mL, 7:2:1) was treated with NMO (58 mg, 0.502 mmol), osmium tetraoxide (2.5% sol. in $^t$BuOH) (0.255 mL, 0.0251 mmol) and cat. t-BuOOH at room temperature and stirred for 12 hrs. The reaction mixture was added to cold sol of NaHSO$_4$ and extracted with ethyl acetate (3×10 mL) and washed with water, brine. The combined organics were dried over Na$_2$SO$_4$, filtered and concentrated in vacuo. The resultant residue was purified by flash chromatography on SiO$_2$ (5% MeOH: CH$_2$Cl$_2$) to afford compound 22b (32 mg, 66%, 3:1 inseparable diastereomers) as yellow sticky solid.

Data for 22b: $^1$H NMR (400 MHz, CHLOROFORM-d) δ=7.12-6.89 (m, 3H), 4.35-4.25 (m, 1H), 4.25-3.96 (m, 6H), 3.96-3.81 (m, 2H), 3.60-3.37 (m, 1H), 3.37-3.24 (m, 1H), 1.96-1.88 (m, 2H), 1.37 (s, 3H), 1.36 (s, 3H), 1.32 (s, 3H), 1.29 (s, 3H); $^{13}$C NMR (101 MHz, CHLOROFORM-d) δ=154.4, 128.9, 127.8, 125.0, 121.5, 116.7, 109.2, 105.6, 75.4, 71.5, 69.0, 67.2, 44.2, 36.5, 36.5, 31.7, 28.6, 28.5, 26.7, 25.1.

Note: Minor peaks in NMR ($^1$H and $^{13}$C) which could not be cleanly distinguished, corresponds to other diastereomer.

Example 22: Synthesis of 6,6-dimethyl-1-((2R,3S,4R)-2,3,4,5-tetrahydroxypentyl)-5,6-dihydro-4H-imidazo[4,5,1-ij]quinolin-2(1H)-one (22)

A solution of 1-((2R,3S)-3-((R)-2,2-dimethyl-1,3-dioxolan-4-yl)-2,3-dihydroxypropyl)-6,6-dimethyl-5,6-dihydro-4H-imidazo[4,5,1-ij]quinolin-2(1H)-one 22b (25 mg, 0.057 mmol) in Acetic acid:Water (1:1) 1 mL and kept stirring for 3 h at 60° C. reaction was monitored by TLC. The reaction mixture concentrated under reduced pressure, and purified by column chromatography (10% MeOH: CH$_2$Cl$_2$) to afford compound 22 (15 mg, 68%, 3:1 inseparable diastereomers) as colourless gum.

Data for 22: $^1$H NMR (400 MHz, MeOD-d$_4$) δ=7.12-6.89 (m, 3H), 4.26 (t, J=6.8 Hz, 1H), 4.15-3.97 (m, 2H), 3.89 (t, J=5.9 Hz, 2H), 3.84-3.77 (m, 1H), 3.75-3.56 (m, 2H), 3.43 (d, J=8.5 Hz, 1H), 1.92 (t, J=5.9 Hz, 2H), 1.35 (s, 6H); $^{13}$C NMR (101 MHz, METHANOL-d$_4$) δ=155.5, 130.2, 129.7, 126.3, 122.8, 117.7, 107.6, 72.8, 72.5, 69.4, 65.2, 45.7, 37.9, 37.6, 32.9, 29.0.

Note: Minor peaks in NMR ($^1$H and $^{13}$C) which could not be cleanly distinguished, corresponds to other diastereomer.

Example 23

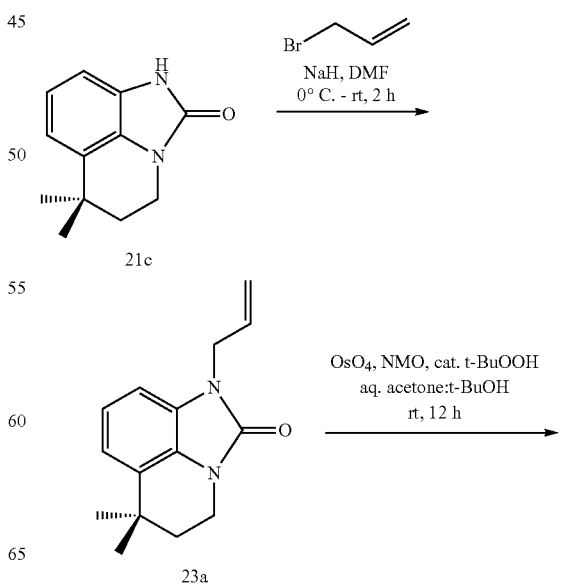

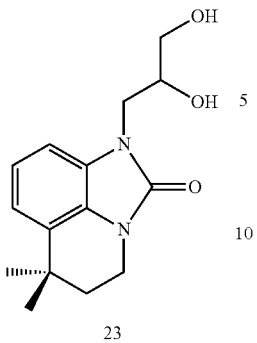

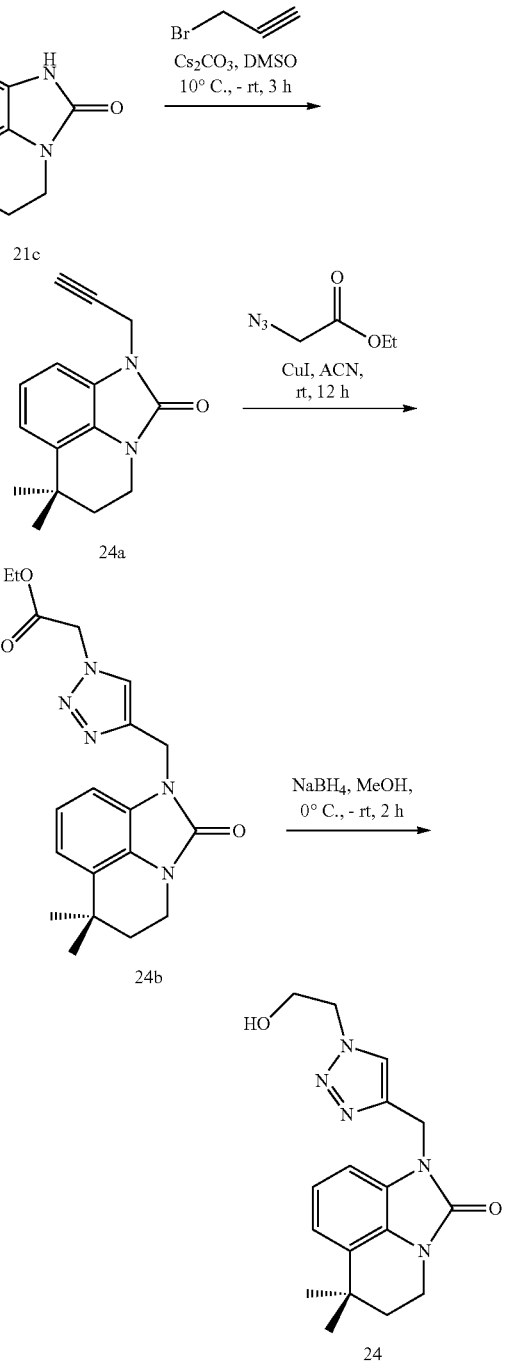

Example 23(a): Synthesis of 1-allyl-6,6-dimethyl-5,6-dihydro-4H-imidazo[4,5,1-ij]quinolin-2(1H)-one (23a)

A solution of 6,6-dimethyl-5,6-dihydro-4H-imidazo[4,5,1-ij]quinolin-2(1H)-one 21c (30 mg, 0.11 mmol) in dry DMF (1 mL) was added drop wise to a pre-cooled suspension of sodium hydride (60% dispersion in mineral oil, 9.2 mg, 0.23 mmol) in 1 mL of DMF. Then cooling bath was removed, and the flask was allowed to warm to room temperature and stirred for 20 mins. Allyl bromide (12 µl, 0.139 mmol) was then added drop wise at 0° C. and stirred for 2 hrs at room temperature. The reaction was quenched by the addition of $H_2O$ (5 mL) and extracted with ethyl acetate (3×10 mL). The combined organics were dried over $Na_2SO_4$, filtered and concentrated in vacuo. The resultant residue was purified by flash chromatography on $SiO_2$ (30% EtOAc: $CH_2Cl_2$) to afford compound 23a (26 mg, 76%) as colourless oil.

Data for 23a: $^1H$ NMR (400 MHz, CHLOROFORM-d) δ=7.09-6.89 (m, 2H), 6.81 (dd, J=2.1, 6.5 Hz, 1H), 5.98-5.75 (m, 1H), 5.33-5.12 (m, 2H), 4.50 (d, J=6.8 Hz, 2H), 3.91 (t, J=5.87 Hz, 2H), 1.90 (t, J=5.95 Hz, 2H), 1.35 (s, 6H); $^{13}C$ NMR (101 MHz, CHLOROFORM-d) δ=153.0, 132.3, 128.2, 127.6, 125.1, 120.7, 117.4, 116.1, 105.7, 43.5, 36.6, 36.2, 31.7, 28.5.

Example 23: Synthesis of 1-(2,3-dihydroxypropyl)-6,6-dimethyl-5,6-dihydro-4H-imidazo[4,5,1-ij]quinolin-2(1H)-one (23)

A solution of 1-allyl-6,6-dimethyl-5,6-dihydro-4H-imidazo[4,5,1-ij]quinolin-2(1H)-one 23a (20 mg, 0.067 mmol) in acetone:water:$^t$BuOH (2 mL, 7:2:1) was treated with NMO (31 mg, 0.268 mmol), osmium tetraoxide (2.5% sol. in $^t$BuOH) (0.136 mL, 0.013 mmol) and cat. t-BuOOH and stirred for 12 hrs at room temperature. The reaction mixture was quenched with ice cold solution of $NaHSO_4$ (2 mL) and extracted with ethyl acetate (3×5 mL) and washed with water and brine. The combined organic layer were dried over $Na_2SO_4$, filtered and concentrated in vacuo, and purified by column chromatography (10% MeOH: $CH_2Cl_2$) to afford compound 23 (15 mg, 68%) as colourless oil.

Data for 23: $^1H$ NMR (400 MHz, METHANOL-$d_4$) δ=7.11-6.96 (m, 3H), 4.04-3.84 (m, 5H), 3.62-3.51 (m, 2H), 1.93 (t, J=5.8 Hz, 2H), 1.36 (s, 6H); $^{13}C$ NMR (101 MHz, CHLOROFORM-d) δ=155.5, 130.1, 129.8, 126.2, 122.7, 117.7, 117.7, 107.7, 71.7, 65.0, 45.5, 37.9, 37.6, 32.9, 29.0.

Example 24

Example 24(a): Synthesis of 6,6-dimethyl-1-(prop-2-yn-1-yl)-5,6-dihydro-4H-imidazo[4,5,1-ij]quinolin-2(1H)-one (24a)

To a solution of 6,6-dimethyl-5,6-dihydro-4H-imidazo[4,5,1-ij]quinolin-2(1H)-one 21c (500 mg, 2.47 mmol) in dry DMF (10 mL) was added caesium carbonate (963 mg, 2.96 mmol) followed by propargyl bromide (0.225 mL, 2.72 mmol) dissolved in dry DMF, was then added drop wise at 0° C. and stirred for 2 h at room temperature. The reaction mixture was added to cold water (10 mL) and extracted with ethyl acetate (3×10 mL) and the combined organic layers were washed with water, brine, then dried over Na2SO4, filtered and concentrated in vacuo, and purified by column chromatography (20% EtOAc: CH2Cl2) to afford compound 24a (550 mg, 94%) as brown sticky solid.

Data for 24a: $^1$H NMR (400 MHz, CHLOROFORM-d) δ=7.10-6.93 (m, 3H), 4.70-4.60 (m, 2H), 3.88 (t, J=6.6 Hz, 2H), 2.27 (s, 1H), 1.94-1.83 (m, 2H), 1.34 (s, 6H); $^{13}$C NMR (50 MHz, CHLOROFORM-d) δ=152.4, 128.4, 126.8, 125.1, 121.0, 116.6, 106.0, 77.3, 72.5, 36.6, 36.3, 31.7, 30.5, 28.5.

Example 24(b): Synthesis of Ethyl 2-(4-((6,6-dimethyl-2-oxo-5,6-dihydro-4H-imidazo[4,5,1-ij]quinolin-1(2H)-yl)methyl)-1H-1,2,3-triazol-1-yl)acetate (24b)

A solution of 6,6-dimethyl-1-(prop-2-yn-1-yl)-5,6-dihydro-4H-imidazo[4,5,1-ij]quinolin-2(1H)-one 24a (50 mg, 0.20 mmol) in acetonitrile (2 mL) was treated with Ethyl azidoacetate (50 mg, 0.22 mmol) and cat. CuI and stirred for 12 h at room temperature. The reaction mixture was added to water and extracted with ethyl acetate (3×10 mL) and washed with water, brine and the combined organic layers were dried over Na$_2$SO$_4$, filtered and concentrated in vacuo. The resultant residue was purified by flash chromatography on silica (50% Ethyl acetate: Dichloromethane) to afford compound 24b (40 mg, 52%) as brown oil.

Data for 24b: $^1$H NMR (400 MHz, CHLOROFORM-d) δ=7.73 (s, 1H), 7.05-6.88 (m, 3H), 5.16 (s, 2H), 5.07 (s, 2H), 4.20 (q, J=7.0 Hz, 2H), 3.91-3.80 (m, 2H), 1.92-1.78 (t, J=5.95 Hz, 2H), 1.31 (s, 6H), 1.23 (t, J=7.1 Hz, 3H); $^{13}$C NMR (101 MHz, CHLOROFORM-d) δ=166.0, 152.8, 143.7, 128.2, 127.1, 124.9, 124.0, 121.0, 116.3, 106.1, 62.2, 50.7, 36.4, 36.4, 36.2, 31.6, 28.4, 13.8.

Example 24: Synthesis of 1-((1-(2-hydroxyethyl)-1H-1,2,3-triazol-4-yl)methyl)-6,6-dimethyl-5,6-dihydro-4H-imidazo[4,5,1-ij]quinolin-2(1H)-one (24)

To a pre-cooled solution of Lithium aluminium hydride (10 mg, 0.27 mmol) in THF (5 mL) was added drop wise solution of Ethyl 2-(4-((6,6-dimethyl-2-oxo-5,6-dihydro-4H-imidazo[4,5,1-ij]quinolin-1(2H)-yl)methyl)-1H-1,2,3-triazol-1-yl)acetate 24b (100 mg, 0.27 mmol) in THF at 0° C. and stirred for 1 hrs at same temperature. Quench the reaction mixture with saturated solution of ammonium chloride (5 mL) and extract with ethyl acetate (3×10 mL) and washed with water, brine and the combined organic layers were dried over Na$_2$SO$_4$, filtered and concentrated in vacuo. The resultant residue was purified by flash chromatography on silica (5% Methanol: Dichloromethane) to afford compound 24 (58 mg, 65%) as white solid product.

Data for 24: $^1$H NMR (400 MHz, CHLOROFORM-d) δ=7.76 (s, 1H), 7.07-6.94 (m, 3H), 5.08 (s, 2H), 4.46-4.36 (m, 2H), 4.03-3.95 (m, 2H), 3.87-3.81 (m, 2H), 2.35 (br. s., 1H), 1.96-1.80 (t, J=5.95 Hz, 2H), 1.32 (s, 6H); $^{13}$C NMR (101 MHz, CHLOROFORM-d) δ=153.0, 143.1, 128.4, 127.1, 124.8, 123.8, 121.3, 116.5, 106.2, 60.8, 52.7, 36.5, 36.4, 36.3, 31.7, 28.5

Example 25

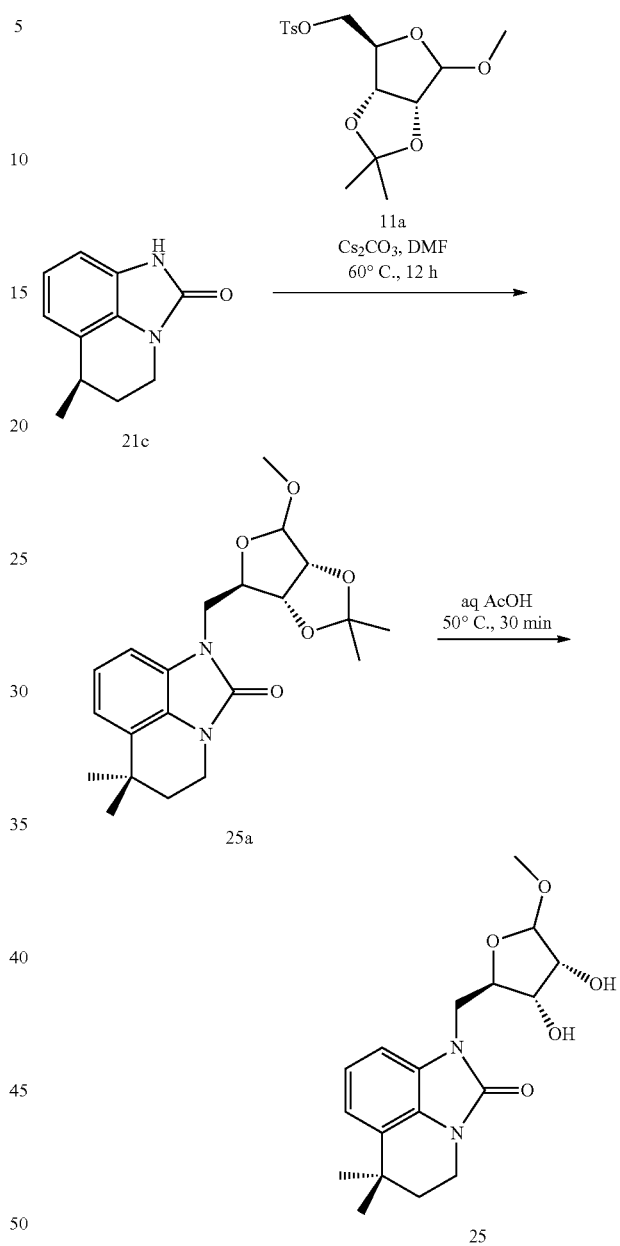

Example 25(a): Synthesis of 1-(((3aR,4R,6aR)-6-methoxy-2,2-dimethyltetrahydrofuro[3,4-d][1,3]dioxol-4-yl)methyl)-6,6-dimethyl-5,6-dihydro-4H-imidazo[4,5,1-ij]quinolin-2(1H)-one (25a)

To a solution of 6,6-dimethyl-5,6-dihydro-4H-imidazo[4,5,1-ij]quinolin-2(1H)-one 21c (100 mg, 0.49 mmol) in dry DMF (5 mL) was added caesium carbonate (0.241 gm, 0.74 mmol) followed by ((3aR,4R,6aR)-6-methoxy-2,2-dimethyltetrahydrofuro[3,4-d][1,3]dioxol-4-yl)methyl 4-methylbenzenesulfonate (212 mg, 0.59 mmol) was then added and stirred for 12 hrs at room temperature. The reaction mixture was added to cold water (10 mL) and extracted with ethyl acetate (3×10 mL) and the combined organic layers were washed with water, brine, then dried over Na2SO4, filtered and concentrated in vacuo, and purified by column chromatography (30% Ethyl acetate: Dichloromethane) to afford compound 25a (135 mg, 70%) as brown sticky solid.

Data for 25a: $^1$H NMR (400 MHz, CHLOROFORM-d) δ=7.08-6.93 (m, 2H), 6.87 (d, J=7.3 Hz, 1H), 5.02 (s, 1H), 4.90 (d, J=6.0 Hz, 1H), 4.74 (d, J=6.0 Hz, 1H), 4.51 (dd, J=4.6, 10.1 Hz, 1H), 4.18 (dd, J=10.5, 14.2 Hz, 1H), 3.88 (t, J=5.7 Hz, 2H), 3.79 (dd, J=4.6, 14.2 Hz, 1H), 3.40 (s, 3H), 1.96-1.84 (t, J=5.95 Hz, 2H), 1.43 (s, 3H), 1.35 (s, 6H), 1.28 (s, 3H); $^{13}$C NMR (101 MHz, CHLOROFORM-d) δ=153.2, 128.4, 127.4, 125.2, 121.0, 116.4, 112.3, 109.8, 105.1, 85.2, 84.1, 82.2, 55.2, 43.9, 36.5, 36.2, 31.7, 28.5, 26.3, 24.9.

Example 25: Synthesis of 1-(((2R,3S,4R)-3,4-dihydroxy-5-methoxytetrahydrofuran-2-yl)methyl)-6,6-dimethyl-5,6-dihydro-4H-imidazo[4,5,1-ij]quinolin-2(1H)-one (25)

A solution of 1-(((3aR,4R,6aR)-6-methoxy-2,2-dimethyltetrahydrofuro[3,4-d][1,3]dioxol-4-yl)methyl)-6,6-dimethyl-5,6-dihydro-4H-imidazo[4,5,1-ij]quinolin-2(1H)-one 25a (70 mg, 0.14 mmol) in Acetic acid:Water (1:1) 1 mL and kept stirring for 3 hrs at 60° C. reaction was monitored by TLC. The reaction mixture concentrated under reduced pressure, and purified by column chromatography (10% MeOH: CH$_2$Cl$_2$) to afford compound 25 (45 mg, 72%) as colourless gum.

Data for 25: $^1$H NMR (400 MHz, METHANOL-D$_4$) δ=7.02 (s, 3H), 4.67 (s, 1H), 4.27-4.21 (m, 1H), 4.20-4.07 (m, 2H), 4.05-3.97 (m, 1H), 3.90-3.83 (m, 3H), 3.19 (s, 3H), 1.93-1.86 (m, 2H), 1.33 (s, 6H); $^{13}$C NMR (101 MHz, METHANOL-D$_4$) δ=155.3, 130.1, 129.7, 126.2, 122.6, 117.7, 110.2, 107.8, 81.9, 76.2, 74.1, 55.9, 45.4, 37.9, 37.6, 32.9, 29.0.

Example 26

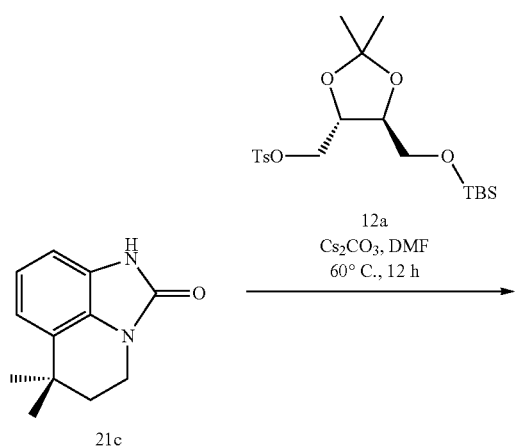

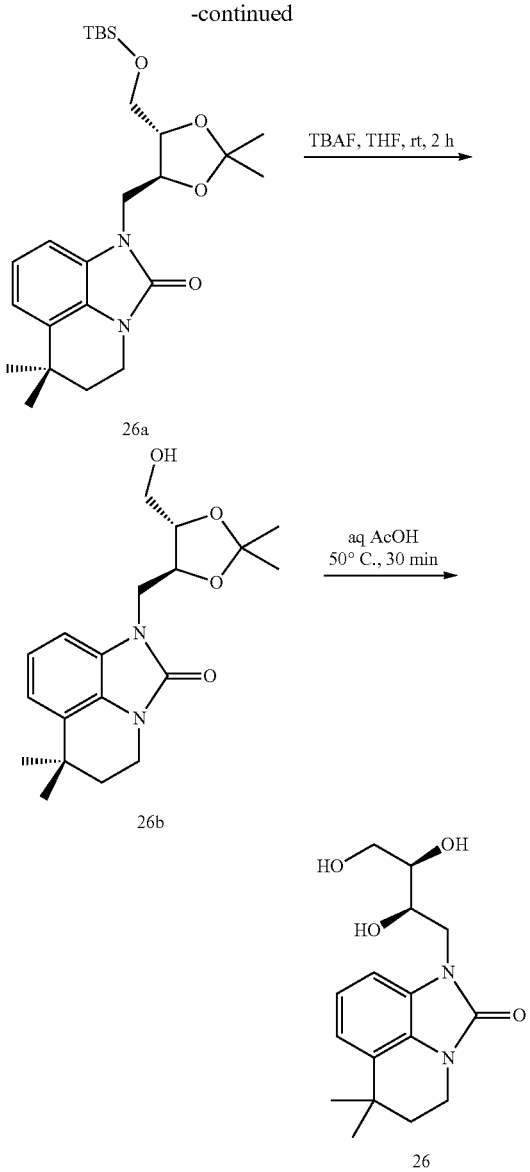

Example 26(a): Synthesis of 1-(((4S,5S)-5-(((tert-butyldimethylsilyl)oxy)methyl)-2,2-dimethyl-1,3-dioxolan-4-yl)methyl)-6,6-dimethyl-5,6-dihydro-4H-imidazo[4,5,1-ij]quinolin-2(1H)-one (26a)

To a solution of 6,6-dimethyl-5,6-dihydro-4H-imidazo[4,5,1-ij]quinolin-2(1H)-one 21c (120 mg, 0.59 mmol) in dry DMF (5 mL) was added caesium carbonate (250 mg, 0.77 mmol) followed by ((4S,5S)-5-(((tert-butyldimethylsilyl)oxy)methyl)-2,2-dimethyl-1,3-dioxolan-4-yl)methyl 4-methylbenzenesulfonate (306 mg, 0.71 mmol) was then added and stirred for 12 h at 60° C. The reaction mixture was added to cold water (10 mL) and extracted with ethyl acetate (3×10 mL) and the combined organic layers were washed with water, brine, then dried over Na2SO4, filtered and concentrated in vacuo, and purified by column chromatography (20% Ethyl acetate: pet ether) to afford compound 26a (190 mg, 69%) as yellow sticky solid.

Data for 26a: $^1$H NMR (400 MHz, CHLOROFORM-d) δ=7.07-6.92 (m, 3H), 4.35 (dt, J=4.1, 6.9 Hz, 1H), 4.16 (dd, J=3.7, 14.2 Hz, 1H), 4.03 (dd, J=6.4, 14.7 Hz, 1H), 3.96-3.87 (m, 3H), 3.78 (d, J=4.1 Hz, 2H), 1.93-1.83 (m, 2H), 1.36 (d, J=2.3 Hz, 6H), 1.35 (d, J=1.8 Hz, 6H), 0.88 (s, 9H), 0.07 (s, 3H), 0.03 (s, 3H); $^{13}$C NMR (101 MHz, CHLOROFORM-d) δ=153.4, 128.3, 128.1, 125.0, 120.8, 116.2, 109.4, 106.6, 79.0, 76.7, 62.8, 43.6, 36.6, 36.3, 31.7, 28.6, 27.1, 26.9, 25.8, 18.3, −5.5, −5.7.

Example 26(b): Synthesis of 1-(((4S,5S)-5-(hydroxymethyl)-2,2-dimethyl-1,3-dioxolan-4-yl)methyl)-6,6-dimethyl-5,6-dihydro-4H-imidazo[4,5,1-ij]quinolin-2(1H)-one (26b)

A solution of 1-(((4S,5S)-5-(((tert-butyldimethylsilyl)oxy)methyl)-2,2-dimethyl-1,3-dioxolan-4-yl)methyl)-6,6-dimethyl-5,6-dihydro-4H-imidazo[4,5,1-ij]quinolin-2(1H)-one 26a (130 mg, 0.28 mmol) in THF 5 mL was added tetra-n-butyl ammonium fluoride TBAF (1M Solution in THF) (0.565 mL, 0.56 mmol) and kept stirring at room temperature for 2 hrs the reaction was monitored by TLC. The reaction mixture diluted with water and extracted with ethyl acetate. Organic layer was then concentrated under reduced pressure, and purified by column chromatography (40% Ethyl acetate: dichloromethane) to afford compound 26b (70 mg, 72%) as colourless gum.

Data for 26b: $^1$H NMR (400 MHz, CHLOROFORM-d) δ=7.11-6.91 (m, 3H), 4.26-4.20 (m, 1H), 4.15-4.11 (m, 2H), 3.96-3.86 (m, 3H), 3.86-3.70 (m, 2H), 2.94 (br. s., 1H), 1.93-1.87 (t, J=5.95 Hz, 2H), 1.37 (s, 3H), 1.35 (s, 3H), 1.34 (s, 3H), 1.20 (s, 3H); $^{13}$C NMR (101 MHz, CHLOROFORM-d) δ=153.9, 128.5, 128.4, 124.9, 121.1, 116.4, 109.3, 107.0, 77.9, 77.6, 62.3, 42.9, 36.6, 36.4, 31.7, 28.6, 28.5, 26.9, 26.8.

Example 26: Synthesis of 6,6-dimethyl-1-((2R,3R)-2,3,4-trihydroxybutyl)-5,6-dihydro-4H-imidazo[4,5,1-ij]quinolin-2(1H)-one (26)

A solution of 1-(((4S,5S)-5-(hydroxymethyl)-2,2-dimethyl-1,3-dioxolan-4-yl)methyl)-6,6-dimethyl-5,6-dihydro-4H-imidazo[4,5,1-ij]quinolin-2(1H)-one 26b (50 mg, 0.14 mmol) in Acetic acid:Water (1:1) 1 mL and kept stirring for 3 h at 60° C. reaction was monitored by TLC. The reaction mixture concentrated under reduced pressure, and purified by column chromatography (5% Methanol: dichloromethane) to afford compound 26 (35 mg, 79%) as colourless gum.

Data for 26: $^1$H NMR (400 MHz, METHANOL-d$_4$) δ=7.12-6.94 (m, 3H), 4.08-3.92 (m, 3H), 3.92-3.79 (m, 2H), 3.72-3.51 (m, 3H), 1.96-1.80 (m, 2H), 1.34 (s, 6H); $^{13}$C NMR (101 MHz, CHLOROFORM-d) δ=155.4, 130.1, 129.7, 126.2, 122.7, 117.7, 107.7, 73.2, 70.4, 64.3, 45.6, 37.9, 37.6, 32.9, 29.0.

Example 27

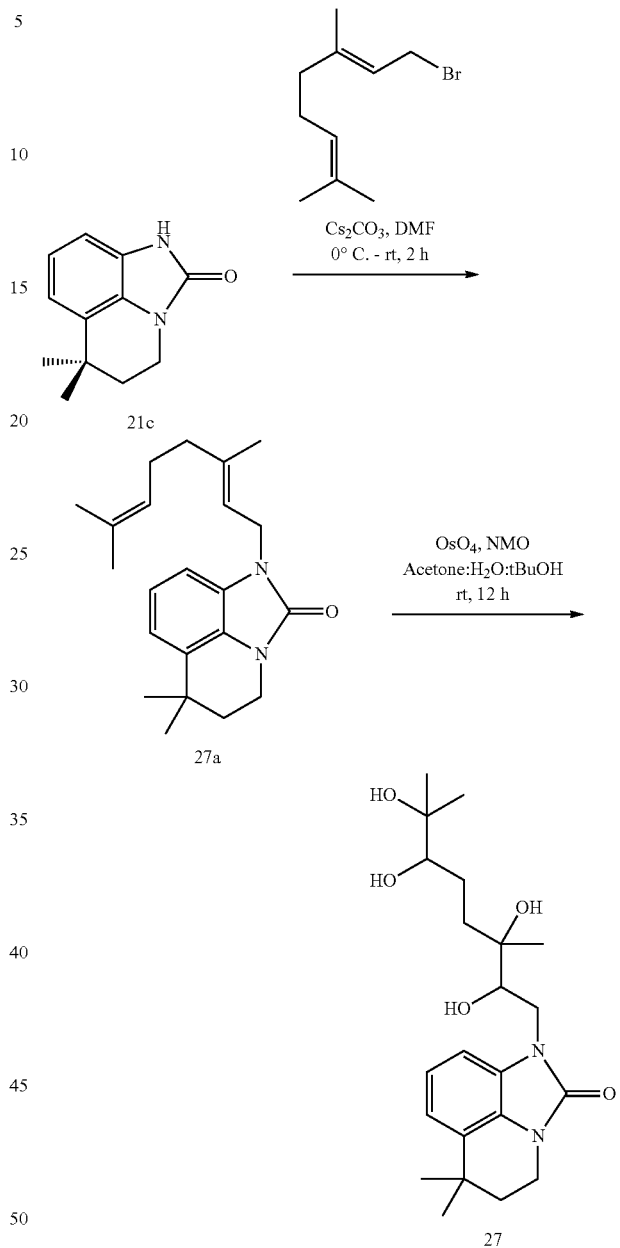

Example 27(a): Synthesis of (E)-1-(3,7-dimethylocta-2,6-dien-1-yl)-6,6-dimethyl-5,6-dihydro-4H-imidazo[4,5,1-ij]quinolin-2(1H)-one (27a)

To a solution of 6,6-dimethyl-5,6-dihydro-4H-imidazo[4,5,1-ij]quinolin-2(1H)-one 21c (200 mg, 0.99 mmol) in dry DMF (5 mL) was added caesium carbonate (386 mg, 1.18 mmol) followed by (E)-1-bromo-3,7-dimethylocta-2,6-diene prenyl bromide (257 mg, 1.18 mmol) was then added and stirred for 4 hrs at room temperature. The reaction mixture was added to cold water (15 mL) and extracted with ethyl acetate (3×30 mL) and the combined organic layers were washed with water, brine, then dried over Na2SO4, filtered and concentrated in vacuo, and purified by column chromatography (30% Ethyl acetate: pet ether) to afford compound 27a (251 mg, 74%) as yellow sticky solid.

Data for 27a: $^{13}$C NMR (101 MHz, CHLOROFORM-d) δ=153.1, 139.5, 131.7, 128.2, 127.7, 125.1, 123.7, 120.7, 119.0, 115.9, 105.7, 39.4, 39.1, 36.7, 36.2, 31.8, 28.5, 26.2, 25.6, 17.6, 16.4.

Example 27: Synthesis of 6,6-dimethyl-1-(2,3,6,7-tetrahydroxy-3,7-dimethyloctyl)-5,6-dihydro-4H-imidazo[4,5,1-ij]quinolin-2(1H)-one (27)

A solution of (E)-1-(3,7-dimethylocta-2,6-dien-1-yl)-6,6-dimethyl-5,6-dihydro-4H-imidazo[4,5,1-ij]quinolin-2(1H)-one 27a (150 mg, 0.44 mmol) in acetone:t-BuOH (3 mL, 8:2) was treated with 50% aq. NMO (0.418 mL, 1.77 mmol), osmium tetraoxide (2.5% sol. in t-BuOH) (0.04 mL, 0.004 mmol) and cat. t-BuOOH and stirred for 4 hrs at room temperature. The reaction mixture was added to cold solution of NaHSO$_4$ and extracted with ethyl acetate (3×30 mL) and washed with water, brine and the combined organic layers were dried over Na$_2$SO$_4$, filtered and concentrated in vacuo. The resultant residue was purified by flash chromatography on silica (5% MeOH: CH$_2$Cl$_2$) to afford hydroxylated compound 27 (96 mg, 53%) as colourless oil.

Data for 27: $^1$H NMR (500 MHz, METHANOL-d$_4$) δ=7.07-7.01 (m, 3H), 4.14-4.07 (m, 1H), 3.98-3.85 (m, 3H), 3.85-3.72 (m, 1H), 3.31-3.25 (m, 1H), 1.95-1.89 (m, 2H), 1.86-1.74 (m, 1H), 1.73-1.64 (m, 1H), 1.64-1.53 (m, 1H), 1.53-1.38 (m, 1H), 1.36 (s, 6H), 1.29 (d, J=4.0 Hz, 3H), 1.21 (s, 3H), 1.18 (d, J=3.4 Hz, 3H); $^{13}$C NMR (126 MHz, METHANOL-d$_4$) δ=155.4, 130.0, 129.8, 126.2, 122.6, 117.5, 107.9, 80.3, 76.5, 74.9, 74.0, 44.7, 37.9, 37.5, 36.6, 32.8, 29.0, 26.3, 25.9, 25.7, 23.4, 23.0.

Example 28

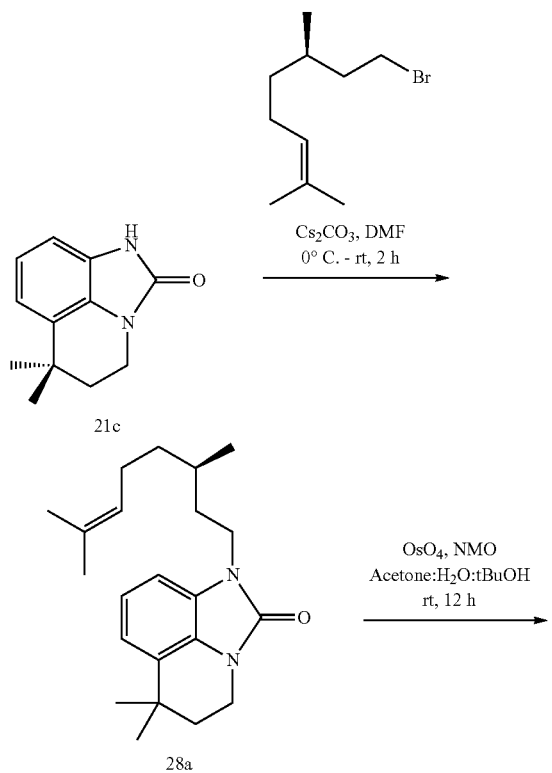

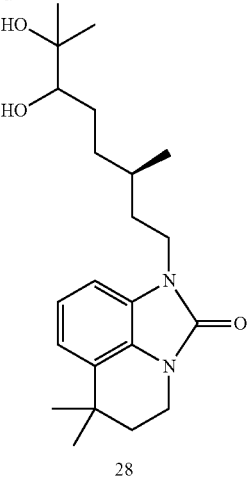

Example 28(a): Synthesis of (R)-1-(3,7-dimethyl-oct-6-en-1-yl)-6,6-dimethyl-5,6-dihydro-4H-imidazo[4,5,1-ij]quinolin-2(1H)-one (28a)

To a solution of 6,6-dimethyl-5,6-dihydro-4H-imidazo[4,5,1-ij]quinolin-2(1H)-one 21c (200 mg, 0.99 mmol) in dry DMF (5 mL) was added caesium carbonate (386 mg, 1.18 mmol) followed by (R)-8-bromo-2,6-dimethyloct-2-ene prenyl bromide (368 mg, 1.18 mmol) was then added and stirred for 12 hrs at room temperature. The reaction mixture was added to cold water (15 mL) and extracted with ethyl acetate (3×30 mL) and the combined organic layers were washed with water, brine, then dried over Na$_2$SO$_4$, filtered and concentrated in vacuo, and purified by column chromatography (30% Ethyl acetate: Dichloromethane) to afford compound 28a (220 mg, 65%) as colourless sticky solid.

Data for 28a: $^1$H NMR (400 MHz, CHLOROFORM-d) δ=7.07-6.94 (m, 2H), 6.82 (d, J=7.6 Hz, 1H), 5.09 (t, J=7.1 Hz, 1H), 3.95-3.83 (m, 4H), 2.08-1.85 (m, 4H), 1.85-1.73 (m, 1H), 1.67 (s, 3H), 1.63-1.50 (m, 5H), 1.47-1.32 (m, 7H), 1.31-1.16 (m, 1H), 1.02 (d, J=6.1 Hz, 3H); $^{13}$C NMR (101 MHz, CHLOROFORM-d) δ=153.3, 131.3, 128.2, 127.8, 125.2, 124.6, 120.7, 115.8, 105.2, 39.4, 36.9, 36.7, 36.2, 35.4, 31.8, 30.2, 28.5, 25.7, 25.3, 19.4, 17.6.

Example 28: Synthesis of 1-((3R)-6,7-dihydroxy-3,7-dimethyloctyl)-6,6-dimethyl-5,6-dihydro-4H-imidazo[4,5,1-ij]quinolin-2(1H)-one (28)

A solution of (R)-1-(3,7-dimethyloct-6-en-1-yl)-6,6-dimethyl-5,6-dihydro-4H-imidazo[4,5,1-ij]quinolin-2(1H)-one 28a (160 mg, 0.47 mmol) in acetone:t-BuOH (3 mL, 8:2) was treated with 50% aq. NMO (0.438 mL, 1.88 mmol), osmium tetraoxide (2.5% sol. in t-BuOH) (0.04 mL, 0.004 mmol) and catalyst t-BuOOH and stirred for 4 hrs at room temperature. The reaction mixture was added to cold solution of NaHSO$_4$ and extracted with ethyl acetate (3×30 mL) and washed with water, brine and the combined organic layers were dried over Na$_2$SO$_4$, filtered and concentrated in vacuo. The resultant residue was purified by flash chromatography on silica (5% MeOH: CH$_2$Cl$_2$) to afford hydroxylated compound 28 (102 mg, 57%) as colourless gum.

Data for 28: $^1$H NMR (500 MHz, CHLOROFORM-d) δ=7.09-6.96 (m, 2H), 6.86 (t, J=7.8 Hz, 1H), 4.17-4.02 (m, 1H), 4.02-3.78 (m, 4H), 3.33 (d, J=10.1 Hz, 1H), 2.5 (bs, 2H), 1.96-1.86 (m, 2H), 1.86-1.70 (m, 2H), 1.70-1.46 (m, 4H), 1.44-1.31 (m, 7H), 1.19 (d, J=5.2 Hz, 3H), 1.16 (d, J=7.6 Hz, 3H), 1.02 (d, J=6.7 Hz, 1H), 0.95 (d, J=6.4 Hz, 1H); $^{13}$C NMR (126 MHz, CHLOROFORM-d) δ=153.5, 128.6, 127.6, 125.1, 120.9, 116.1, 105.4, 78.9, 72.8, 39.1, 36.6, 36.3, 35.9, 35.2, 33.4, 31.8, 30.6, 29.0, 28.2, 26.3, 23.3, 19.8.

Example 29: Antibiotic Assays of Compounds 1 to 28

The minimum inhibitory concentrations (MICs) were determined using the Promega Bac Titer-Glo microbial cell viability assay, which measures cell viability by quantitation of ATP present, an indicator of metabolic activity of cells. The assays were carried out using *Salmonella enterica* strain AMC (ATCC #6539), Inocula of *S. enterica* were prepared from 12-h broth cultures grown in Mueller Hinton broth and the suspensions were then adjusted to a turbidity of 0.5 McFarland. Assays were conducted in a 96-well plate using growth media with an inoculum of ~5×10$^4$ CFU/mL using the suggested protocols. Bacterial cells were treated with hunanamycin analogs for 24 hours at ranges from 0.4 to 40 μg/mL and ciprofloxacin as a control ranging from 0.03 to 10 μg/mL. The OD$_{600}$ was measured using an Envision multi-modal plate reader (Perkin-Elmer, Inc.). The antibiotic assays were performed in Prof. John B. MacMillan's lab, Department of Biochemistry, University of Texas Southwestern Medical Center at Dallas, USA.

TABLE 1

| Compound No. | MIC (μg/mL) |
| --- | --- |
| 1 | 8 μg/mL |
| 2 | 8 μg/mL |
| 3 | 8 μg/mL |
| 4 | >16 μg/mL |
| 5 | 4 μg/mL |
| 6 | >16 μg/mL |
| 7 | >16 μg/mL |
| 8 | >16 μg/mL |
| 9 | 8 μg/mL |
| 10 | >16 μg/mL |
| 11 | >16 μg/mL |
| 12 | >16 μg/mL |
| 13 | 16 μg/mL |
| 14 | >16 μg/mL |
| 15 | >16 μg/mL |
| 16 | >16 μg/mL |
| 17 | ND |
| 18 | ND |
| 19 | ND |
| 20 | ND |
| 21 | 4 μg/mL |
| 22 | ND |
| 23 | >16 μg/mL |
| 24 | >16 μg/mL |
| 24b | 8 μg/mL |
| 25 | 2 μg/mL |
| 26 | >16 μg/mL |
| 27 | ND |
| 28 | ND |

Note:
ND = Not Determined

Advantages of the Invention

Novel compounds of present invention shows potential anti-bacterial activity

Novel preparation route for hunanamycin A providing good yield

Simple and cost-effective process

Hunanamycin A shows potential antibacterial activity

We claim:

1. The tricyclic compound of formula (I)

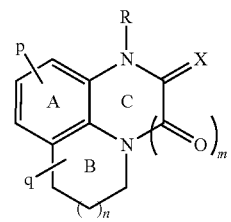

wherein X=O;
wherein R is selected from sugars, heteroaralkyl, hydroxyalkyl, thioalkyl, C1-C5 alkoxyalkyl, aminoalkyl, —NR'R", —CH2NR'R"—CONR'R", —COOR'";
wherein R', R" are independently hydrogen or alkyl, aryl which may have additional substitution;
R' and R" together form a ring with up to six carbon atoms which optionally may be substituted and/or may contain hetero atoms;
R'" is hydrogen or alkyl, aryl which may have additional substitution;
n=0, 1, 2, 3;
m=0;
ring A may be substituted (p) with up to three substitutions which are same or different groups and they are selected from hydrogen, halogen, alkyl, haloalkyl, hydroxyalkyl, thioalkyl, C1-C5 alkoxyalkyl, nitro, aminoalkyl, —NR'R", —CH2NR'R"—CONR'R", —COOR'";
wherein R', R" are independently hydrogen or alkyl, aryl which may have additional substitution;
R' and R" together form a ring with up to six carbon atoms which optionally may be substituted and/or may contain hetero atoms;
R'" is hydrogen or alkyl, aryl which may have additional substitution;
substitutions on ring A together form an additional ring which optionally may be substituted and/or may contain hetero atoms;
ring B may be further substituted (q) with same or different groups and they are selected from hydrogen, halogen, alkyl, haloalkyl, hydroxyalkyl, thioalkyl, C1-C5 alkoxyalkyl, nitro, aminoalkyl, —NR'R", —CH2NR'R"—CONR'R", —COOR'";
wherein R', R" are independently hydrogen or alkyl, aryl which may have additional substitution;
R' and R" together form a ring with up to six carbon atoms which optionally may be substituted and/or may contain hetero atoms;
R'" is hydrogen or alkyl, aryl which may have additional substitution;
substitutions on ring B together form an additional ring which optionally may be substituted and/or may contain hetero atoms; and pharmaceutically acceptable salt thereof.

2. The tricyclic compound of claim 1, wherein the compound is selected from

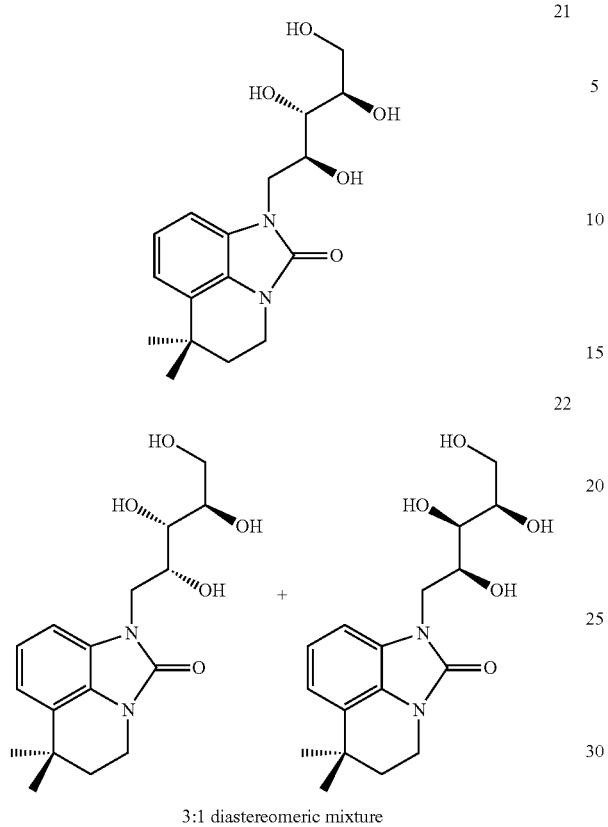
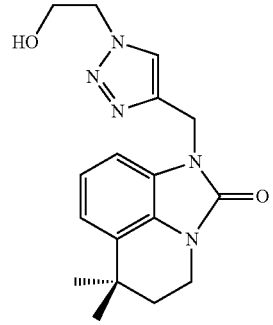
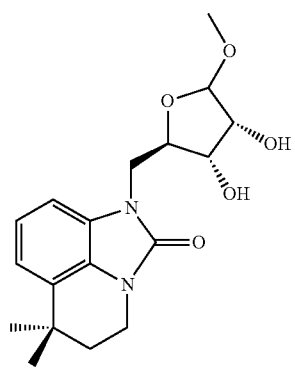
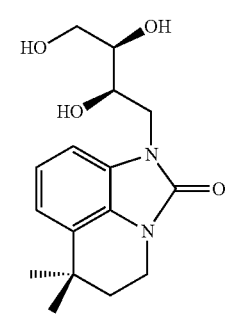
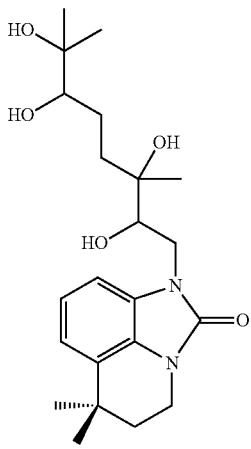

-continued

28

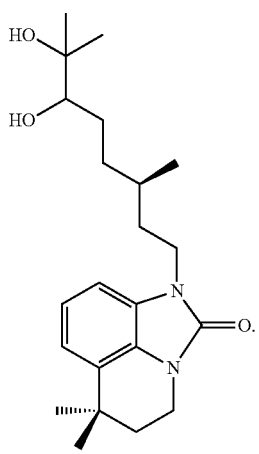

3. An antibacterial agent comprising the tricyclic compound of claim 1.

4. The antibacterial agent of claim 3, wherein the antibacterial agent is active against *Salmonella enterica*.

5. A method of inhibiting the growth of *Salmonella enterica* using the compound of formula 1-(((2R,3S,4R)-3,4-dihydroxy-5-methoxytetrahydrofuran-2-yl)methyl)-6,6-dimethyl-5,6-dihydro-4H-imidazo[4,5,1-ij]quinolin-2(1H)-one (compound 25) wherein the minimum inhibitory concentration is 2 µg/mL.

6. A method of inhibiting the growth of *Salmonella enterica* using the compound of formula 1-((1-(2-hydroxyethyl)-1H-1,2,3-triazol-4-yl)methyl)-6,6-dimethyl-5,6-dihydro-4H-imidazo[4,5,1-ij]quinolin-2(1H)-one (compound 24b) wherein the minimum inhibitory concentration is 8 µg/mL.

7. A method of inhibiting the growth of *Salmonella enterica* using the compound of formula 6,6-dimethyl-1-((2S,3S,4R)-2,3,4,5-tetrahydroxypentyl)-5,6-dihydro-4H-imidazo[4,5,1-ij]quinolin-2(1H)-one (compound 21) wherein the minimum inhibitory concentration is 4 µg/mL.

8. A pharmaceutical composition comprising the tricyclic compound of claim 1 and a pharmaceutically acceptable carrier, diluent or excipient.

9. The tricyclic compound of formula (I)

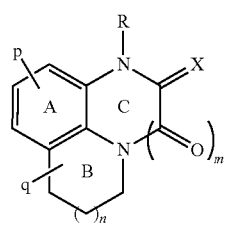

I wherein X=O;

wherein R is selected from sugars, aralkyl, heteroaralkyl, hydroxyalkyl, thioalkyl, C1-C5 alkoxyalkyl, aminoalkyl, —NR'R", —CH2NR'R"—CONR'R", —COOR'";

wherein R', R" are independently hydrogen or alkyl, aryl which may have additional substitution;

R' and R" together form a ring with up to six carbon atoms which optionally may be substituted and/or may contain hetero atoms;

R'" is hydrogen or alkyl, aryl which may have additional substitution;

n=0, 2, 3;

m=0;

ring A may be substituted (p) with up to three substitutions which are same or different groups and they are selected from hydrogen, halogen, alkyl, haloalkyl, hydroxyalkyl, thioalkyl, C1-C5 alkoxyalkyl, nitro, aminoalkyl, —NR'R", —CH2NR'R"—CONR'R", —COOR'";

wherein R', R" are independently hydrogen or alkyl, aryl which may have additional substitution;

R' and R" together form a ring with up to six carbon atoms which optionally may be substituted and/or may contain hetero atoms;

R'" is hydrogen or alkyl, aryl which may have additional substitution;

substitutions on ring A together form an additional ring which optionally may be substituted and/or may contain hetero atoms;

ring B may be further substituted (q) with same or different groups and they are selected from hydrogen, halogen, alkyl, haloalkyl, hydroxyalkyl, thioalkyl, C1-C5 alkoxyalkyl, nitro, aminoalkyl, —NR'R", —CH2NR'R", —CONR'R", —COOR'";

wherein R', R" are independently hydrogen or alkyl, aryl which may have additional substitution;

R' and R" together form a ring with up to six carbon atoms which optionally may be substituted and/or may contain hetero atoms;

R'" is hydrogen or alkyl, aryl which may have additional substitution;

substitutions on ring B together form an additional ring which optionally may be substituted and/or may contain hetero atoms; and pharmaceutically acceptable salt thereof.

\* \* \* \* \*